United States Patent
Klein et al.

(10) Patent No.: US 11,723,859 B2
(45) Date of Patent: *Aug. 15, 2023

(54) TUMESCENT INFILTRATION DRUG DELIVERY OF HIGH SUBCUTANEOUS DRUG CONCENTRATIONS WITH PROLONGED LOCAL AND SYSTEMIC EFFECTS AND MINIMAL LOCAL OR SYSTEMIC TOXICITY

(71) Applicant: HK Pharma, San Clemente, CA (US)

(72) Inventors: Jeffrey Alan Klein, San Juan Capistrano, CA (US); Paytra Alan Klein, Newport Beach, CA (US)

(73) Assignee: HK Pharma, San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/675,506

(22) Filed: Feb. 18, 2022

(65) Prior Publication Data

US 2022/0175664 A1    Jun. 9, 2022

Related U.S. Application Data

(63) Continuation of application No. 16/700,740, filed on Dec. 2, 2019, which is a continuation of application No. 15/291,417, filed on Oct. 12, 2016, now Pat. No. 10,493,024.

(60) Provisional application No. 62/240,439, filed on Oct. 12, 2015.

(51) Int. Cl.

| | |
|---|---|
| *A61K 31/67* | (2006.01) |
| *A61K 9/00* | (2006.01) |
| *A61K 31/522* | (2006.01) |
| *A61K 31/137* | (2006.01) |
| *A61K 31/52* | (2006.01) |
| *A61K 9/08* | (2006.01) |
| *A61K 31/56* | (2006.01) |
| *A61K 45/06* | (2006.01) |
| *A61K 31/546* | (2006.01) |
| *A61K 31/4164* | (2006.01) |
| *A61K 47/02* | (2006.01) |
| *A61K 31/167* | (2006.01) |

(52) U.S. Cl.
CPC ............. *A61K 9/0019* (2013.01); *A61K 9/08* (2013.01); *A61K 31/137* (2013.01); *A61K 31/167* (2013.01); *A61K 31/4164* (2013.01); *A61K 31/52* (2013.01); *A61K 31/522* (2013.01); *A61K 31/546* (2013.01); *A61K 45/06* (2013.01); *A61K 47/02* (2013.01); *A61K 31/56* (2013.01)

(58) Field of Classification Search
CPC ............. A61K 31/137; A61K 31/167; A61K 31/4164; A61K 31/52; A61K 31/522; A61K 31/546; A61K 9/0019; A61K 9/08; A61K 47/02; A61K 31/56; A61K 45/06

See application file for complete search history.

(56) References Cited

U.S. PATENT DOCUMENTS

| | | | |
|---|---|---|---|
| 6,248,345 | B1 | 6/2001 | Goldenheim et al. |
| 10,493,024 | B2 | 12/2019 | Klein et al. |
| 11,241,412 | B2 | 2/2022 | Klein et al. |
| 2002/0077437 | A1 | 6/2002 | Silverberg et al. |
| 2002/0147238 | A1 | 10/2002 | Jerussi et al. |
| 2003/0087962 | A1 | 5/2003 | Demopulos et al. |
| 2009/0098110 | A1 | 4/2009 | Adams, Jr. et al. |
| 2011/0282271 | A1* | 11/2011 | Klein .............. A61M 5/158 604/512 |
| 2012/0195911 | A1 | 8/2012 | Martynov et al. |
| 2012/0322783 | A1 | 12/2012 | Klein |
| 2013/0331313 | A1 | 12/2013 | Berenson |
| 2015/0086494 | A1 | 3/2015 | Sekura et al. |
| 2016/0030387 | A1 | 2/2016 | Winnicki |
| 2016/0235851 | A1 | 8/2016 | Sand et al. |
| 2017/0100331 | A1 | 4/2017 | Klein et al. |
| 2017/0360772 | A1 | 12/2017 | Bosse et al. |
| 2020/0237714 | A1 | 7/2020 | Gabriele et al. |

FOREIGN PATENT DOCUMENTS

| | | | |
|---|---|---|---|
| EP | 3917507 | 12/2021 | |
| WO | WO 2010/028288 A2 | 3/2010 | |
| WO | WO-2010099587 A1 * | 9/2010 | ........... A61K 31/137 |
| WO | WO 2020160328 A1 | 8/2020 | |

OTHER PUBLICATIONS

International Search Report and Written Opinion, PCT/US20/15963, dated May 22, 2020.
Bruni, et al., "Cannabinoid Delivery Systems for Pain and Inflammation Treatment," Molecules, 23, 2478, Sep. 27, 2018.
Klein, Jeffrey A., M.D., "Tumescent Technique for Local Anesthesia Improves Safety in Large-Volume Liposuction," The American Society of Plastic and Reconstructive Surgeons, Nov. 1993 92: 1085-1098.
Shany, Eilon, et al., "Comparison of Continuous Drip of Midazolam or Lidocaine in the Treatmnet of Intractable Neonatal Seizures," Journa lof Child Neurology, vol. 22, No. 3, Mar. 2007.
International Preliminary Report on patentability received in PCT/US2020/15963 dated Aug. 12, 2021.

* cited by examiner

*Primary Examiner* — Sarah Pihonak
(74) *Attorney, Agent, or Firm* — Knobbe Martens Olson & Bear LLP

(57) ABSTRACT

A tumescent composition comprising a chemotherapy agent in a tumescent solution, wherein a tumescent concentration of the chemotherapy agent is simultaneously below a threshold for local, subcutaneous tissue toxicity, above a threshold for positive local therapeutic effect, and above a concentration safely achievable by intravenous (IV), intramuscular (IM) or oral (PO) delivery; and the tumescent solution comprises a vasoconstrictor; a pharmaceutically acceptable carrier; and optionally a local anesthetic.

21 Claims, 14 Drawing Sheets

A

TUMESCENT INFILTRATION DRUG DELIVERY OF HIGH SUBCUTANEOUS DRUG CONCENTRATIONS WITH PROLONGED LOCAL AND SYSTEMIC EFFECTS AND MINIMAL LOCAL OR SYSTEMIC TOXICITY

BACKGROUND

Field

The present embodiments relate to compositions, kits and methods of use of a solution comprising an anesthetic component, a vasoconstrictor component, and an active agent such as an antiviral component, an anti-inflammatory agent and/or a chemotherapy agent for use in medical procedures involving tumescent delivery of high doses of actives for local subcutaneous treatment.

Description of the Related Art

Many medical procedures require infiltration of fluids, such as a local anesthetic. For example, liposuction may be performed entirely by tumescent local anesthesia, which was invented by Jeffrey A. Klein. Dr. Klein first published the description of tumescent local anesthesia to perform liposuction in 1987 (Klein J A. The tumescent technique for liposuction surgery. J Am Acad Cosmetic Surg 4: 263-267, 1987). The tumescent technique was developed in order to eliminate the dangers of liposuction surgery under general anesthesia and the associated excessive bleeding. With proper technique, tumescent infiltration permits liposuction totally by local anesthesia with virtually no surgical blood loss.

One method of infiltration of local anesthetic is via a blunt tipped infiltration cannula. Infiltrators are known as sprinkler-tip or Klein™ needle infiltrators. These cannula are constructed out of a rigid stainless steel and have one or more apertures, which are typically round or oval, and are distributed about the distal end of the cannula. The apertures are distributed over about 15% to 25% or less than 5.0 cm. of the distal end of the cannula needle. These traditional infiltration cannula are intended to be inserted through a small incision in the patient's skin and then moved in and out through the subcutaneous tissue while a dilute solution of local anesthetic (or other pharmaceutical solution) is ejected through the distal apertures. Since the cannula needle is moved in and out, only the distal end (e.g., about 15% to 25%) of the cannula needle may have apertures. Otherwise, fluid may squirt out of the apertures and onto medical professionals when the cannula needle is moved out too much. Such infiltrators typically have a blunt tip and require the placement of a small hole (made by a one mm skin-biopsy punch or a small surgical blade) through which the blunt tipped cannula can be passed. Unfortunately, the piston-like in and out motion of the cannula causes the patient discomfort.

Another type of infiltration cannula is the sharp tipped tumescent infiltration cannula which is available as 1) a single long sharp needle similar to a spinal needle and 2) a group of short sharp hypodermic needles each connected by separate plastic tube to a manifold that distributes Tumescent Local Anesthesia (TLA) solution. The first type of needle is inserted into subcutaneous fat and infiltration proceeds while the needle is continuously moved in and out along paths that radiate from the skin puncture site. A targeted area is eventually anesthetized after multiple skin punctures. The second type, the group of short sharp needles, consists of a group of individual hypodermic needles each attached to an individual IV extension tube, which are in turn connected to a multi-port manifold which connected to a reservoir (IV bag) of tumescent fluid. These sharp-tipped tumescent infiltration devices have been associated with puncture-injury to deeper tissues such as the lungs causing pneumothorax or intra-abdominal viscera causing peritonitis.

In summary, there are two causes of pain associated with the blunt and sharp tipped infiltration cannula. One significant cause of pain is a continuous in and out motion of the cannula as it moves through non-anesthetized tissue. In order to deliver tumescent anesthetic solution throughout an entire compartment of subcutaneous fat, the anesthetist must move the cannula with a continuous to and fro reciprocating motion, and repeatedly change directions. Each advance of the cannula through fat causes discomfort and pain. The second cause of pain is associated with an excessively rapid distention of tissue resulting from a high rate of fluid injection into a relatively small volume of tissue via limited number of holes on the distal tip of the infiltration cannula. Ironically, the pain associated with each of these two factors often necessitates the use of narcotic analgesia, IV sedation, or general anesthesia in order to infiltrate local anesthesia. The present embodiments eliminate or greatly reduce these two sources of pain.

Another method of fluid insertion is via a peripherally inserted central catheter, also called a PICC line comprising an elongate plastic tube that is placed inside a vein of the patient. PICC lines are typically used for procedures requiring delivery of fluids over a prolonged period of time. For example, a PICC line may be used when a patient needs to receive intravenous (IV) fluids, such as medication or nutrients over a prolonged period of time, such as a week or more.

The On-Q® Pain Management System marketed by I-Flow® Corporation employs a flexible plastic or silicone catheter system for continuously providing local anesthetic. This system provides prolonged local anesthesia by means of an elastomeric (elastic container) device that continuously infiltrates a solution of local anesthesia over many hours. The On-Q® device comprises a long soft flexible tube with many small holes arranged along a significant portion of the tube. The On-Q® device is designed to be initially positioned within a surgical wound at the time of surgery. After the surgical wound is closed, the On-Q® device permits slow steady infiltration of a local anesthetic solution into the wound, thereby attenuating post-operative pain. The On-Q® device cannot be inserted through a tiny hole in the skin when there is a need. Therefore the On-Q device cannot achieve infiltration of local anesthesia and prevent post-operative pain in a preemptive fashion. In some versions of the On-Q device, as described in U.S. Pat. No. 7,465,291 (Massengale), a long flexible multi-holed catheter is inserted subcutaneously using an introducer wire and an introducer catheter. This device requires a large sterile field (an area upon which to lay all of the sterile devices used during the insertion process), a complicated insertion protocol, and either general anesthesia or careful pre-insertion infiltration of local anesthesia. Further, the Massengale device is not intend for or capable of being repeatedly inserted in and out of different areas of subcutaneous tissue; it cannot be inserted quickly by untrained personnel in-the-field and far from a sophisticated medical facility. It has been shown that preemptive local anesthesia in the form of peripheral nerve blocks, can prevent nociception by the central nervous system (CNS) during general anesthesia, and thereby prevent chronic post-operative pain syndromes similar to "phantom-limb syndrome." Thus there is a need for a simple device that can permit the direct percutaneous insertion of a multi-holed infiltration cannula into subcutaneous tissue for the localized delivery of medications such as local anesthetics, chemotherapeutic agents, or crystalloids for parenteral hydration. There is also a need for a device that can easily provide localized fluid resuscitation to burn victims whereby fluid is infiltrated into the subcutaneous tissue directly subjacent to burned skin.

Traditional techniques for subcutaneous injection of local anesthetic solutions (e.g., peripheral nerve blocks) use a high-concentration/low-volume of local anesthetic. This is associated with a rapid systemic absorption of the local anesthetic. In order to achieve a prolonged local anesthetic effect, the traditional techniques for using local anesthetics necessitate either frequent repeated injections or slow continuous subcutaneous infusion of the local anesthetic. As described above, repeated injections or piston-like movement of the cannula causes patient discomfort. Slow continuous infiltration may not be desirable in certain situations. Furthermore, continuous infiltrations restrict patient movement for extended periods of time which also cause the patient discomfort. Thus, there is a need for a system for infiltration of a local anesthetic into intact subcutaneous tissue (not necessarily into peri-incisional tissue) which decreases patient discomfort preemptively, and allows prolonged local anesthesia either by rapid (less than 10 to 15 minutes) bolus injections, extended infiltration (e.g. over intervals ranging from 15 minutes to several hours) or continuous slow infiltration over many hours to days. Furthermore there is a need for a device that can provide pre-emptive local anesthesia before a surgical wound is created. There is also a need for a percutaneously-insertable infiltration cannula, with applications that are unrelated to the delivery of local anesthesia, which can be easily inserted by rescuers with minimal clinical skill or training. One example is the need for a cannula that permits emergency fluid resuscitation in situations where an IV cannot be established such as nighttime military combat conditions where using a flash light to establish an IV access would be extremely dangerous. Another example is the need to provide emergency fluid resuscitation to large numbers of patients in acute epidemic diarrhea (dehydration) associated with biological warfare, or mass-trauma situations such as a natural disaster (earth quake) or terrorist attack. There is also a need for a device that can easily provide localized fluid resuscitation to burn victims whereby fluid is infiltrated into the subcutaneous tissue directly subjacent to burned skin.

Other types of devices for delivering fluid to a patient exist in the prior art. For example, U.S. Pat. Pub. No. 2003/0009132 (Schwartz et al.) is directed to a micro-intravascular (never extra-vascular) catheter for infusing milliliter quantities of drugs for the lysis of intravascular blood clots (i.e., a micro target). Another embodiment of the Schwartz device is intended to improve the precision and safety of intra-myocardial delivery of micro-liter volumes of fluid for biologic gene therapy based angiogenesis.

Unfortunately, the Schwartz device requires a sterile high tech hospital environment and demands fluoroscopy and ultrasound guidance. The Schwartz device requires a highly trained, experienced and skilled medical professional to operate. In particular, the Schwartz infiltration catheter is defined by its obligatory guidewire and intravascular target. The intravascular insertion of the catheter via the guidewire is a complex procedure that requires significant clinical training, experience and skill. Specifically, it involves 1) preparation with a sterile surgical field, 2) making a skin incision and inserting an introducing catheter having coaxial stylet into the targeted vessel, 3) removing the stylet, 4) inserting the guidewire through the introducing catheter and into the vessel, 5) withdrawing the introducing catheter from the vessel without disturbing the intravascular location of the guidewire, 6) slipping the distal tip of the infiltration catheter over the proximal end of the guidewire, and advancing the infiltration catheter over the considerable length of the guidewire through the skin and into the intraluminal space of the targeted vessel, 7) withdrawing the guidewire and attaching the proximal end of the infiltration catheter to a source of the therapeutic fluid to be delivered into the targeted vessel. This insertion procedure is so specialized that a majority of physicians do not have the requisite expertise to qualify for hospital privileges for inserting an intravascular catheter using a guidewire. Locating a clotted blood vessel and inserting the Schwartz catheter into the vessel requires ultrasound guidance.

As understood, an important feature of the Schwartz device is the shape, size, direction and pattern of the holes on the infiltration cannula. As stated in paragraph 15 of the Schwartz disclosure, "there is a need for an injection device that gives control over the concentration, pattern, and location of the deposition of an injectate." The Schwartz device is intended to improve directional control over the direction of injection of minute volumes of injectate.

The Schwartz device appears to be specifically designed to avoid vascular compression. For the small needle embodiment of Schwartz, vascular compression resulting from injecting excessive volume of drug into myocardium may precipitate infarction or arrhythmia. Likewise, for the long cannula embodiment of Schwartz vascular compression appears to be contraindicated. The goal of infusing fluid into a vessel containing a blood clot is to open the vessel, and not compress it.

The Schwartz device also appears to be incapable of large volume (e.g., multi liter) subcutaneous infiltration. The long plastic Schwartz catheter appears to be specifically intended for intravascular use. Moreover, Schwartz cannula cannot have holes distributed along 100% of its entire length based on a contention that such situation will lead to a contradictory situation. If the Schwartz device does have holes along its entire length then either the entire length of the cannula would have to be positioned inside a vessel (unlikely without attaching the cannula proximally to another catheter in which case the bulky attachment mechanism would have to be passed through the wall of the vessel) or else some of the holes would have an extravascular location (unlikely because the therapeutic fluid would either leak onto the patient's skin or extravasate into the perivascular and subcutaneous tissues). In either case, the potential for serious adverse effects would be significant.

Moreover, the Schwartz device does not appear to be capable of being reciprocated in and out of the subcutaneous tissue of the patient to locally anesthetize an entire compartment.

In summary, the Schwartz infiltrator is intended for 1) intravascular insertion which demands a complex guidewire procedure involving several steps, 2) intravascular drug delivery (for lysis of blood clots) or intra myocardial injections, 3) injection of a miniscule volume (micro liters) of drug.

Another type of device for delivering fluid to a patient is described in U.S. Pat. No. 6,524,300, issued to Meglin. Similar to the Schwartz device, the Meglin device appears to be an intravascular device intended to inject a "medical agent into the target lumen of the body." (see, Col. 2, lns. 41-48). Meglin is specifically intended to be inserted intraluminally into "a lumen of a blood vessel or another cavity within a patient's body." (see Col. 1, lns. 14-19). This is precisely opposite the goal of a tumescent infiltration cannula. A tumescent infiltration cannula is intended to deliver drugs to the subcutaneous space which excludes the vascular space and cavitary space. As such, the Meglin device appears to be specifically designed to avoid vascular compression and to not induce vasoconstriction. An important aspect of the Meglin device appears to be the size and density of the apertures to control the rate of flow of fluidic medication. Moreover, it appears that the medical professional utilizing the Meglin device requires a great deal of training, expertise and education based on a contention that the infusion segment of the device is located intravascularly by locating a radiopaque marker band with a fluoroscopy.

Another type of device for delivering fluid to a patient is described in U.S. Pat. No. 6,375,648, issued to Edelman, et al. Similar to prior art blunt or sharp tipped infiltration cannula, the apertures are restricted to the distal 25% of the cannula. The reason is that otherwise, the fluidic medication would squirt out of the apertures and contaminate the operating room. Col. 2, lns. 22-25 states that "once within the tissue of a patient a treatment solution may be infused into the tissue by working the cannula 20 through the fat tissue of the patient." As understood, the Edelman device suffers from the same deficiencies discussed above in relation to the blunt or sharp tipped infiltration cannula. The Edelman cannula is reciprocated in and out of the subcutaneous tissue, and thus, causes pain or discomfort to the patient. Moreover, the only novel aspect of Edelman appears to be the cannula's Teflon coating.

Surgical site infections are a significant source of postoperative morbidity and mortality. They account for 17% of all hospital acquired infections, require prolonged hospital stays and contribute substantially to health care costs. The incidence of surgical site infection is a function of the type of surgical procedure, the surgeon, and the hospital. The risk of surgical site infection is significantly associated with a number of factors including anesthetic risk scores, wound class and duration of surgery.

The true incidence of surgical site infection is probably higher than what has been reported in the literature. The primary surgical team is often not aware of incisional infections diagnosed after hospital discharge. Patients who had surgical site infection diagnosed after discharge require substantially more outpatient visits, emergency visits, radiology services and home healthcare services. A study published in 2004 found such infections cost $6,200 per patient for home care expenses associated with wound care. The major sources of infection are microorganisms on the patient's skin. A number of preoperative skin care techniques have been used to limit concentrations of bacteria at the surgical site, including antiseptic preparations, adhesive barrier drapes, topical antibiotics, hair removal and hand hygiene.

Antimicrobial prophylaxis with intravenous (IV) antibiotics is currently the most important clinical modality for preventing surgical site infection. The consensus recommendation for antimicrobial prophylaxis is for antimicrobial agents to be given as an IV infusion of antibiotics administered within the first 60 minutes before surgical incision and that prophylactic antimicrobial agents be discontinued within 24 hours of the end of surgery.

Recent Center for Disease Control (CDC) guidelines for antimicrobial prophylaxis do not mention preoperative peri-lesional infiltration of antibiotics. A recent review of surgical site infections only discussed intravenous (IV) delivery of prophylactic antibiotics. The possibility of preoperative peri-incisional infiltration to prevent SSI was not considered.

Several studies of surgical site infection in the 1980's compared the effectiveness of antimicrobial prophylaxis by IV infusion or by peri-incisional infiltration. A 1981 study of the incidence of wound infection among 405 abdominal surgery patients found no significant difference between 1 gm of cephaloridine given intravenously or intra incisional at the end of the surgery. Following this trial, IV antibiotics at the induction of anesthesia became standard practice.

An IV infusion of fluid is a common medical procedure to treat patients. Unfortunately, an IV infusion is associated with an inherent expense, difficulty and risk. There are also unfortunately times when an IV line cannot be established in the patient. By way of example and not limitation, the patient may be burned such that a vein of the patient cannot be located to establish an IV access. The patient may have been traumatized in such a way that will not allow a doctor to perform an IV cut down procedure. Additionally, the patient may be very obese such that the vein of the patient is difficult to locate. In other situations, occurring in remote locations where a trained medical professional is not available to establish the IV, such as the international space station or on an airplane. Currently, there does not appear to be any in-flight capability for treating an acute traumatic injury on a plane or on the space shuttle. If the pilot or astronaut survives the immediate effects of an explosion, burn, or decompression injury, or if there is an acute non-traumatic medical illness, it is assumed that the victim must return to terra firma for any significant therapeutic intervention such as providing systemic fluid replacement. Other situations include a mass casualty situation where there are insufficient numbers of trained medical professionals compared to the number of victims/patients, etc.

Other methods of delivering a drug to a patient other than IV administration may be oral delivery of the drug. Unfortunately, oral delivery of the drug results in inconsistent absorption of the drug into the gastrointestinal tract. The drug may alternatively be delivered via periodic intramuscular injections. Unfortunately, the fluidic drug serum may have varying levels of concentration at each of the periodic injections.

There are also problems with systemic administration of antibiotics, whether by IV or oral administration, as a prophylactic or treatment method for surgical site infection or other acute infections. For example, systemic levels in the blood may be high enough to cause significant side effects, while antibiotic levels at the surgical site or site of infections may not be sufficient to prevent or treat infection. One dose-related problem frequently reported by patients receiving systemic antibiotic administration is gastrointestinal toxicity. Systemic administration of antibiotics can kill off the protective natural flora in the gut, resulting in conditions favorable for the overgrowth of certain antibiotic-resistant pathogens, specifically *Clostridium difficile*. This can result in a condition known as *Clostridium difficile* colitis. It follows that there exists a need to improve the function of antibiotic prophylaxis at the surgical site while reducing the unwanted side effects of systemic antibiotic administration.

SUMMARY

Some embodiments relate to a method of subcutaneous delivery of a drug or a therapeutic agent to a subject including administering to said subject a tumescent composition that includes:
  (a) the drug or the therapeutic agent, wherein a tumescent concentration of the drug is simultaneously:
    1) below a threshold for local, subcutaneous tissue toxicity,
    2) above a threshold for positive local therapeutic effect, and
    3) above a concentration safely achievable by intravenous (IV), intramuscular (IM) or oral (PO) delivery;
  (b) a vasoconstrictor; and
  (c) a pharmaceutically acceptable carrier.

In some embodiments, infiltration of the tumescent composition achieves both prolonged local drug concentration within a tumescent subcutaneous tissue as well as a prolonged slow constant systemic absorption of drugs from the tumescent tissue into a systemic circulation.

In some embodiments, a pharmacokinetic profile of the systemic absorption resembles a slow, constant, intravenous (IV) infusion.

In some embodiments, the subcutaneous concentration of the drug or therapeutic agent achieved is from about 1-100 times the maximum subcutaneous interstitial fluid concentration that can be achieved by conventional IV, IM or oral delivery of the drug or therapeutic agent.

In some embodiments, the tumescent composition further includes an anesthetic component.

In some embodiments, the anesthetic component is a local anesthetic.

In some embodiments, local and systemic blood viscosity are reduced in the subject and local and systemic oxygenation of tissues in the subject is increased.

In some embodiments, the local anesthetic is lidocaine.

In some embodiments, the concentration of lidocaine is approximately 100 mg to 1,500 mg per L of solution.

In some embodiments, the tumescent composition further includes an anti-inflammatory agent.

In some embodiments, the tumescent composition further includes an antibiotic component.

In some embodiments, the antibiotic component includes cefazolin.

In some embodiments, the drug or therapeutic agent is an antiviral agent.

In some embodiments, the antiviral component is acyclovir.

In some embodiments, the vasoconstrictor component includes epinephrine.

In some embodiments, the concentration of epinephrine is approximately 0.2 to 1.5 mg/L In some embodiments, the subject has a localized viral infection.

In some embodiments, the subject is infected by the varicella-zoster virus.

In some embodiments, the tumescent composition includes an agent that reduces neuropathic pain or the risk of developing neuropathic pain In some embodiments, the neuropathic pain is selected from the group consisting of postherpetic neuralgia, trigeminal neuralgia, phantom limb pain, diabetic neuropathy, carpal tunnel syndrome, sciatica, degenerative disk disease, spinal cord injury, post-surgical pain and cancer.

In some embodiments, the tumescent composition includes a chemotherapy agent, wherein the method treats a localized cancer.

In some embodiments, the localized cancer is selected from the group consisting of skin cancer, breast cancer, lymphoma, Pancreatic Adenocarcinoma, Insulinoma, lung cancer, colon cancer, prostate cancer, ovarian cancer and a metastatic cancer.

In some embodiments, the skin cancer is selected from the group consisting of Basal Cell Carcinoma, Squamous Cell Carcinoma, melanoma, Merkel Cell Carcinoma and Kaposi's Sarcoma.

Some embodiments relate to a method of treating or preventing sepsis or Systemic Inflammatory Response Syndrome (SIRS) in a subject including:
  (a) identifying a subject suffering from or at risk of sepsis or SIRS; and
  (b) administering to said subject a tumescent composition including:
    (i) a drug or the therapeutic agent, wherein a local, subcutaneous concentration of the drug or the therapeutic agent is simultaneously:
      (1) below the threshold for local tissue toxicity, and
      (2) greater than the maximum subcutaneous interstitial fluid concentration that can be safely achieved by conventional systemic delivery, intravenous delivery or oral delivery of the drug or the therapeutic agent;
    (ii) a vasoconstrictor; and
    (iii) a pharmaceutically acceptable carrier,
  wherein the tumescent composition acts as a reservoir for the drug or therapeutic agent, simultaneously providing a sustained high local interstitial drug concentration and a sustained systemic concentration of the drug or therapeutic agent resembling a slow constant IV infusion in the subject, thereby effectively treating or preventing sepsis or SIRS in the subject.

Some embodiments relate to a tumescent solution for treating a localized varicella-zoster viral infection (shingles), the tumescent solution including:
  an antiviral agent selected from acyclovir, valacyclovir, famciclovir, brivudine, docosanol, idoxuridine, penciclovir or trifluridine, or combinations thereof;
  epinephrine;
  a local anesthetic;
  10-25 mEq of sodium bicarbonate buffer; and
  a pharmaceutically acceptable carrier,
wherein the antiviral agent is present at a concentration of 0.1 g/L-10 g/L, the epinephrine is present at a concentration of 0.5 to 1 mg per L, and the local anesthetic is present at a concentration of 500 mg to 1,000 mg per L.

In some embodiments, the local anesthetic is an amide-type or an ester-type local anesthetic.

In some embodiments, the local anesthetic is selected from the group consisting of lidocaine, benzocaine and bupivacaine.

In some embodiments, the local anesthetic is a neurotoxin-type local anesthetic.

In some embodiments, the neurotoxin-type local anesthetic is neosaxitoxin.

In some embodiments, the local anesthetic includes an amide-type local anesthetic and/or an ester-type local anesthetic in combination with a neurotoxin-type local anesthetic Some embodiments relate to a kit for treating a localized varicella-zoster viral infection (shingles), the kit including:
  an IV-like bag including a pharmaceutically acceptable carrier selected from the group consisting of a saline solution, a lactated Ringer's solution, and Hartmann's solution;

an antiviral agent in concentrated form;

a sterile solution including epinephrine in concentrated form;

a sterile solution including lidocaine in concentrated form;

a sterile solution including a bicarbonate buffer in concentrated form;

instructions on how to mix the components;

a safety label for the IV-like bag, wherein the label indicates that the IV-like bag is not for IV use); and optionally an infusion cannula.

DETAILED DESCRIPTION OF CERTAIN EMBODIMENTS

Tumescent Infiltration Drug Delivery

Figure 1:
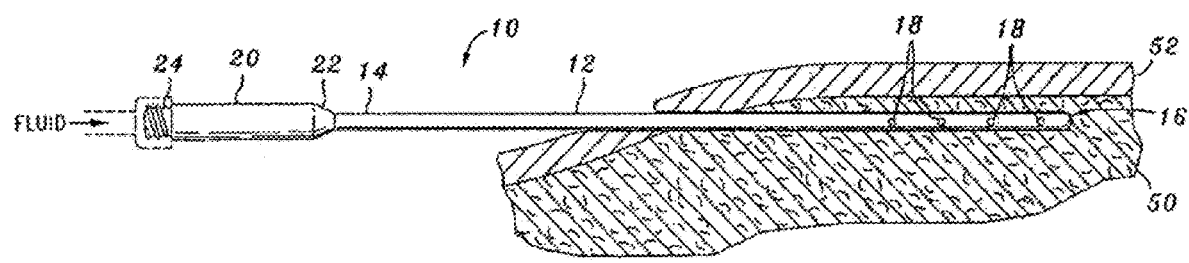
FIG. 1 is a side elevation view of a stainless steel infiltration cannula with a closed tip shown inserted in subcutaneous tissue shown in partial cross section.

Disclosed herein are methods that utilize as tumescent infiltration (TI) drug delivery. TI comprises a novel mode of drug delivery having a unique multi-compartment pharmacokinetic performance and presenting unique therapeutic opportunities. From a pharmacokinetic perspective, TI is functionally distinct from IV (intravenous), IM (intramuscular), PO (per os, oral), topical (percutaneous) and simple subcutaneous injection.

After tumescent infiltration, subcutaneous interstitial fluid (ISF) is designated tumescent interstitial fluid (TISF). Infiltration refers to drug delivery by injection of a liquid into a tissue. Infusion refers to drug delivery by pouring a liquid into a vein.

TI drug delivery is the direct subcutaneous infiltration of drug(s) dissolved in a large volume of a physiologic crystalloid solution such as 0.9% physiologic saline or lactated Ringer's solution. Depending on the clinical objective, a TI solution may contain a dilute vasoconstrictor (e.g., epinephrine) for delayed systemic absorption or a dilute capillary vasodilator (e.g., lidocaine or niacin) for rapid systemic absorption. (see, U.S. Pat. No. 7,572,613).

TI drug delivery provides unique subcutaneous and systemic concentration-time profile (bioavailability) of a wide range of drugs (antibiotic, antiviral, antifungal, anticancer, analgesic, local anesthetic, biologic, etc.) following subcutaneous tumescent infiltration (TI) drug delivery. Specifically TI simultaneously produces:
1) Subcutaneous concentrations of a drug that are safe but also far exceed concentrations achievable by any other mode of drug delivery.
2) Systemic (serum) concentrations of the drug with a concentration-time profile resembling a slow constant IV infusion.

TI comprises a combination of a unique delivery vehicle with unique properties and a drug delivery method. TI drug delivery consists of a drug (D) dissolved in a dilute tumescent solution that typically consist of lidocaine (≤1 gm/L), epinephrine (≤1 mg/L), sodium bicarbonate 10 mEq/L in 0.9% physiologic saline. Alternative embodiments of TLA can involve higher or much lower concentrations of these components and/or alternative local anesthetics.

TI drug delivery permits safe and effective local (subcutaneous or deep tissue) infiltration of a large dose of a drug in a large volume of a dilute solution, which otherwise could not be injected because of dose-related systemic toxicity (typically manifested as pain, inflammation or necrosis.

One embodiment of TI drug delivery consists of a large volume of dilute tumescent drugs injected subcutaneously. In another embodiment, a small volume of dilute tumescent anti-tumor drugs is injected directly over a certain time interval, often prolonged, into a deep parenchymal tissue to target a malignant neoplasm.

Examples of specific embodiments of TI drug delivery include:
1) prevention of surgical site infections,
2) treating necrotizing soft tissue infections where IV antibiotic delivery may be inadequate because of blood vessel necrosis,
3) treating localized cutaneous infections in immunocompromised patients,
4) tumescent infiltration acyclovir delivery for treating *Herpes zoster*,
5) tumescent antifungal delivery for local treatment of cutaneous superficial or deep fungal infections with a relatively high local drug concentrations while significantly reducing the peak serum concentration associated with nephrotoxic, hepatotoxic and ototoxic drugs,
6) tumescent anti-neoplastic delivery for treating cutaneous and subcutaneous malignancies or metastases, for example "in-vivo gene transfer" or biologic drug delivery targeting pancreatic adenocarcinoma,
7) tumescent delivery of a biologic drug consisting of a large molecule snake antivenin for targeting the toxic venom proteins as they are absorbed via lymphatic vessels.

Specific Advantageous Features of Tumescent Drug Delivery

Tumescent Infiltration Drug Delivery has a unique ability to achieve both a relatively high prolonged local drug concentration within the tumescent subcutaneous tissues as well as a prolonged slow constant systemic absorption of drugs from the tumescent tissues into the systemic circulation, where the pharmacokinetic profile of the systemic absorption resembles a slow constant IV infusion. This unique feature of tumescent infiltration (TI) cannot be matched by any other mode of drug delivery. TI is a novel mode of concomitant prolonged local and prolonged systemic drug delivery with unanticipated therapeutic benefits.

(A) Incremental dilution of an arbitrary drug D progressively reduces its subcutaneous toxicity. For any given commercial formulation of a water soluble drug D that is toxic when injected into subcutaneous tissue, there is always a sufficient tumescent dilution of drug D that is not toxic upon subcutaneous injection.

(B) The definition of TTAR: The tumescent therapeutic ambit range (TTAR) of a drug D is defined as the range of the drug's concentrations within a tumescent solution, such that the tumescent concentration of D is simultaneously:
1) below the threshold for local tissue toxicity,
2) above the threshold for positive local therapeutic effect,
3) above the concentration achievable by IV, IM or PO delivery.

It is to be understood that a concentration threshold for a drug effect is rather nebulous. A precise definition would require a statistical estimate of a safe dose using statistical tolerance interval analysis. For example "safe" is defined as the estimated dose where, with 95% confidence, the risk of a mild toxic event after a single dose is than 1/1,000.

In some embodiments, the subcutaneous concentration of the drug, or therapeutic agent, achieved is from about 1-100 times the maximum subcutaneous interstitial fluid concentration that can be achieved by conventional intravenous delivery or oral delivery of the drug or therapeutic agent. In some embodiments, the subcutaneous concentration of the drug or therapeutic agent achieved is from about 2, 3, 4, 5, 6, 7, 8, 9, 10, 15, 20, 25, 30, 35, 40, 45, 50, 55, 60, 65, 70, 75, 80, 85, 90 or 95 times the maximum subcutaneous interstitial fluid concentration that can be achieved by conventional intravenous delivery or oral delivery of the drug or therapeutic agent.

(C) Some drugs may not have a tumescent therapeutic ambit range. For example, a sufficiently safe dilution may be too dilute to have a positive therapeutic effect; or the subcutaneous bioavailability of the drug by TI is equal to that of either IV, IM or PO delivery.

Some drugs are inherently painful upon injection. Dilute Tumescent infiltration of a drug is less painful because dilute drug is less painful than more concentrated drug solutions and because dilute lidocaine in the solution eliminates the pain caused by subcutaneous delivery.

(D) In certain clinical situations tumescent lidocaine (high prolonged wide-spread local subcutaneous concentrations) provides important unanticipated therapeutic benefits that are not available with IV, IM or oral delivery. For example, tumescent lidocaine (at concentrations that are significantly higher than can be safely achieved by IV, IM or PO delivery) has antibacterial, antithrombotic and anti-inflammatory properties. These are a unanticipated unique features of TI drug delivery that IV, IM, and PO delivery do not provide.

(E) A lidocaine component of TI drug delivery can provide pain relief for pain associated with a disease being treated by TI. For example TLA can relieve the acute pain associated with *Herpes zoster*. This is a unique feature of TI drug delivery that IV, IM, and PO delivery do not provide.

(F) Dilute epinephrine in the TI solution induces intense prolonged local subcutaneous capillary vasoconstriction. This TI vasoconstriction accounts for uniquely beneficial pharmacokinetic properties. The TI local vasoconstriction profoundly delays the systemic absorption of all the drugs in the TI solution. The consequences of this delayed systemic absorption is that the local drug effect of a given dose of drug D is prolonged far beyond that which can be achieved by an equal dose IV or oral dose of D. Thus, the subcutaneous bioavailability of D, as determined by the area under the curve (AUC) of the concentration-time profile combined with the prolonged time within the tumescent therapeutic ambit range (TTAR), is often significantly greater by TI compared to IV, IM or oral delivery.

(G) Slow systemic drug absorption associated with tumescent infiltration delivery of a highly dilute tumescent solution produces a serum concentration-time profile resembling a slow IV infusion with prolonged systemic effects. This slow "IV delivery" can replace or supplement the standard oral or IV delivery of the drug and results in less variation of serum drug concentrations.

(H) An important pharmacokinetic advantages of TI drug delivery is a prolonged local drug effect (e.g., prolonged T>MIC) in relatively avascular subcutaneous fat and concomitant prolonged systemic concentrations with relatively small Cmax in serum. The small serum Cmax is particularly advantageous with tumescent infiltration antibiotic delivery to prevent or treat a localized skin infection while simultaneously minimizing the peak antibiotic concentration within the gut and thus reducing the risk of antibiotic-associated *C. difficile* diarrhea.

(I) Large volume tumescent infiltration of dilute drug spreads drug throughout a larger area and larger volume of subcutaneous tissue than can be treated with injection of an equal mg dose at commercial out-of-the-bottle concentrations.

(J) TI drug delivery can be performed by any primary care provider (physician, physician's assistant, nurse practitioner) in an office or clinic setting.

Examples of TI pharmacokinetic profiles include TI (antibiotic & lidocaine) delivery and TI (acyclovir & lidocaine) delivery:

1) Local and systemic TI antibiotic & lidocaine drug delivery prevents and treats systemic inflammatory response syndrome (SIRS) and bacterial sepsis. (See below for a more detailed description of the therapeutic advantage of TI antibiotic & lidocaine delivery for treatment of SIRS and sepsis). Briefly, local TI antibiotic & lidocaine delivery prevents SIRS by engulfing and isolating damaged (traumatized or infected) subcutaneous tissue within a persistent mass of vasoconstricted tumescent fluid. Systemic T I antibiotic & lidocaine delivery treats SIRS by significantly down regulating systemic inflammatory mediators. In addition, TI lidocaine delivery prevents platelet activation both locally and systemically and thereby and attenuates platelet-mediated inflammatory response. It is known that TI lidocaine prevents thromboembolism (U.S. Pat. No. 8,957,060 B2, Tumescent antibiotic solution).

2) Local and systemic TI acyclovir and lidocaine delivery for treatment of the acute pain and tissue damage of *Herpes zoster* dermatitis and prevention of dreaded post-herpetic neuralgia (PHN). It is known that tumescent lidocaine (without acyclovir) can relieve the pain of acute zoster dermatitis. With acyclovir in the tumescent solution, TI delivery achieves subcutaneous acyclovir concentrations that far exceed concentrations achievable by IV delivery; the result is decreased varicella zoster virus (VZV) replication, decreased extent, severity and of VZV dermatitis, shortened duration of VZV dermatitis, decreased inflammatory damage to nerves and decreased risk of chronic post-herpetic neuralgia. In addition, systemic absorption of acyclovir following subcutaneous TI acyclovir delivery produces sustained therapeutic serum acyclovir concentrations and thereby reduces VZV viremia. (A more detailed description of the therapeutic advantage of TI acyclovir delivery for treatment of the acute zoster dermatitis and preventing PHN is presented below).

TI allows direct subcutaneous infiltration of drugs which otherwise cannot be injected subcutaneously because of pain or tissue toxicity. Indeed, there are a number of drugs that are never injected subcutaneously because the Food and Drug Administration (FDA) approved package insert labeling states explicitly that the drug should NOT be injected subcutaneously.

Acyclovir is a specific example of a drug for which the FDA countermands subcutaneous injection. The FDA-approved package insert labeling for IV acyclovir states, "Acyclovir Injection is intended for intravenous infusion only, and should not be administered topically, intramuscularly, orally, subcutaneously, or in the eye." Nevertheless, we have found that, in clinical practice, TI delivery of acyclovir is safe and effective.

Among the drugs that have been reported to be associated with subcutaneous tissue toxicity as the result of extravasation or infiltration at an IV site are the following: phenytoin, calcium gluconate, potassium chloride, calcium chloride, dopamine, dextrose solutions, epinephrine, sodium bicarbonate, nafcillin, propofol, norepinephrine, arginine, promethazine, vancomycin, tetracycline, dobutamine, vasopressin, acyclovir, amphotericin, ampicillin, cloxacillin, gentamicin, metronidazole, oxacillin, penicillin, amiodarone, albumin, furosemide, lorazepam, immunoglobulin, morphine, and sodium valproate. Careful formulation of dilute TI solutions of these drugs may allow safe and effective subcutaneous tumescent infiltration.

Pharmacologic properties that contribute to cutaneous and subcutaneous tissue toxicity include pH, osmolality, diluent, vasoactive properties, and inactive ingredients. With appropriate formulation of the subcutaneous TI solution these drugs can be injected (delivered) subcutaneously in a manner that is safe, comfortable and uniquely effective.

The possible safe and effective subcutaneous delivery of these drugs is unanticipated. The therapeutic advantage of TI (local and simultaneous systemic delivery) is not obvious. TI provides therapeutic subcutaneous concentrations that are not achievable by any other mode of delivery and TI simultaneously provides therapeutic serum concentrations with a pharmacokinetic concentration-time profile resembling a slow continuous IV infusion. No previously described mode of drug delivery can achieve these results.

Tumescent Lidocaine Delivery

The standard tumescent solution consisting of 1 gm of lidocaine, 1 mg of epinephrine and 10 mEq of sodium bicarbonate in a liter of 0.9% physiologic saline is the functional equivalent to a drug delivery vehicle. The epinephrine component of the tumescent solution determines the degree of local subcutaneous vasoconstriction. Reducing the epinephrine concentration in the tumescent solution attenuates pharmacologic capillary vasoconstriction. Infiltration of a tumescent solution with no epinephrine and a trace of lidocaine produce capillary vasodilation. The tumescent (augmented) interstitial pressure also accelerates transcapillary fluid absorption into the systemic circulation and similarly accelerates systemic drug delivery.

The lidocaine component of a tumescent solution has local anesthetic, local antibacterial and systemic anti-inflammatory effects. Locally, dilute lidocaine eliminates the pain associated with the subcutaneous injection of other drugs and provides rapid onset of prolonged widespread surgical local anesthesia. The continuous systemic absorption of 28 mg/kg of tumescent lidocaine conveniently provides safe predictable therapeutic serum lidocaine concentrations (1 µg/ml to 2 µg/ml) for 12 hours or more. Epidural lidocaine may reduce bacterial growth at a surgical site (Igarashi T, Suzuki T, Mori K, Inoue K, Seki H, Yamada T, Kosugi S, Minamishima S, Katori N, Sano F, Abe T, Morisaki H. The Effects of Epidural Anesthesia on Growth of *Escherichia coli* at Pseudosurgical Site: The Roles of the Lipocalin-2 Pathway. Anesth Analg. 2015; 121: 81-89).

Subcutaneous tumescent lidocaine, at concentrations far exceeding the therapeutic serum concentrations of lidocaine following IV delivery, is anti-bacterial and provides pre-emptive, inter-operative and post-operative analgesia. Lidocaine local anesthesia reduces post-operative narcotic use with earlier return of normal bowel function and earlier postoperative ambulation (Sakuragi T, Ishino H, Dan K. Bactericidal activity of clinically used local anesthetics on *Staphylococcus aureus*. Reg Anesth. 21: 239-42, 1996; Parr A M, Zoutman D E, Davidson J S. Antimicrobial activity of lidocaine against bacteria associated with nosocomial wound infection. Ann Plast Surg. 43: 239-45, 1999; Igarashi T, Suzuki T, Mori K, Inoue K, Seki H, Yamada T, Kosugi S, Minamishima S, Katori N, Sano F, Abe T, Morisaki H. The Effects of Epidural Anesthesia on Growth of *Escherichia coli* at Pseudosurgical Site: The Roles of the Lipocalin-2 Pathway. Anesth Analg. 2015; 121: 81-89; De Oliveira G S Jr, Fitzgerald P, Streicher L F, Marcus R J, McCarthy R J. Systemic lidocaine to improve postoperative quality of recovery after ambulatory laparoscopic surgery. Anesth Analg. 2012; 115: 262-67; Fierheller E E, Caulkett N A, Haley D B, Florence D, Doepel L. Onset, duration and efficacy of four methods of local anesthesia of the horn bud in calves. Vet Anaesth Analg. 2012; 39: 431-5; Katz J, Clarke H, Seltzer Z. Preventive analgesia: quo vadimus? Anesth Analg 2011; 113: 1242-1253; Rosaeg O P, Bell M, Cicutti N J, Dennehy K C, Lui A C, Krepski B. Pre-incision infiltration with lidocaine reduces pain and opioid consumption after reduction mammoplasty. Reg Anesth Pain Med. 1998; 23: 575-579; Cui W, Li Y, Li S, Wang R, Li J. Systemic administration of lidocaine reduces morphine requirements and postoperative pain of patients undergoing thoracic surgery after propofol-remifentanil-based anaesthesia. Eur J Anaesthesiol. 2010; 27: 41-46).

Tumescent infiltration of lidocaine may inhibit systemic inflammatory responses to trauma and the bacterial infection. Lidocaine down regulates many inflammatory mediators and has significant pharmacologic anti-inflammatory properties (Hatakeyama N, Matsuda N. Alert cell strategy: mechanisms of inflammatory response and organ protection. Curr Pharm Des 2014; 20:5766-78; Berger C, Rossaint J, Van Aken H, Westphal M, Hahnenkamp K, Zarbock A. Lidocaine reduces neutrophil recruitment by abolishing chemokine-induced arrest and transendothelial migration in septic patients. J Immunol. 2014; 192: 367-76; Wang H L, Liu Y Y, Yan H D, Wang X S, Huang R, Lei W F. Intraoperative systemic lidocaine inhibits the expression of HMGB1 in patients undergoing radical hysterectomy. Int J Clin Exp Med, 2014; 7: 3398-403; Wang H L, Zhang W H, Lei W F, Zhou C Q, Ye T. The inhibitory effect of lidocaine on the release of high mobility group box 1 in lipopolysaccharide-stimulated macrophages. Anesth Analg. 2011:112: 839-44; Van Der Wal S, Vaneker M, Steegers M, Van Berkum B, Kox M, Van Der Laak J, Van Der Hoeven J, Vissers K, Scheffer G J. Lidocaine increases the anti-inflammatory cytokine IL-10 following mechanical ventilation in healthy mice. Acta Anaesthesiol Scand. 2015; 59: 47-55; Huang G S, Lin T C, Wang J Y, Ku C H, Ho S T, Li C Y. Lidocaine priming reduces ADP-induced P-selectin expression and platelet-leukocyte aggregation. Acta Anaesthesiol Taiwan. 2009; 47: 56-61; Lee P Y, Tsai P S, Huang Y H, Huang C J. Inhibition of toll-like receptor-4, nuclear factor-kappaB and mitogen-activated protein kinase by lignocaine may involve voltage-sensitive sodium channels. Clin Exp Pharmacol Physiol. 2008; 35: 1052-8; Kiyonari Y, Nishina K, Mikawa K, Maekawa N, Obara H. Lidocaine attenuates acute lung injury induced by a combination of phospholipase A2 and trypsin. Crit Care Med. 2000; 28: 484-489; Nishina K, Mikawa K, Takao Y, Shiga M, Maekawa N, Obara H. Intravenous lidocaine attenuates acute lung injury induced by hydrochloric acid aspiration in rabbits. Anesthesiology. 1998; 88: 1300-9; Benlier E, Eskiocak S, Puyan F O, Sikar E Y, Kandulu H, Omurlu I K, Top H, Aygit A C. Effect of lidocaine on reducing injury in a rat electrical burn model. Ann Plast Surg. 2012; 69: 152-6; Liu J, Zhang H, Qi Z, Zheng X. Lidocaine protects against renal and hepatic dysfunction in septic rats via downregulation of Toll-like receptor 4. Mol Med Rep. 2014; 9: 118-24; Peiró J R, Barnabé P A, Cadioli F A, Cunha F Q, Lima V M, Mendonça V H, Santana A E, Malheiros E B, Perri S H, Valadão CA. Effects of lidocaine infusion during experimental endotoxemia in horses. J Vet Intern Med. 2010; 24: 940-8; Gallos G, Jones D R, Nasr S H, Emala C W, Lee H T. Local anesthetics reduce mortality and protect against renal and hepatic dysfunction in murine septic peritonitis. Anesthesiology, 2004; 101: 902-11; Schmidt W, Schmidt H, Bauer H, Gebhard M M, Martin E. Influence of lidocaine on endotoxin-induced leukocyte-endothelial cell adhesion and macromolecular leakage in vivo. Anesthesiology. 1997; 87: 617-24). Infiltration of traumatized or infected tissue with a tumescent solution of lidocaine and antibiotics engulfs large volumes of damaged tissue and prevents the spread of locally generated inflammatory cytokines, chemokines, histones and pathogens and blunts systemic inflammatory responses. Tumescent lidocaine inhibits platelet function, limits platelet leukocyte aggregation, limits activated-platelet induced inflammation and may reduce the risk of thromboembolism. Tumescent lidocaine decreases blood viscosity, resulting in increased oxygenation of local and systemic tissues.

TI Antibiotic Delivery

Despite I V antibiotic prophylaxis, surgical site infections (SSIs) remain a significant problem (Watanabe M, Suzuki, H, Nomura S, Maejima K, Chihara N, Komine O, Mizutani S, Yoshino M, Uchida E. Risk factors for surgical site infection in emergency colorectal surgery: a retrospective analysis. Surg Infect (Larchmt) 2014; 15: 256-61; Smith R L, Bohl J K, McElearney S T, Friel C M, Barclay M M, Sawyer R G, Foley E F. Wound infection after elective colorectal resection. Ann Surg. 2004; 239: 599-605; Bot J, Piessen G, Robb W B, Roger V, Mariette C. Advanced tumor stage is an independent risk factor of postoperative infectious complications after colorectal surgery: arguments from a case-matched series. Dis Colon Rectum. 2013; 56: 568-76). SSIs devastate patients and are a tremendous financial burden on health care systems (de Lissovoy G, Fraeman K, Hutchins V, Murphy D, Song D, Vaughn B B. Surgical site infection: incidence and impact on hospital utilization and treatment costs. Am J Infect Control, 2009; 37: 387-97; Vogel T R, Dombrovskiy V Y, Lowry S F. Trends in postoperative sepsis: are we improving outcomes? Surg Infect 2009; 10: 71-8; Fukuda N, Wada J, Niki M, Sugiyama Y, Mushiake H. Factors predicting mortality in emergency abdominal surgery in the elderly. World J Emerg Surg 2012; 7: 12; Broex E C, van Asselt A D, Bruggemann C A, van Tiel F H. Surgical site infections: how high are the costs? J Hosp Infect 2009; 72: 193-201). In recent years, major efforts to reduce SSIs have only achieved incremental improvements (Alexander J W, Solomkin J S, Edwards M J. Updated recommendations for control of surgical site infections. Ann Surg. 2011; 253: 1082-93; Larochelle M, Hyman N, Gruppi L, Osler T. Diminishing surgical site infections after colorectal surgery with surgical care improvement project: is it time to move on? Dis Colon Rectum. 2011; 54: 394-400; Serra-Aracil X, García-Domingo M I, Parés D, Espin-Basany E, Biondo S, Guirao X, Orrego C, Sitges-Serra A. Surgical site infection in elective operations for colorectal cancer after the application of preventive measures. Arch Surg. 2011; 146: 606-12; Owens P L, Barrett M L, Raetzman S, Maggard-Gibbons M, Steiner C A. Surgical site infections following ambulatory surgical procedures. JAMA 2014; 311: 709-716).

TI antimicrobial delivery is the direct subcutaneous infiltration of antimicrobial drug(s) dissolved in a large volume of a tumescent lidocaine anesthesia (TLA) solution.

The standard TLA solution consists lidocaine (1 gm) and epinephrine (1 mg) and sodium bicarbonate (10 mEq) in a 1000 ml bag of physiologic saline. In other words, a TLA solution consists of at least a 10-fold dilution of commercial 1% lidocaine with epinephrine 1:100,000 plus sodium bicarbonate (1 mEq/ml) in a liter of normal saline. Wide spread subcutaneous vasoconstriction resulting from a large volume of dilute tumescent epinephrine produces prolonged local anesthesia and reduced surgical blood loss (Klein J A. Tumescent technique for local anesthesia improves safety in large volume liposuction. Plast Reconstr Surg 1993; 92:1085-1098). Sodium bicarbonate neutralizes the acidic pH of commercial solutions of lidocaine with epinephrine, thereby reducing the stinging-pain associated with subcutaneous infiltration (McKay W, Morris R, Mushlin P. Sodium Bicarbonate Attenuates Pain on Skin Infiltration with Lidocaine, with or without Epinephrine. Anesth Analg 1987, 66:572-57).

In our research we studied TI antibiotic delivery of cefazolin and metronidazole. Cefazolin and metronidazole were selected because they are water soluble, safe, well tolerated in subcutaneous tissue, effective and economical for prevention of SSIs (Meyer N L, Hosier K V, Scott K, Lipscomb G H. Cefazolin versus cefazolin plus metronidazole for antibiotic prophylaxis at cesarean section. South Med J. 2003; 96: 992-5; Morris W T, Innes D B, Richardson R A, Lee A J, Ellis-Pegler R B. The prevention of post-appendectomy sepsis by metronidazole and cefazolin: a controlled double blind trial. Aust N Z J Surg. 1980; 50: 429-33; Brown G R, Clarke A M. Therapeutic interchange of cefazolin with metronidazole for cefoxitin. Am J Hosp Pharm. 1992; 49: 1946-50; Hospenthal D R, Murray C K, Andersen R C, et al. Guidelines for the prevention of infections associated with combat-related injuries: 2011 update: endorsed by the Infectious Diseases Society of America and the Surgical Infection Society. J Trauma. 2011; 71 (2 Suppl 2): S210-34; Cho M J, Kurtz R R, Lewis C, Machkovech S M, Houser D J. Metronidazole phosphate—a water-soluble prodrug for parenteral solutions of metronidazole. J Pharm Sci. 1982; 71: 410-4). Cefazolin and metronidazole, when mixed together in a saline solution for IV delivery, are both chemically stable for at least 72 hours at 8° C. (Rivers T E, McBride H A, Trang J M. Stability of cefazolin sodium and metronidazole at 8 degrees C. for use as an i.v. admixture. J Parenter Sci Technol. 1993; 47: 135-7). Subcutaneous infiltration of cefazolin and metronidazole is considered off-label by the US Food and Drug Administration (FDA).

In our clinical research, there were no adverse local or systemic effects of dilute cefazolin, metronidazole, lidocaine or epinephrine after subcutaneous tumescent infiltration. Subcutaneous delivery of cefazolin or metronidazole is considered "off-label." Our data and published reports suggest subcutaneous cefazolin or metronidazole represent a non-significant risk of harm to patients (Bhargava P, Mehrotra N, Kumar A. Wound infection after metronidazole infiltration. Trop Doct. 2006; 36: 37-8, Shubing W, Litian Z. Preventing infection of the incision after appendectomy by using metronidazole preoperatively to infiltrate tissues at the incision. Am J Surg. 1997; 174: 422-4; Quendt J, Blank I, Seidel W. Peritoneal and subcutaneous administration of cefazolin as perioperative antibiotic prophylaxis in colorectal operations. Prospective randomized comparative study of 200 patients. Langenbecks Arch Chir. 1996; 381: 318-22; el-Sefi T A, el-Awady H M, Shehata M I, al-Hindi M A. Systemic plus local metronidazole and cephazolin in complicated appendicitis: a prospective controlled trial. J R Coll Surg Edinb. 1989; 34: 13-6). Subcutaneous antibiotic delivery for systemic effect is commonly used for palliative therapy (Azevedo E F, Barbosa L A, DeBortoli Cassiani S H. Administration of antibiotics subcutaneously: an integrative literature review. Acta Paul Enferm. 2012; 25: 817-22; Robelet A, Caruba T, Corvol A, Bégué D, Gisselbrecht M, Saint-Jean O, Prognon P, Sabatier B. Antibiotiques par voie sous-cutanée chezla personne âgée. Presse Med. 2009; 38: 366-76; Frasca D, Marchand S, Petitpas F, Dahyot-Fizelier C, Couet W, Mimoz O. Pharmacokinetics of ertapenem following intravenous and subcutaneous infusions in patients. Antimicrob Agents Chemother. 2010; 54: 924-6; Walker P, Neuhauser M N, Tam V H, Willey J S, Palmer J L, Bruera E, Prince R A. Subcutaneous administration of cefepime. Pain Symptom Manage. 2005; 30: 170-4; Melin-Coviaux F, Hary L, Hurtel A S, Andrejak M, Grumbach Y. Etude pharmaco-clinique comparative de la ceftriaxone par voie sous-cutanee et intraveineuse chez la personne agee. Revue Geriatr. 2000; 25(5): 337-37; Bricaire F, Castaing J L, Pocidalo J J, Vilde J L. Etude de la pharmacocinétique et de la tolérance de la ceftriaxone administré par voie sous-cutané. Pathol Biol (Paris). 1998; 36 (5 Pt 2): 702-5; Borner K, Lode H, Hampel B. Pfeuffer M, Koeppe P. Comparative pharmacokinetics of ceftriaxone after subcutaneous and intravenous administration. Chemotherapy 1985; 31: 237-45; Gauthier D, Schambach S, Crouzet J, Sirvain S, Fraisse T. Subcutaneous and intravenous ceftriaxone administration in patients more than 75 years of age. Med Mal Infect. 2014; 44: 275-80; Barbot A, Venisse N, Rayeh F, Bouquet S, Debaene B, Mimoz O. Pharmacokinetics and pharmacodynamics of sequential intravenous and subcutaneous teicoplanin in critically ill patients without vasopressors. Intensive Care Med. 2003; 29: 1528-34; Champoux N, Du Souich P, Ravaoarinoro M, Phaneuf D, Latour J, Cusson J R. Single-dose pharmacokinetics of ampicillin and tobramycin administered by hypodermoclysis in young and older healthy volunteers. Br J Clin Pharmacol. 1996; 42: 325-31).

One of the most remarkable aspects of Tumescent Infiltration (TI) drug delivery is the slow rate of systemic absorption of antibiotic following TI produces a serum antibiotic concentrations-time profile resembling a slow constant IV infusion.

A significant finding of our research was that two drugs with remarkably dissimilar pharmacokinetic profiles in serum after IVAD have virtually identical pharmacokinetic profiles in tumescent interstitial fluid (TISF) after tumescent infiltration.

When 500 mg of cefazolin and 500 mg of metronidazole were delivered simultaneously in a single IV bag the resulting concentration-time profiles were dramatically different, as one would expect for two drugs with distinctly different volumes of distribution, clearance rates and protein binding properties.

When 500 mg of cefazolin and 500 mg of metronidazole in single bag of (1210 ml) of tumescent solution were delivered by TI, the resulting concentrations-time profiles of these antibiotics in subcutaneous tumescent interstitial fluid were identical, with identical peak concentrations in the tumescent interstitial fluid.

Following TI delivery of cefazolin and metronidazole, their slow steady systemic absorption with zero order kinetics resulted in a surprising serum concentration-time profile that resembled a slow continuous IV infusion.

Remarkably, the serum concentrations (at each time point after TI infiltration) increased with increasing total mg dose of antibiotic in the tumescent solution. Similarly, the serum concentrations (at each time point after TI infiltration) increased with increasing mg/L concentration of antibiotic in the tumescent solution.

This unexpected finding suggests that one can judiciously formulate a tumescent solution with an optimal total mg dose and an optimal mg/L concentration of a drug and thereby achieve a prolonged optimal concentration-time profile in subcutaneous tumescent interstitial fluid and an optimal concentration-time profile in serum.

An important corollary to this pharmacokinetic discovery is that dissimilar drugs, for example lidocaine, antibiotics, antiviral, antifungal, or anti-tumor drugs may demonstrate nearly identical subcutaneous concentration-time profiles in TISF after tumescent delivery.

Tumescent infiltration can safely provide prolonged relatively high drug concentration in subcutaneous TISF. In many cases, achieving similar subcutaneous drug concentrations solely by IV infusion may be impossible or pose a significant risk of systemic toxicity and harm to the patient. For example, the aminoglycoside antibiotics gentamicin and amikacin are associated with dose and concentration related potential ototoxicity and nephrotoxicity. Achieving prolonged high subcutaneous concentrations by means of IV delivery requires high-prolonged IV dosages with the inherent risk to hearing (inner ear) and kidney damage. However, slow continuous tumescent delivery of very dilute tumescent gentamicin or amikacin results in reduced dose requirements with adequate therapeutic concentrations in subcutaneous tissue together with slow systemic absorption and remarkably low serum concentrations, and thus reduced risk of systemic toxicity.

In some embodiments, TI of antibiotics for prevention of surgical site infection (SSI) is optimally delivered with the use of either HK Monty stainless steel re-usable cannulas or HK SubQKath disposable catheters (U.S. Pat. Nos. 7,572,613; 7,914,504; 8,105,310; 8,167,866; 8,246,587; 8,512,292; 8,529,541) and tumescent peristaltic infiltration pump and tubing.

The Tumescent Technique

As described in further detail below, the present embodiments take advantage of the tumescent technique in order to provide intermittent or continuous, brief or prolonged multi-liter infiltration of local anesthetic, physiologic fluid, antibiotics or other therapeutic solution with a significant decrease in patient discomfort due to the elimination of the piston-like in and out motion of the cannula. Once the cannula is positioned in place, there is no need to repeatedly move the cannula in and out through the tissue in order to deliver the fluid to a wide area. Using the tumescent technique and stainless steel versions of several embodiments, the time needed in order to complete the infiltration of a targeted anatomic area is reduced to nearly half of the time required when using traditional cannula. The device and method of the present embodiments can use multiple (e.g., two or more) infiltration cannula simultaneously. While one cannula is actively dispersing tumescent fluid into the subcutaneous tissue, the surgeon can reposition a second infiltration cannula. This allows the infiltration process to proceed without interruption, whereas prior art techniques of infiltration must be ceased each time the cannula is withdrawn from the skin and re-inserted into another direction.

The flexible plastic cannula version of the present embodiments provides a means for relatively rapid fluid resuscitation in emergency situations such as when establishing an intravenous (IV) access is not feasible. A large volume of a tumescent crystalloid solution to treat intravascular fluid deficit may be delivered subcutaneously when an intravascular (IV) line cannot be started for fluid replacement. (e.g., remote area, obese patient, burn/trauma victim, unavailable trained medical professional, etc.). As a further embodiment, rapid systemic absorption of physiologic saline can be achieved by adding a vasodilator drug to saline and using the tumescent technique to deliver the solution into subcutaneous tissue. For example, in the setting of overwhelming mass casualties where there is no hope or expectation of trained clinical personnel being available, the ability of untrained first-responders to provide immediate fluid resuscitation could save many lives. When a disaster causes an overwhelming number of trauma or burn victims, or when a cholera epidemic leaves victims with life-threatening dysentery and dehydration, it is unlikely that there will be sufficient trained personnel to start an IV line for IV fluid resuscitation. In such a setting, anyone (e.g., adult of average intelligence with minimal clinical training), perhaps even a victim himself, could simply insert one or more disposable plastic infiltration cannula directly through the skin on the thigh(s) and into subcutaneous tissue and attach an IV bag and then allow the force of gravity to propel the fluid into the subcutaneous space in a tumescent fashion. The resulting systemic absorption and redistribution into the intracellular and intravascular compartments could be life-saving. This emergency resuscitation procedure can involve the combination of 1) the plastic-catheter embodiment and 2) absorption kinetics of tumescent fluid delivered to subcutaneous tissue.

The flexible cannula may also have important applications in treating a wounded soldier in night-time combat conditions when establishing an IV access in total darkness is nearly impossible or using a flashlight might attract enemy fire. The flexible cannula may similarly have important applications in other areas of use such as treating mass-casualty victims suffering hypovolemia as a result of epidemic infections, biologic warfare, or trauma such as explosions, burns or radiation exposure. The flexible cannula similarly has applications in surgical patients wherein the surgeon can provide localized pre-operative preemptive analgesia and simultaneously provide tumescent delivery of a prophylactic dose of an antibiotic aimed precisely at tissues targeted for surgical intervention.

The tumescent technique was discovered by Jeffrey Alan Klein, M.D. (the present applicant) in 1985. Dr. Klein first published a description of the tumescent technique in 1987 when he described the use of dilute lidocaine and epinephrine to permit liposuction totally by local anesthesia. The technique for tumescent local anesthesia is well known in dermatologic and plastic surgery literature. A detailed description of the tumescent technique has not been published in anesthesiology literature, and therefore, the unique benefits of the tumescent technique are not recognized by anesthesiologists.

In several embodiments, the tumescent technique comprises a drug delivery system that takes advantage of a recently discovered reservoir effect of injecting a relatively large volume of relatively dilute solution of a drug into the subcutaneous tissue.

Several embodiments take advantage of the tumescent reservoir phenomenon for one of its important applications. After a large volume (e.g., multi liter) of fluid containing dilute epinephrine is injected into subcutaneous tissue, the epinephrine-induced vasoconstriction dramatically slows the systemic absorption of the fluid and minimizes surgical blood loss. In effect, this large volume of subcutaneous fluid behaves in a fashion that is analogous to the behavior of a slow-release tablet in the stomach after oral ingestion. Although there is a relatively large total amount of drug in the patient's body, the drug is isolated from the systemic circulation because only the drug on the outer boundary of the mass of drug is the available for absorption, whereas the portion of the drug located within the central portion of the mass of fluid is virtually isolated from the systemic circulation by virtue of profound capillary vasoconstriction. In contrast, when the tumescent fluid does not contain epinephrine there is no clinically significant vasoconstriction after tumescent infiltration, and the tumescent fluid is absorbed relatively rapidly. This has important clinical applications in situations where patients are hypovolemic or dehydrated and unable to be given fluids by mouth or intravenously. The tumescent technique permits rapid systemic hydration by direct subcutaneous or intramuscular injection of a large volume of fluid through a multi-fenestrated infiltration cannula described in this invention.

A technique known as hypodermoclysis involves the slow and continuous infiltration of fluid subcutaneously using a type of steel hypodermic needle, known as a butterfly needle, having a single distal aperture in order to provide fluid to patients who cannot be given fluids by mouth and for whom an IV access cannot be established, such as in the treatment of infants, or cancer patients. The technique of hypodermoclysis is typically used to deliver relatively small volumes of fluid, for example an adult might receive 70 ml per hour. At this small hourly volume hypodermoclysis is not an efficient method for the rapid systemic delivery of fluid in emergency situations that might require two to four liters per hour. The reason is that when using a cannula with only a single distal aperture, the local interstitial fluid pressure increases rapidly immediately adjacent to the single aperture as fluid infiltrates locally, which in turn dramatically slows the rate of subsequent fluid flow into the area. In contrast, the multiple apertures formed along the length of the cannula as described in the present invention, distribute the fluid throughout a much larger volume tissue before there can be a sufficient increase in the interstitial fluid to decrease the rate of additional infiltration. Also, the amount of pain is reduced because the rate of fluid flow through each of the apertures is less than the rate of fluid flow through the single aperture at the distal end. Furthermore, it is common practice to infiltrate the tumescent fluid into the subcutaneous space under augmented external pressure provided by an external peristaltic pump specifically designed for tumescent infiltration. By way of example and not limitation, a preferred suitable peristaltic infiltration pump is described in pending U.S. patent application Ser. No. 10/811,733, filed Mar. 29, 2004, entitled INFILTRATION PUMP HAVING INSULATED ROLLERS AND PROGRAMMABLE FOOT PEDAL, the disclosure of which is expressly incorporated herein by reference.

The peristaltic pump provides a sufficient degree of pressure to easily overcome the localized increased interstitial pressure associated with the local effects of a tumescent infiltration. On the other hand, in situations where a peristaltic infiltration pump is not available, such as in remote locations without any available electrical power, the present invention still permits relatively rapid tumescent infiltration by virtue of the multiple holes distributed along the length of the flexible cannula. Furthermore, external hydrostatic pressure can be applied to the fluid flowing into the flexible cannula from the fluid reservoir by means of gravitational force derived from elevating the reservoir one to two or more meters above the patient. When using gravity to augment the flow of tumescent fluid, the infiltration process can be continuous or intermittent. In exemplary embodiments, the intermittent injections are administered at intervals ranging from every few minutes to eight to twelve hours or more.

With the tumescent technique for local anesthesia, a large volume of dilute solution of local anesthesia and epinephrine is injected into the subcutaneous space resulting in a large bolus (or interstitial reservoir) of solution. The profound vasoconstrictive effect (shrinking of the capillaries) caused by the dilute epinephrine, produces a dramatic delay in the systemic absorption of the local anesthetic, which prolongs the anesthetic effects of tumescent anesthesia for eight to sixteen times longer than traditional techniques.

Figure 2:
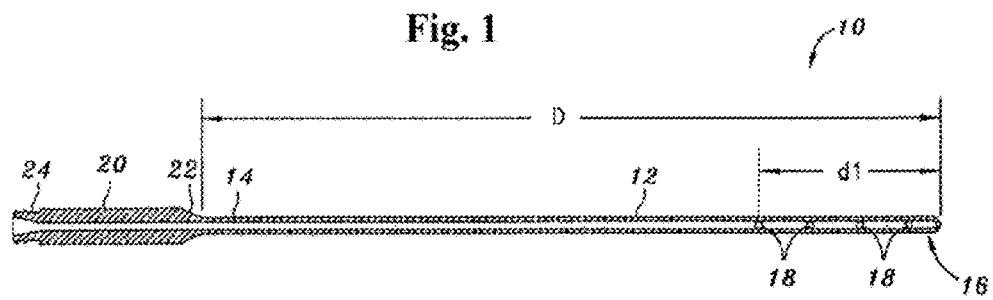
FIG. 2 is a section view of the infiltration cannula shown in FIG. 1.
Figure 3:
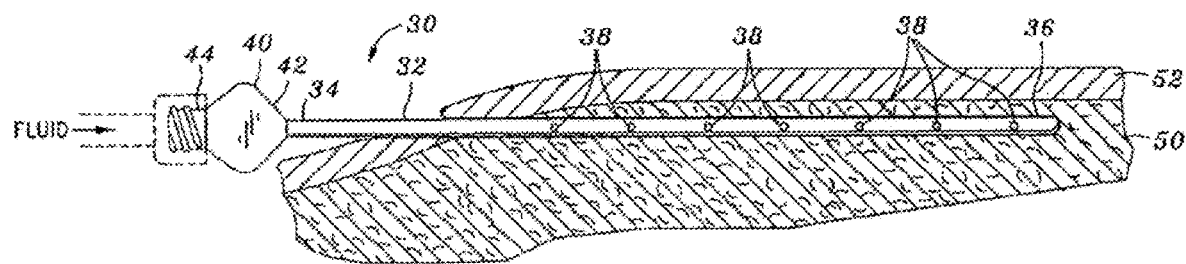
FIG. 3 is a side elevation view of a plastic infiltration cannula with a closed tip shown inserted in subcutaneous tissue shown in partial cross section.
Figure 4:
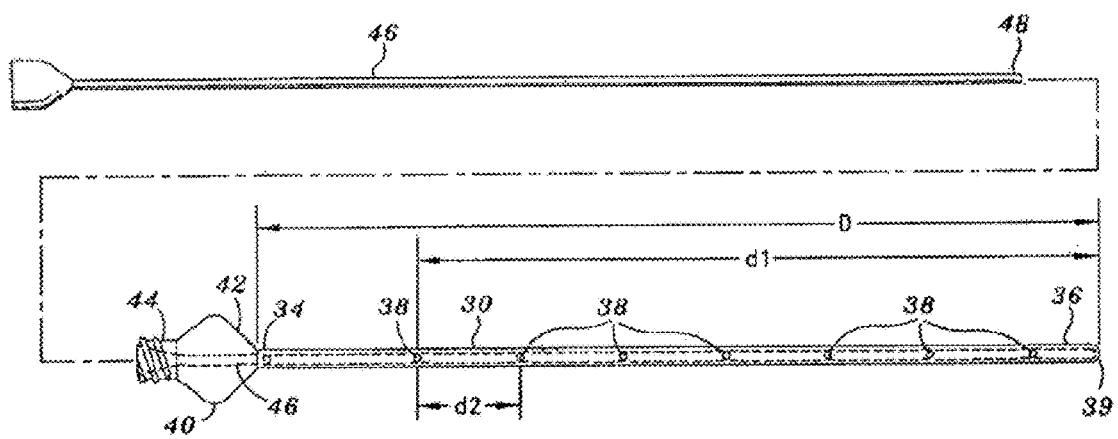
FIG. 4 is an exploded view of the infiltration cannula shown in FIG. 3 with a closed end.
Figure 6:
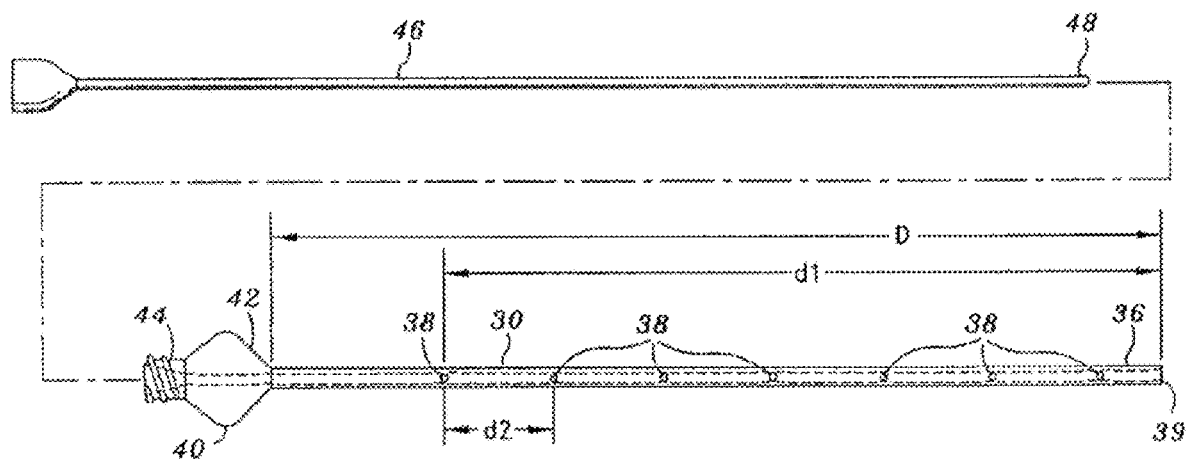
FIG. 6 is an exploded side elevation view of a plastic infiltration cannula through which a stylet can be inserted with an open end.

Referring now to the drawings wherein the showings are for purposes of illustrating preferred embodiments of the present invention only, and not for purposes of limiting the same, FIGS. 1 and 2 illustrate a stainless steel (reusable) infiltration cannula 10 and FIGS. 3-4 and 6 illustrate a (single use) plastic infiltration cannula 30. The cannula 10, 30 can be inserted under the skin 52 and into the subcutaneous tissue 50 and tumescent local anesthesia can be infiltrated either continuously until the clinical goal is achieved or intermittently (by way of example and not limitation, once every eight to twelve hours).

Stainless steel infiltration cannula 10, such as the one shown in FIGS. 1 and 2, are formed having precision high quality and are preferably reusable. These cannula can be used to provide tumescent local anesthesia for surgical procedures, such as liposuction, which require tumescent local anesthesia over a relatively large area.

The cannula 10 includes a tubular needle portion 12 which has a proximal end 14 and a distal end 16. The proximal end 14 of the tubular needle 12 is attached to a hub 20 that is used by the anesthesiologist or surgeon to grasp and hold the cannula 10 during the infiltration procedure. The hub 20 is connected to the tubular needle 12 at a first end 22 and has a connector 24, such as a luer lock, at an opposing second end. The connector 24 is connected to a fluid source, such as tubing connected to an IV bag. Fluid enters the cannula 10 via the connector 24.

In exemplary embodiments, the tip at the distal end 16 is closed. The local anesthetic is infiltrated into the patient via apertures 18 located proximate the distal end 16 of the tubular needle 12 of the cannula 10. It is contemplated that the apertures 18, 38 and 54 discussed herein may have a helical, spiral, linear or any random or ordered pattern. Also, in exemplary embodiments, the apertures 18 are disposed along the distal end 16 of the cannula 10 in a spiral or helical pattern and are distributed over the distal 33% to 100% of the tubular needle 12 of the cannula 10. For example, if the length of the tubular needle D is 15 cm and the apertures 18 at the distal end 16 cover a length dl of 5 cm, the pattern of apertures of the cannula 10 are preferably distributed over 33% of the tubular needle 12 of the cannula 10. The size of the aperture and density of apertures on the tubular needle is limited by the structural integrity of the cannula. If the apertures 18 are too large or too close together then the cannula may bend or break during use (e.g., routine clinical applications). Prior art cannula wherein the apertures are limited to the distal 25% of the cannula eject the fluid into the subcutaneous tissue at a high rate so as to cause discomfort to the patient. The apertures 18 which are located along a greater length of the cannula compared to prior art cannula allows fluid to flow out of each of the apertures at a slower rate but to achieve a greater amount of fluid flow as an aggregate so as to reduce the amount of discomfort to the patient due to the rate at which fluid flows out of each of the apertures. When tumescent fluid is injected into subcutaneous tissue, tumescent fluid spreads by means of simple bulk-flow through the interstitial gel substance. This process is extremely rapid and unimpeded by fibrous tissue.

The proximal portion 14 of the cannula 10 may be devoid of apertures in order to prevent fluid from leaking out of the cannula insertion site in the skin. Alternatively, if the proximal portion 14 of the cannula has aperture(s), then the hub may be used to prevent fluid from leaking out of the cannula insertion site in the skin in the follower manner. The hub of the infiltration cannula serves as a connector. The distal end of the hub attaches to the cannula, while the proximal end of the hub detachably connects to the plastic tube set which carries tumescent solution to the cannula. With a slight modification, the hub can also assist in reducing or virtually eliminating leakage of tumescent fluid out through the skin incision or adit site. An adit is a small round hole in the skin typically produced by a biopsy punch. The hub 20 may have a conical configuration. The hub 20 may become narrower from the proximal end of the hub to the distal end of the hub. The rate at which the hub 20 becomes narrow may be less than about fifteen degrees with respect to a centerline of the hub. The outer surface of the hub 20 may have a plurality of rounded circular ridges equally spaced apart. The adit may be formed so as to have a diameter which is less than a diameter of the cannula or the outer surface of the hub. To minimize leakage of tumescent fluid out onto the surface of the skin, the cannula may initially be inserted into the adit. The adit is slightly stretched to accommodate the cannula. The cannula may be fully inserted into the subcutaneous tissue of the patient such that the distal end of the hub contacts the adit. The hub may then be pushed into the adit such that the inner diameter of the adit expands and slides over the rounded circular ridges formed on the distal end of the hub. The hub is gently wedged into the adit until there is a snug fit between the infiltration cannula and the adit. Leakage of fluid out of the adit may also be minimized by placing the proximal most aperture on the cannula sufficiently deep within the subcutaneous tissue such that fluid injected from the most proximal hole produces localized interstitial tumescence and a snug fit of the tissue against the cannula. It is also contemplated that the hub has other shapes such as curved, linear, parabolic, or combinations thereof.

Flexible plastic infiltration cannula 30, such as the one shown in FIGS. 3, 4 and 6 are single use cannula and can be used in one of several unique ways. First, an anesthesiologist, surgeon, untrained first responder, or even a victim can insert infiltration cannula 30 with stylet 46 into the subcutaneous tissue 50, remove the stylet 46, then attach IV tubing to the infiltrator and inject tumescent local anesthesia or other tumescent fluid into the targeted area without subsequent repositioning of the infiltration cannula 30. The plastic flexible nature of the tubular needle 32 of the disposable plastic cannula 30 allows the patient to move or change position of the body without risk of injury that might result if a patient moves while a rigid steel cannula is inserted.

In some embodiments, the stylet 46 is formed of a rigid material such as metal, stainless steel, or plastic material. The stylet 46 should be sufficiently rigid so as to guide the tubular needle 32 of the cannula 30 into the subcutaneous tissue 50. The stylet 46 may be solid (see FIG. 4) or hollow (see FIG. 7) through its center. The stylet may either be straight or curved. The plastic cannula 30 can be blunt-tipped with the metal stylet tip 48 covered by the rounded tip 39 of the plastic cannula 30, as shown in FIG. 4. Alternatively, the plastic cannula 30 can be open-ended with the stylet 46 extending a short distance past the end 39 of the plastic cannula 30 as shown in FIG. 6. In the case of the open ended cannula, the stylet 46 can be either blunt-tipped (see FIG. 6; requiring a skin incision to permit insertion into the subcutaneous space), or sharp-tipped (see FIG. 7; permitting the cannula to be inserted directly through the skin and into the subcutaneous space or muscle without requiring a preparatory skin incision). The sharp-tipped stylet 46 can be formed in either a solid (see FIG. 4) or hollow (see FIG. 7) cross-sectional configuration. The utility of a sharp tipped hollow stylet is that it can be inserted directly through the skin and then advanced painlessly through the subcutaneous tissue by slowly injecting local anesthetic solution through the stylet as it is slowly advanced, thereby anesthetizing the tissue in advance of the stylet's tip.

Figure 7:
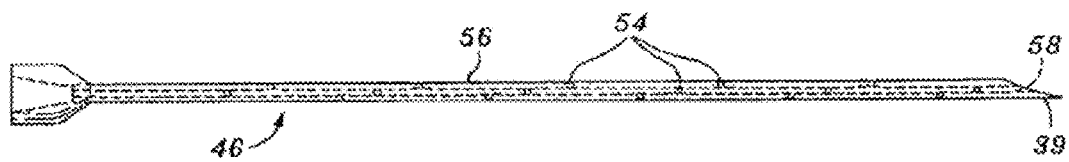
FIG. 7 is a side elevation view of a hollow sharp-tipped stylet with holes located along nearly the entire length of the stylet.

If the stylet 46 is hollow through its center 58, then apertures 54 may be formed along an entire length or along a portion (e.g., about 33% to 100%) of the length of the tubular needle 56 of the stylet 46, as shown in FIG. 7. The hollow stylet 46 (see FIG. 7) may be utilized in a similar fashion as the cannula 10 shown in FIGS. 1 and 2 and described herein. By way of example and not limitation, during use, the tubular needle 56 shown in FIG. 7 may be inserted into the cannula 30. The combined tubular needle 56 and cannula 30 may be inserted through the subcutaneous tissue 50 of the patient. The tubular needle 56 may be removed from the patient and the cannula 30. The tubular needle 56 of the stylet 46 may now be reinserted into the patient at a different site and used as a rigid cannula similar to the cannula 10 discussed in relation to FIGS. 1 and 2.

The stylet 46 shown in FIG. 7 has apertures 54 about the periphery of tubular needle 56 of the stylet 46. The apertures 54 may have a pattern which is dissimilar to the pattern of apertures 38 formed in the tubular needle 32 of the cannula 30. Alternatively, the apertures 54 may have a pattern which is identical to the pattern of apertures 38 formed in the tubular needle 32 of the cannula 30. As a further alternative, some of the apertures 54 may have a pattern which is identical to the pattern of apertures 38 formed in the tubular needle 32 of the cannula 30. Also, some of the apertures 54 may have a pattern which is dissimilar to the pattern of apertures 38 formed in the tubular needle 32 of the cannula 30. During use, the medical professional may insert the stylet 46 (see FIG. 7) with apertures 54 into the cannula 30. The apertures 54 of the stylet 46 may be aligned or misaligned to the apertures 38 of the tubular needle by turning the stylet 46 within the cannula 30. The stylet 46 may have a hub with a similar configuration as hub 40. The hub of the stylet 46 may also be wedged into the adit of the patient to minimize or eliminate leakage of fluid, as discussed herein.

The plastic cannula shown in FIGS. 3 and 4 is similar to an IV catheter except the sharp hollow stylet used for the insertion of an IV catheter can be replaced by a solid obturator/stylet 46 that can be either sharp or blunt tipped. Except for the removable stylet 46, the plastic cannula 30 is similar to the stainless steel cannula 10 shown in FIGS. 1 and 2 and described above. The plastic cannula 30 includes a flexible tubular needle 32 having a proximal end 34 and a distal end 36. The distal end has apertures 38 and the proximal end 34 may be devoid of apertures. As stated above, in exemplary embodiments, the pattern of apertures 38 in the cannula 30 are distributed over the distal 33% to 100% (see FIG. 4) of the tubular needle 32 of the cannula 30. For example, if the tubular needle 32 of cannula 30 shown in FIGS. 3 and 4 has a length D of 15 cm and the pattern of apertures are distributed over a length dl of 13.5 cm, then the apertures 38 are distributed over 90% of the cannula. As a further example, if the tubular needle 32 of cannula 30 shown in FIGS. 3 and 4 has a length D of 15 cm and the pattern of apertures are distributed over a length dl of 15 cm, then the apertures 38 are distributed over 100% of the cannula. To stop leakage of tumescent fluid out of the adit site, the hub may be wedged into the adit site, as discussed above.

A typical infiltration cannula 10, 30 may have a diameter equivalent to 20, 18, 16 or 14 gauge with small apertures 18, 38 placed every 5 mm along the cannula in a spiral or helical pattern. The infiltration cannula 10, 30 may be 20-14 cm in length. A typical infiltration cannula 10, 30 is 15 cm or 20 cm in length. It will be appreciated that the dimensions used herein are exemplary and that the cannula dimensions, range of gauge, length range of cannula, relative size shape and pattern of apertures can vary greatly depending upon clinical preference.

The proximal end 34 of the tubular needle 32 shown in FIGS. 3 and 4 is attached to a hub 40 that is used by the anesthesiologist or surgeon to hold the cannula 30 during the infiltration procedure. The hub 40 is connected to the tubular needle 32 at a first end 42 and has a connector 44 at an opposing second end. The connector 44 is connected to a fluid source. As described above and shown in FIG. 4, the stylet 46 can be inserted and removed from the cannula 30.

Infiltration using a plastic infiltration cannula 30, such as the one shown in FIGS. 3 and 4, can be accomplished using an infiltration pump. Alternatively, the force of gravity could be used to push the tumescent fluid into the tissues by hanging a reservoir plastic bag of tumescent local anesthesia (or other dilute drug, such as a chemotherapeutic agent or antibiotics) on an IV pole and connecting bag to the infiltration cannula by an IV line.

Tumescent local anesthesia may be provided to a localized area through which a surgeon plans to make a surgical incision. Tumescent local anesthesia involves the administration of dilute anesthetic solutions into the subcutaneous fat compartment. One example of a tumescent solution used in a liposuction procedure comprises a combination of 500-1000 mg of the anesthetic lidocaine per liter of solvent (typically normal saline or lactated Ringer's solution) along with a vasoconstrictor such as epinephrine to control the rate of lidocaine absorption and reduce bleeding. Bicarbonate may be included to reduce patient discomfort from an otherwise acidic solution. Anti-inflammatory agents may also be included. Once it was shown that this technique was able to safely provide consistent levels of local anesthesia for a large area of the body over a long period of time with little risk of toxicity, it became the standard of care for liposuction. A description of this procedure can be found in Jeffrey A. Klein, *The Tumescent Technique*, DERMATOLOGIC CLINICS, vol. 8, No. 3, pp. 425-437, 1990.

The use of tumescent local anesthesia converted liposuction from a hospital-based procedure requiring general anesthesia and often blood transfusions to an office-based procedure. The tumescent technique has subsequently been adapted for use in a variety of other surgical procedures including hair transplantation, phlebectomy, mastectomy, sentinel node biopsy, and others.

The effects of vasoconstriction, resulting from the epinephrine in the tumescent local anesthetic solution, within the tumesced tissue minimizes surgical bleeding. In a uniquely preemptive fashion, the pre-operative infiltration of tumescent local anesthesia produces prolonged post-operative analgesia and preemptively reduces the risk of surgical wound infections resulting from the bactericidal effects of lidocaine.

Lidocaine is bactericidal in vitro against *S. aureus*, and this effect increases with greater duration of exposure. In a dose-dependent fashion, clinical doses of lidocaine have been shown to inhibit the growth of bacterial pathogens commonly encountered in nosocomial wound infections. A tumescent epinephrine induces profound local vasoconstriction resulting in significantly delayed systemic absorption of a tumescent antimicrobial drug from subcutaneous tissue. In commercially available concentrations, the systemic absorption of an aqueous solution of lidocaine requires approximately 2 to 4 hours. In contrast, the systemic absorption of tumescent lidocaine requires 24 hours or more. Accordingly, a tumescent antibiotic can be expected to remain within the peri-incisional tissue at least 12 times longer than a routine aqueous antibiotic solution and the action would be far more effective. Moreover, a tiny hematoma within an incision may be an isolated avascular space and a potential nidus for an infection. The profound and prolonged vasoconstriction induced by tumescent epinephrine minimizes surgical bleeding and hematoma formation and therefore reduces the risk of surgical site infection. Hypothermia is a major risk factor for postoperative surgical site infection. Mild perioperative hypothermia is common among patients having surgery under general anesthesia. The incidence of SSI was 5.8% in the normothermic (core body temperature 37 degrees C.) group and 18.8% in the hypothermic group (34.4 degrees C.) in a randomized, double blind trial. (Kurtz A, Sessler D I, Lenhardt R. Perioperative normothermia to reduce the incidence of surgical-wound infections and shorten hospitalization. Study of wound infection and temperature group. N Eng J Med 334:1209-15, 1996). Hypothermia also causes delays in moving the patient out of the recovery room. With surgery totally by tumescent local anesthesia there is no evidence of post-operative hypothermia.

Some embodiments relate to infiltration of a tumescent solution comprising an anesthetic component, a vasoconstrictive component, and an antibiotic component. Other embodiments relate to infiltration of a tumescent solution comprising a vasoconstrictive component and an antibiotic component. Other embodiments relate to infiltration of a tumescent solution comprising an anesthetic component and an antibiotic component. Other embodiments relate to infiltration of a tumescent solution comprising an anesthetic component and a vasoconstrictive component. Some embodiments relate to infiltration of a tumescent solution comprising an anesthetic component. Some embodiments relate to infiltration of a tumescent solution comprising a vasoconstrictive component. Some embodiments relate to infiltration of a tumescent solution comprising an antibiotic component. Some embodiments relate to infiltration of a tumescent solution comprising crystalloid fluids/electrolytes.

In one embodiment, infiltration of a tumescent solution comprising lidocaine, epinephrine, and an antibiotic improves surgical site infection prophylaxis. Tumescent infiltration of antibiotics into peri-incisional skin and subcutaneous tissue offers the following advantages: prolonged local tissue concentrations of antibiotics and prolonged systemic delivery of antibiotic to tissues distant from the incision site. The systemic absorption of tumescent lidocaine mimics IV delivery of lidocaine which is known to reduce postoperative pain and hasten postoperative discharge from the hospital. Embodiments of the infiltration cannula discussed herein may be used for tumescent delivery of antimicrobial drugs.

Several embodiments relate to application of the tumescent technique to provide an easily accessible route for systemic administration of crystalloid fluids/electrolytes for systemic hydration or for other types of drug therapy. Potential clinical applications include emergency resuscitation with systemic fluids in situations where insertion of an IV catheter into a vein cannot be readily achieved. Examples of situations where emergency access for intravenous delivery of fluids might not be possible include acute trauma or burn wound in civilian or military situations and very obese patients in which finding an accessible vein for IV access can be difficult even for a physician skilled in performing "IV cut-down" procedures. Embodiments of the infiltration cannula discussed herein may be a valuable adjunct to fluid resuscitation in an ambulance or an emergency room. Another application may be the emergency treatment of dehydration associated with pandemic influenza, prolonged vomiting or diarrhea as a result of chemical warfare or biological warfare (e.g., epidemic cholera among pediatric patients in rural third world settings) or other types of medical emergencies which overwhelm a medical center's capacity to care for incoming victims. A subcutaneous infiltration catheter can easily be introduced by a layman, whereas inserting an IV catheter into a vein of a patient that is severely dehydrated can be difficult even for a skilled physician. Delivery of systemic fluids by subcutaneous infiltration is safer than an IV infusion in a zero gravity situation (for example, the Space Station). The addition of a small amount of capillary vasodilator (e.g., methylnicotinamide) to the subcutaneous fluid can be used to accelerate the systemic absorption of the fluid or drug into the intravascular space. Further applicational uses for the present embodiments are described in co-pending application Ser. No. 10/877,337, filed Jun. 25, 2004, the disclosure of which is expressly incorporated herein by reference.

The continuous systemic drug delivery by tumescence has a similar therapeutic effect to continuous IV infusion but without the inherent expense, difficulties, and risk of an IV infusion. Compared to either oral delivery of a drug (inconsistent absorption from the gastrointestinal tract), or periodic intramuscular (IM) injections of a drug (variable serum concentrations), continuous systemic delivery is preferred in order to achieve prolonged and relatively uniform blood concentrations of the drug. This is especially true in critically ill patients. Tumescent delivery of a drug, placed in a tumescent solution containing epinephrine as a vasoconstrictor, produces prolonged continuous system absorption of the drug over an interval of more than 24 hours. The simplicity and inexpensive equipment required to achieve continuous tumescent systemic drug delivery is clearly an advantage among medically impoverished populations, and in the demanding conditions of battlefield or at the scene of a mass casualty.

Yet another application is related to astronauts and systemic delivery of medication. In particular, the therapeutic options for treating an injured astronaut are limited. The fate of injured airplane pilots, passengers and astronauts are similar in that we presently have virtually no in-flight capability for treating an acute traumatic injury. If a pilot or astronaut survives the immediate effects of an explosion, burn, or decompression injury, or if there is an acute non-traumatic medical illness, it is assumed that the victim must return to terra firma for any significant therapeutic intervention such as providing systemic fluid replacement. The tumescent infiltrator is capable of providing systemic fluid and thus it is successfully solving a problem that has either never before been recognized, or has never before been solved by a simple device and technique.

The present embodiments allow improved emergency medical care for an injured astronaut on-board the International Space Station. Repeated and prolonged extra vehicular activities (EVA) expose astronauts to greater risk of physical trauma injury. Potential injuries to astronauts include decompression injury-induced neurological injury and coma, acute pneumothorax, burns, and radiation injury. Assembly and maintenance of the International Space Station requires an unprecedented number of spacewalks, which expose astronauts to the risk of decompression sickness (DeS). In addition to humanitarian concerns, there is a strong economic incentive to provide on-board care for acute illness or trauma: the only alternative would be to abort an expensive mission and immediately return the victim to earth.

At present, there is no safe and easy means of providing the equivalent of IV fluids to a patient in space. Assuming there is a fellow astronaut with the requisite clinical skill to insert an intravenous (IV) catheter in a weightless environment, there is a problem of zero gravity. Whereas gravity separates air and water into distinct layers, in zero gravity there is a risk of air bubbles from the IV bag entering the IV line and causing intravascular air embolism. Because subcutaneous air is relatively safe, the tumescent infiltration cannula, by allowing effective systemic fluid resuscitation via subcutaneous infiltration, overcomes the above problems, and allows a person without clinical skills to safely provide the equivalent of IV fluids.

The cannula 10, 30 is intended to be inserted far enough through the skin 52 so that all of the apertures 18, 38 are within the fat 50 or muscle of the patient. If the apertures 18, 38 are distributed over about 100% of the cannula, the hub may be wedged into the adit to prevent or minimize leakage of the tumescent fluid out of the adit. Once the cannula 10, 30 is properly positioned, it can remain stationary while the local anesthetic (or other pharmaceutical) solution is injected. Since the cannula remains stationary, the associated pain or discomfort typically caused by the reciprocating in and out movement of prior art cannula is reduced or eliminated. Accordingly, the cannula of the present invention permits infiltration of multi liter volumes of tumescent fluid into the patient in a safe and painless manner.

After one portion of the targeted area has been tumesced, the infiltration is briefly terminated (either by turning off the pump or by clamping the IV tubing) while the cannula 10, 30 is repositioned into another area of the subcutaneous tissue. Typically, the cannula is repositioned at the rate of about once per minute. The infiltration is then restarted with the cannula stationary in its new position. Since the apertures are distributed over the distal 33% to 100% of the cannula, the apertures distribute tumescent fluid into the patient along the entire length of cannula insertion. The cannula does not have to be reciprocated in and out to infiltrate the subcutaneous tissue like prior art cannula. Progressing repeatedly in this fashion, eventually all the fat within a targeted area becomes tumescent and profoundly anesthetized. Such method can obviate the need for general anesthesia or heavy IV sedation in most surgical procedures restricted to the skin and subcutaneous tissue.

The infiltrator 10, 30 can also be used in the traditional mode whereby the cannula 10, 30 is moved through the targeted tissue while the fluid is simultaneously pumped through the cannula 10, 30 and into the subcutaneous tissue 50.

Another unique aspect of the tumescent technique's reservoir effect is that one can conveniently achieve a long, slow, steady absorption of a drug delivered to the subcutaneous space 50 using periodic injections of a tumescent solution. In certain situations, using a slow IV infusion, the alternative technique, can achieve a slow systemic absorption of a drug but may be difficult, require greater clinical expertise, be more expensive, and therefore, less practical than the technique described herein.

Figure 5:
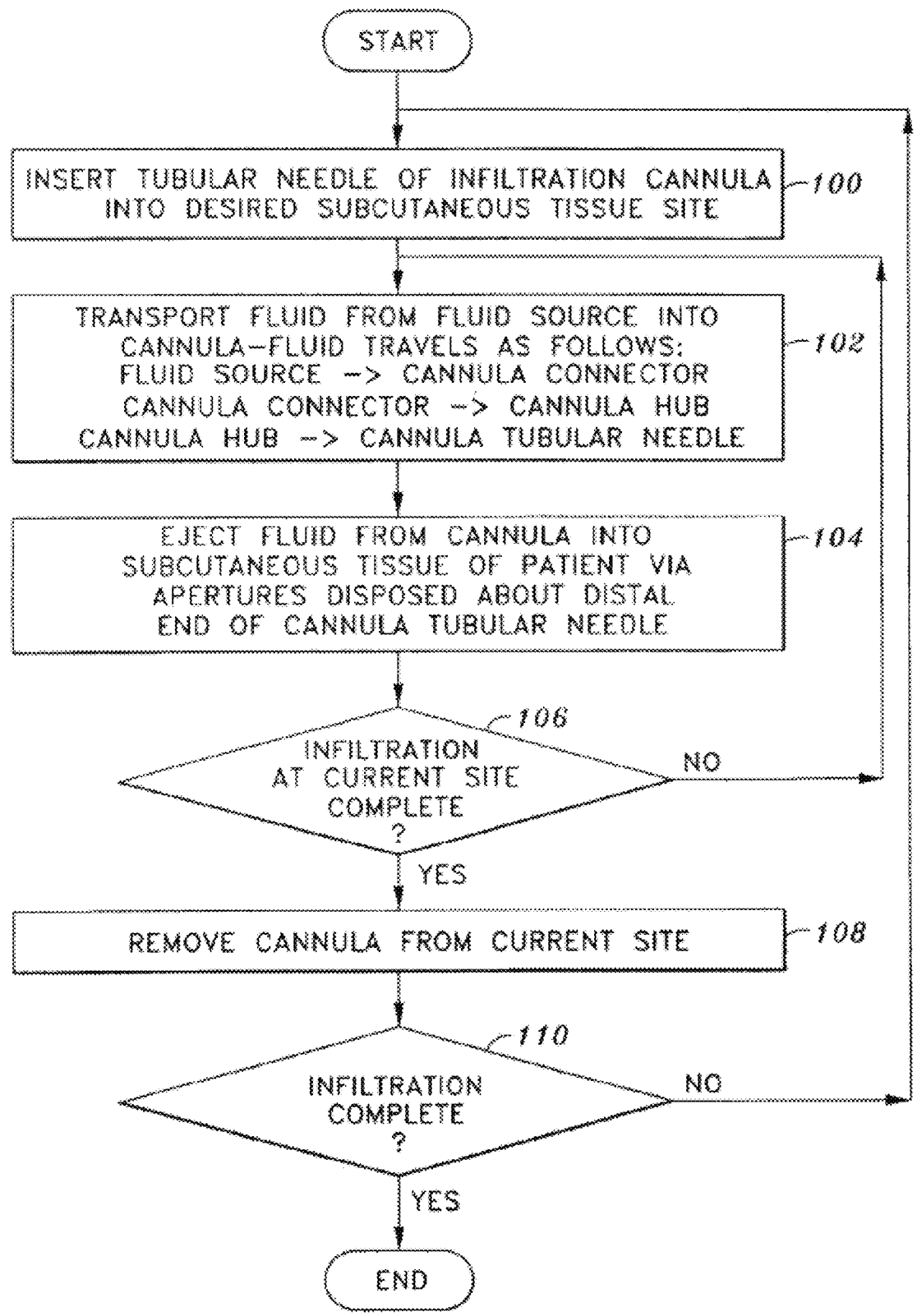
FIG. 5 is a flow diagram illustrating an exemplary procedure for using an infiltration cannula such as the one shown in FIG. 1 or the one shown in FIG. 3.

FIG. 5 is a flow diagram illustrating steps performed in an exemplary infiltration procedure using a cannula 10, 30 such as the one shown in FIGS. 1 and 2 or the one shown in FIGS. 3 and 4, respectively. The procedure begins by inserting the tubular needle 12, 32 of the infiltration cannula 10, 30 into a desired subcutaneous tissue site 50, e.g., via an incision in the patient's skin 52 (block 100). Fluid is then transported from the fluid source (e.g., an IV bag) into the cannula 10, 30 via the connector 24, 44 that is connected to the fluid source. The fluid is transported from the connector 24, 44 through the hub 20, 40 and into the tubular needle 12, 32 (block 102). The fluid is then ejected from the cannula 10, 30 into the subcutaneous tissue 50 of the patient via the apertures 18, 38 at the distal end 16, 36 of the tubular needle 12, 34 of the cannula 10, 30 (block 104).

The fluid is transported (block 102) and ejected (block 104) until infiltration at the current site is completed (yes in decision block 106). Complete infiltration at the current site may take approximately one or two minutes. The fluid can be injected into multiple sites in order to distribute the solution over a greater area.

Infiltration at a particular site may be deemed complete upon emptying of the fluid source or based on the anesthesiologist or surgeon's decision to stop the infiltration at the current site. After one portion of the targeted area has been tumesced, the infiltration can be briefly terminated (either by turning off the pump or by clamping the IV tubing) while the cannula 10, 30 is repositioned into another area of the subcutaneous tissue. The infiltration may then be restarted with the cannula stationary in its new position. If the infiltration at a site is complete (yes in decision block 106), the cannula is removed from the current site (block 108). If the infiltration at the current site is not complete (no in decision block 106), fluid is transported from the fluid source (block 102) and ejected into the subcutaneous tissue (block 104) until infiltration at the site is complete (yes in decision block 106).

If infiltration is complete at the current site (yes in decision block 106) but infiltration is not complete (no in decision block 110); the tubular needle 12, 32 of the infiltration cannula 10, 30 is inserted into a new area of subcutaneous tissue 50. By way of example and not limitation, the tubular needle 12, 32 may be inserted into a new area adjacent the current site. The adjacent site may be partially anesthetized by infiltration of the anesthetic solution at the current site. As such, pain to the patient caused by insertion of the tubular needle 12, 32 is minimized, eliminated or greatly reduced. The process described above is performed until the infiltration process is complete (yes in decision block 110). This process can be continuous or repeated intermittently. It is contemplated that infiltration of up to about 50% of the patient's body may be achieved in the manner described herein.

As described above, multiple infiltration cannula (e.g., can be used at once). Thus, a second or additional cannula can be inserted (block 100) at the same time as a first cannula is being removed (block 108). For example, the second cannula may be inserted parallel to the first cannula and into an area immediately adjacent to the area in which the first cannula is inserted. In this manner, the pain usually associated with the insertion of the cannula into the patient's fat tissue is reduced or eliminated because the first cannula has already at least partially anesthetized the area in which the second cannula is inserted. The second cannula is positioned adjacent the first cannula approximately every one or two minutes. The first cannula may then be removed from the patient's body after the second cannula is inserted. Moreover, the infiltration process need not be interrupted in order to reposition a single cannula. Progressing repeatedly in this fashion, eventually all the fat within a targeted area becomes tumescent and profoundly anesthetized. As such, such method can obviate the need for general anesthesia or heavy IV sedation.

The plastic infiltration cannula shown in FIGS. 3 and 4 may be used by either a lay person or a clinical professional for the delivery of tumescent fluid for either tumescent local anesthesia, tumescent antimicrobial therapy, or emergency delivery of systemic fluids by tumescent infiltration. In an aspect of the cannula 10, 30, it is contemplated that such cannula 10, 30 may be utilized for continuous systemic tumescent delivery of a drug which produces continuous system absorption of the drug over nearly 24 hours in a fashion similar to a continuous IV infusion.

The infiltration cannula 10, 30 discussed herein is a subcutaneous device and not an intravascular device for infiltration of multi-liter volumes of fluid into areas of up to 50% of the total body surface area. For example, the infiltration cannula 10, 30 infiltrates approximately 1,000 times the volume of fluid delivered by the Schwartz device discussed in the background.

Additional modifications and improvements of the present invention may also be apparent to those of ordinary skill in the art. Thus, the particular combination of parts described and illustrated herein is intended to represent only a certain embodiments, and is not intended to serve as a limitation of alternative devices within the spirit and scope of the disclosure.

The tumescent technique may be used to deliver an antimicrobial solution by subcutaneous infiltration. In some embodiments, the antimicrobial solution may comprise an antibiotic. In some embodiments, the antimicrobial solution may also comprise a local anesthetic and/or a vasoconstrictor. Upon delivery of a large volume of solution to the subcutaneous compartment, the surrounding tissue becomes swollen and firm—tumescent. The tumescent technique can be advantageously employed to deliver antibiotics and other agents to a surgical site or the sites of other medical procedures. Some embodiments relate to tumescent antibiotic delivery (TAD) to areas of infection. TAD may be employed prophylactically to prevent an infection or TAD may be employed to treat an existing infection. In certain embodiments, a large volume (≥1 L for example) of dilute antibiotic solution is provided to a site where antibiotic is needed, foregoing the disadvantages of systemic delivery. The antibiotics for tumescent delivery may be provided in a solution of tumescent local anesthetic or without combination with local anesthetic.

Several embodiments relate to a solution comprising an antibiotic component, an anesthetic component, a vasoconstrictor component and a solvent (hereafter referred to as Tumescent Local Antibiotics or TLAnti) to be delivered utilizing the tumescent technique. The relative concentrations of the components of TLAnti may be varied depending upon the level of anesthesia required at a given surgical site, the likelihood of bleeding, risk of infection, or other factors specific to the patient such as age, weight, or liver function.

In some embodiments, the anesthetic component may be comprised of a mixture of 2 or more anesthetics. In some embodiments, the vasoconstrictive component may be comprised of a mixture of 2 or more vasoconstrictors. In some embodiments, the antibiotic component may be comprised of a mixture of 2 or more antibiotics. In some embodiments the anesthetic component may possess both anesthetic and antibiotic properties. In some embodiments, TLAnti may additionally comprise an antiviral and/or an antifungal component. In some embodiments, the TLAnti may comprise additional pharmacological agents, such as, but not limited to, anticonvulsants, stimulants, sedatives, antihistamines, retinoids, corticosteroids, calcium antagonists, chemotherapy agents, prostacyclins, and vasodilators.

In some embodiments, TLAnti comprises a water-soluble antibiotic component. In one embodiment, the water-soluble antibiotic may be Cefazolin. Cefazolin is a first generation cephalosporin that has been sold under the brand names Ancef and Kefzol. This medication is particularly effective against many varieties of gram-positive bacteria that are typically present on the epidermal surface such as *Staphylococcus aureus*. Antibiotic coverage for such ubiquitous organisms is particularly important in surgical procedures because they can enter the surgical site during the procedure and are therefore a likely cause of post-operative infection. In some embodiments, cefazolin is used at a dosage of approximately 250 to 750 mg per liter of solvent. For example, in one embodiment 500 mg of cefazolin is used in 1 liter of TLAnti. In other embodiments cefazolin may be used at a dosage of approximately 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, or 900 mg per liter of solvent.

Persons skilled in the art will recognize that there are a variety of water-soluble antibiotics other than cefazolin that can be used in TLAnti. In some embodiments, TLAnti may comprise a combination of two or more water-soluble antibiotics. In some embodiments, penicillins, cephalosporins, carbapenems, aminoglycosides, sulfonamides, quinolones, macrolides, tetracyclines, lipopetides and oxazolidinones may be used. In one embodiment, metronidazole is used in TLAnti. Suitable antibiotics can be substituted in cases wherein a patient has a known or suspected hypersensitivity to a class of antibiotics, such as cephalosporins, or if the procedure is being performed in an area where resistance to a particular antibiotic is prevalent. In some embodiments, TLAnti may be used to treat an existing infection. In such embodiments, the infective agent may be determined and tested for antibiotic resistance. The antibiotic or combination of antibiotics may be specifically selected based on the resistance profile of the bacterial flora.

Examples of suitable antibiotics include, but are not limited to: amoxicillin, ampicillin, bacampicillin, carbenicillin, cloxacillin, dicloxacillin, flucloxacillin, mezlocillin, nafcillin, oxacillin, penicillin G, penicillin V, Piperacillin, Pivampicillin, Pivmecillinam, Ticarcillin, cefacetrile, cefadroxil, cephalexin, cefaloglycin, cefalonium, cefaloridine, cefalotin, cefamandole, cefapirin, cefatoxin, cefatrizine, cefazaflur, cephalexin, cefazedone, cefazolin, cefepime, cefradine, cefroxadine, ceftezole, cefaclor, cefonicid, cefprozil, cefuroxime, cefuzonam, cefmetazole, cefotetan, cefoxitin, loracarbef, cefbuperazone, cefmetazole, cefminox, cefotetan, cefoxitin, cefcapene, cefdaloxime, cefdinir, cefditoren, cefetamet, cefixime, cefmenoxime, cefodizime, cefotaxime, cefovecin, cefpimizole, cefpodoxime, cefteram, ceftibuten, ceftiofur, ceftiolene, ceftizoxime, ceftriaxone, cefoperazone, ceftazidime, latamoxef, cefclidine, cefepime, cefluprenam, cefoselis, cefozopran, cefpirome, cefquinome, flomoxef, ceftobiprole, ceftaroline, imipenem, meropenem, ertapenem, doripenem, panipenem, betamipron, biapenem, razupenem, amikacin, arbekacin, gentamicin, kanamycin, neomycin, netilmicin, paromomycin, rhodostreptomycin, streptomycin, tobramycin, apramycin, framycetin, ribostamycin, bekanamycin, dibekacin, tobramycin, spectinomycin, hygromycin B, paromomycin sulfate, sisomicin, isepamicin, verdamicin, astromicin, sulfasalazine, sulfamethoxazole, sulfamethizole, sulfisoxazole, fluoroquinolone, ketolide, ceftobiprole, flumequine, nalidixic acid, oxolinic acid, piromidic acid, pipemidic acid, rosoxacin, ciprofloxacin, enoxacin, lomefloxacin, nadifloxacin, norfloxacin, pefloxacin, rufloxacin, balofloxacin, gatifloxacin, grepafloxacin, levofloxacin, moxifloxacin, pazufloxacin, sparfloxacin, temafloxacin, tosufloxacin, clinafloxacin, gemifloxacin, sitafloxacin, trovafloxacin, prulifloxacin, azithromycin, erythromycin, clarithromycin, dirithromycin, roxithromycin, telithromycin, demeclocycline, doxycycline, minocycline, oxytetracycline, tetracycline, linezolid, clindamycin, metronidazole, vancomycin, rifabutin, rifampin, nitrofurantoin, chloramphenicol.

In several embodiments, TLAnti may also comprise an anesthetic component. In some embodiments, the anesthetic component may comprise lidocaine. In some embodiments, lidocaine may be provided at a concentration of between 30 mg and 1500 mg per liter of solvent. In some embodiments, lidocaine may be provided at a concentration of between 400 mg and 1250 mg per liter of solvent. In other embodiments, lidocaine may be provided at concentrations of 30 mg to 40 mg, 40 mg to 50 mg, 50 mg to 60 mg, 60 mg to 70 mg, 70 mg to 80 mg, 80 mg to 90 mg, 90 mg to 100 mg, 100 mg to 200 mg, 200 mg to 300 mg, 300 mg to 400 mg, 400 mg to 500 mg, 500 mg to 600 mg, 600 mg to 700 mg, 700 mg to 800 mg, 800 mg to 900 mg, 900 mg to 1,000 mg, 1,000 mg to 1,100 mg, 1,100 mg to 1,200 mg, 1,200 mg to 1,300 mg, 1,300 mg to 1,400 mg, 1,400 mg to 1,500 mg, and 500 mg to 1,000 mg per liter of solvent.

In some embodiments, anesthetics other than lidocaine can be used. Traditional local anesthetics include amide-type or ester-type local anesthetics. Non-traditional anesthetics include neurotoxin-based local anesthetics. Examples of anesthetics that are used in tumescent compositions include, but are not limited to saxitoxin, tetrodotoxin, benzocaine, chloroprocaine, cocaine, cyclomethycaine, dimethocaine, larocaine, propoxycaine, novocaine, proparacaine, tetracaine, amethocaine, articane, bupivacaine, carticaine, cinchocaine, dibucaine, etidocaine, levobupivacaine, mepivacaine, piperocaine, prilocaine, ropivacaine, trimecaine. In some embodiments, combinations of two or more anesthetics may be used. Suitable concentrations of anesthetic are approximately 30 mg to 40 mg, 40 mg to 50 mg, 50 mg to 60 mg, 60 mg to 70 mg, 70 mg to 80 mg, 80 mg to 90 mg, 90 mg to 100 mg, 100 mg to 200 mg, 200 mg to 300 mg, 300 mg to 400 mg, 400 mg to 500 mg, 500 mg to 600 mg, 600 mg to 700 mg, 700 mg to 800 mg, 800 mg to 900 mg, 900 mg to 1,000 mg, 1,000 mg to 1,100 mg, 1,100 mg to 1,200 mg, 1,200 mg to 1,300 mg, 1,300 mg to 1,400 mg, 1,400 mg to 1,500 mg, and 500 mg to 1,000 mg per liter of solvent.

The concentration of the anesthetic component can be varied depending on the sensitivity of the treatment area and the sensitivity of the patient to pain. If the TLAnti is to be used in sensitive areas such as the face or breasts, a higher concentration of anesthetic can be used. Lower concentrations of anesthetic can be used in the TLAnti solution for procedures in less-sensitive areas such as the hips.

Neurotoxins are a varied group of compounds, both chemically and pharmacologically. They vary in both chemical structure and mechanism of action, and produce very distinct biological effects. Neurotoxins act on various ion channels, e.g., sodium, potassium, calcium and chloride channels. Neurotoxins acting on voltage-gated sodium channels can bind to six different sites in the channels, distinguished both by binding site(s) on the ion channels and by effect(s) of a toxin's action.

Non-traditional anesthetics or neurotoxin-based anesthetics may be administered by tumescent infiltration drug delivery. For instance, Neosaxitoxin (NeoSTX) is a site-1 sodium channel blocker that produces prolonged local anesthesia in animals and humans (Lobo, K. et al. 2015 Anesthesiology 123(4): 873-885). Neosaxitoxin can be used in small doses. Other neurotoxin-based local anesthetics include tetrodotoxin, saxitoxin and conotoxins, such as ω-conotoxin (Prasanna, C. et al. (2014 *Int J Anesthesiology Res* 2: 11-15). In some embodiments, an anesthetic is efficacious for at least 6 hours, 12 hours, 18 hours, 24 hours, 30 hours, 36 hours or 48 hours. A local anesthetic solution that can last for 2 days is ideal for treating certain types of conditions, e.g., *Herpes zoster* (shingles).

Tumescent Administration of Vasoconstrictors

TLAnti may further comprise a vasoconstrictor component. Not wishing to be bound by a particular theory, the inclusion of a vasoconstrictor serves two functions. The first is to control the otherwise substantial bleeding resulting from the removal of adipose or other tissue. The second is to control the systemic distribution of the anesthetic and antibiotic components of TLAnti from the subcutaneous fat compartment into the systemic circulation. This helps to concentrate these medications in the area where they are needed for a prolonged period of time, thereby enabling them to exert sufficient anesthetic and antibiotic effects in the surgical site post-operatively or at the site of infection. In addition, the use of a vasoconstrictor limits the systemic absorption of other medications, which reduces the risk of systemic toxicity from elevated serum levels of these medications and thereby minimizes the risk of side effects.

In some embodiments, the vasoconstrictor component is epinephrine. Epinephrine may be provided at a concentration of ≤1 mg/L. In some embodiments, epinephrine is present in a concentration of 0.4 to 1.2 mg per liter of solvent. In other embodiments, epinephrine may be present in a concentration of 0.2 to 0.3 mg, 0.3 to 0.4 mg, 0.4 to 0.5 mg, 0.5 to 0.6 mg, 0.6 to 0.7 mg, 0.7 to 0.8 mg, 0.8 to 0.9 mg, 0.9 to 1 mg, 1 to 1.1 mg, 1.1 to 1.2 mg, 1.2 to 1.3 mg, 1.3 to 1.4 mg, or 1.4 to 1.5 mg per liter of solvent. Stability of epinephrine is optimized is solutions of a moderately acidic pH. TLAnti solutions containing epinephrine would be manufactured with a moderately acidic pH in the range of 3.8 to 5.0 in order to optimize the shelf life of the TLAnti solution. In order to avoid the burning discomfort associated with the infiltration of an acidic solution, the TLAnti solution can be neutralized prior to subcutaneous infiltration by the addition of approximately 10-25 mEq of sodium bicarbonate.

Individuals skilled in the art will recognize that vasoconstrictors other than epinephrine can be used in some embodiments of TLAnti. Examples of suitable vasoconstrictors include, but are not limited to, methoxamine, metraminol, ephedrine, noradrenaline, vasopressin, levonordefrin, prostaglandins, thromboxane A2, leukotriene D4, angiotensin II, neuropeptide Y, and endothelin.

In some embodiments, other constituents may optionally be present in the TLAnti. In one embodiment, bicarbonate can be present in the TLAnti. This helps to neutralize the otherwise acidic solution and reduce the burning sensation reported by many patients. In other embodiments, the TLAnti can further comprise perfluorocarbons. An example can be found in U.S. Pat. No. 6,315,756, the disclosures of which are incorporated in their entirety by reference thereto. In some embodiments TLAnti can further comprise an anti-inflammatory component. Examples of anti-inflammatories include but are not limited to glucocorticoids and NSAIDS. Persons skilled in the art will note that there are a number of potential compounds that can be added to the TLAnti.

In one embodiment, TLAnti comprises lidocaine as the anesthetic component. Lidocaine has a synergistic effect with antibiotics in the prevention and/or treatment of infection at the surgical site. While primarily used as for anesthesia, lidocaine has also been found to have antibiotic properties. Lidocaine is well known to be bactericidal based on in-vitro studies although the precise mechanism has not been explained. Lidocaine is a trans-membrane anion (Na+, K+, Ca+) transport pump inhibitor in prokaryotic cells. Not to be bound by a particular theory, it is believed that lidocaine also acts as an antibiotic efflux pump inhibitor (inhibitor of multidrug resistant efflux systems in bacteria). Lidocaine can thus act synergistically at the local tissue level when both lidocaine and an antibiotic are delivered directly into the targeted tissue using the tumescent drug delivery technique. By inactivating efflux pumps, lidocaine eliminates a mechanism of potential resistance to the cefazolin or other antibiotics used in TLAnti. By flooding the surgical site with significant dosages of two drugs with different and complimentary mechanisms of bactericidal action, the risk of surgical site infection may further be reduced. In addition, tumescent antibiotic delivery of antibiotics together with tumescent lidocaine provides a unique therapeutic benefit in preventing and treating biofilm infections. In contrast, the IV delivery of antibiotics is relatively ineffective against biofilm infections.

Advantages to Using the Tumescent Technique

Tumescent delivery of pharmaceutical agents can provide a highly localized and sustained dosage of the pharmaceutical agent to the delivery site. For example, use of the tumescent technique to deliver TLAnti can provide a high, sustained dosage of antibiotics directly to a surgical site. This has the advantage over the standard treatment with intravenous (IV) antibiotics in that the medication is concentrated and the dosage maximized at the area that is at risk of infection. In some embodiments, the concentration of the antibiotic drug and the local anesthetic drug within the TLAnti (which equals the maximum concentrations of these drugs within the tissues infiltrated with the TLAnti) far exceed the concentrations of these drugs which can be safely achieved by intravenous delivery. In embodiments of TLAnti comprising cefazolin, the concentration of antibiotic in the subcutaneous tissue at the surgical site may be three times or more than the measured maximum serum concentration of the same drug when administered intravenously prior to the procedure. Another advantage is that the therapeutic dosage of antibiotics at the surgical site lasts significantly longer with tumescent administration of TLAnti as compared to IV antibiotics. The result is that any bacteria present at the surgical site are exposed to a higher dosage of antibiotics for a longer period of time when TLAnti is used in place of IV antibiotics.

The bioavailability and effectiveness of an antibiotic can be assessed using the area under the curve (AUC) measurement of the tissue-concentration of the antibiotic as a function of time. After an IV infusion of an antibiotic, the serum-antibiotic AUC may be more than 100 times greater than the serum-antibiotic AUC following tumescent antibiotic delivery. On the other hand, the subcutaneous tissue-antibiotic AUC following the IV delivery of an antibiotic is less than $1/100$th the tissue-antibiotic AUC following tumescent antibiotic delivery. Similarly the peak serum concentrations of an antibiotic is higher after IV infusion compared to tumescent antibiotic, while the peak tissue concentration of antibiotic is lower after IV infusion compared to tumescent antibiotic. Tumescent antibiotic delivery produces significantly lower systemic concentrations of antibiotic while at the same time the local tissue concentration of antibiotic at the site of tumescent antibiotic infiltration is dramatically higher than that which can be achieved by IV antibiotic delivery.

Some embodiments relate to a method of using TLAnti during various surgical procedures. For example, in a liposuction procedure, a therapeutic quantity of TLAnti is injected into the subcutaneous compartment. Once sufficient anesthesia is achieved, another cannula is inserted and adipose tissue removed. The cannula is subsequently removed and the surgical site dressed and/or closed as appropriate. The high levels of antibiotics that remain for some period of time in the surgical site can reduce the risk of postoperative infection. Similarly, a large number of general surgical procedures including, but not limited to, open gastrointestinal surgery, obstetric surgery, orthopedic surgery, and vascular surgery are appropriate for the use of subcutaneous TAD.

The targeted application of highly-concentrated antibiotics to the surgical site largely eliminates many of the problems inherent in systemic, prophylactic antibiotic use. In some embodiments where the tumescent solution comprises antibiotic and vasoconstrictive components, substantial quantities of antibiotics are injected into the surgical site using tumescent technique; however, the antibiotics enter the systemic circulation slowly due to the presence of a vasoconstrictive component. This delayed absorption minimizes the systemic antibiotic concentrations and reduces the possibility of the patient experiencing side effects compared with IV antibiotics. In addition, because the normal bacterial flora of the gut is not exposed to a bactericidal dosage of antibiotics when using the tumescent technique to deliver antibiotic, the risk of inadvertently eliminating the benign and protective bacteria in the gastrointestinal system is reduced. This reduces the likelihood of creating conditions favorable for the overgrowth of antibiotic-resistant and pathogenic bacteria such as *Clostridium difficile*. Finally, by not exposing any bacteria present beyond the surgical site to a therapeutic dosage of antibiotics, the risk of promoting the development of antibiotic resistant strains of a variety of pathogenic bacteria is minimized. This helps to reduce the problem of the spread of antibiotic resistant bacteria into the community.

Some embodiments relate to methods for using tumescent solutions in the subcutaneous space to treat a variety of medical conditions where systemic administration of medications is undesirable or impossible. Various embodiments include, but are not limited to, methods for using tumescent solutions as an anesthetic for medical procedures by clinicians, methods for using tumescent solutions in the administration of fluids to patients by medical professionals and first responders, methods for using tumescent antibiotic solutions to prevent and/or treat infections, methods for providing a chemotherapy agent to tissue after tumor removal and methods for using tumescent solutions in the controlled release of antibiotics and other pharmaceutical agents.

Tumescent administration of anesthetics, antibiotics, vasoconstrictors, and/or other pharmaceutical agents can improve the outcome of surgical procedures to remove tumors. Tumors may be benign or malignant, cancerous. Benign tumors are well circumscribed and are generally treated by surgery alone. Malignant/cancerous tumors on the other hand are more difficult to treat. When malignant tumors are localized, surgical removal is a common treatment option. Approximately 40% of all cancers are treated with surgery alone. In most other cases where surgery is an option, it is combined with other treatments—usually radiation therapy or chemotherapy. One danger of the surgical removal of malignant tumors is the possibility of spreading or seeding the cancerous cells during the process of removing the tumor. Tumescent delivery of a vasoconstrictor to the surgical site can reduce the risk of malignant cells entering the bloodstream. The tumescent technique may also be used to locally deliver chemotherapy agents. Local administration of chemotherapy agents allows for higher localized dosages of the chemotherapy agents than would be tolerated systemically and a reduction of adverse side effects. Examples of chemotherapy agents include, but are not limited to: actinomycin D, adriamycin, alkeran, ara-C, arsenic trioxide (trisenox), avastin, BiCNU, busulfan, carboplatinum, CCNU, cisplatinum, cytoxan, daunorubicin, DTIC, 5-FU, erlotinib, fludarabine, gemcitabine, herceptin, hydrea, idarubicin, ifosfamide, irinotecan, lapatinib, leustatin, 6-MP, methotrexate, mithramycin, mitomycin, mitoxantrone, navelbine, nitrogen mustard, rituxan, 6-TG, taxol, taxotere, topotecan, velban, vincristine, VP-16, and xeloda. Other anticancer drugs, such as angiogenesis inhibitors, may also be tumescently delivered. Examples of angiogenesis inhibitors include, but are not limited to, angiostatin, endostatin, and tumstatin.

In some embodiments, the tumescent solutions can be premixed and packaged prior to being sent to the provider. In other embodiments, one or more components of the tumescent solution can be added shortly before or during the medical procedure wherein they are to be used. In most embodiments, the bulk of the tumescent solution comprises a physiologically compatible solvent. Such solvents can include, for example, saline solution comprising sterile water and 0.9% sodium chloride. More dilute saline solutions can also be used. In other embodiments, a lactated Ringer's solution may be used. This comprises a mixture of sterile water, sodium, chloride, lactate, potassium and calcium that is isotonic with blood. Hartmann's solution can also be used as a solvent in some embodiments. Individuals skilled in the art will recognize that there are a wide variety of possible biologically compatible solvents for use in the solution.

In some embodiments, tumescent solution may be provided as a kit. In some embodiments, the tumescent solution is TLAnti. In one embodiment, TLAnti can be pre-mixed at a manufacturing site and distributed to practitioners in a ready to use form. In such embodiments, the TLAnti can be packaged in a form that allows easy interface with a tumescent reservoir or pumping system. Such packaging can come in a variety of sizes; however typical kits would include one liter or more of tumescent solution. In other embodiments, the tumescent solution may require rehydration or dilution to an administrable concentration.

In one embodiment, a kit can comprise a one liter solution of 0.9% normal saline, 500 mg of cefazolin, 500 mg lidocaine 2%, 1 mg epinephrine, 10 mEq bicarbonate. One of ordinary skill in the art would recognize that several variations in the concentration of lidocaine are possible depending on the intended clinical use. For example, embodiments comprising higher dosages of lidocaine, optionally buffered with additional bicarbonate, can be used when a procedure is to be performed in a sensitive area. Variations on the type and concentration of antibiotic component are also possible. Some embodiments can also include various concentrations of epinephrine or different types of vasoconstrictors. Persons skilled in the art will recognize that many standardized variations are possible and the above example should not be deemed to be limiting.

In some embodiments, the tumescent solution or components for preparing the tumescent solution can be packaged along with a set of cannula, tubing and possibly other surgical instruments for performing liposuction. Such kits can include an appropriate mix of tumescent solution components for the body part where the procedure is to be performed along with appropriately sized, sterile instruments. In some embodiments, the sterile instruments are capable of interacting with standardized liposuction equipment (i.e., peristaltic pumps, adipose tissue receptacles, etc.). Kits for TLAnti use in mastectomy procedures can be prepared comprising the tumescent solution along with any appropriate instruments.

In some embodiments, the tumescent solution can be provided in prefilled tumescent reservoir bags. Such bags could be manufactured by a pharmaceutical company and be sold as "ready to use." Manufactured tumescent delivery bags are a more efficient and economical use of hospital staff than having to custom mix the tumescent solution for each surgical patient. Further, commercially produced prefilled tumescent reservoir bags would eliminate pharmacist error in mixing and preparing tumescent solution. In one embodiment, a TLAnti solution is provided in a prefilled tumescent reservoir bag comprising a dilute solution of local antibiotic such as lidocaine ($\leq 1$ g/L) or other water soluble antibiotic and a vasoconstrictor, such as epinephrine ($\leq 1$ mg/L) in a physiologic electrolyte solution sodium chloride. TLAnti solutions containing epinephrine can be manufactured at a moderately acidic pH to optimize epinephrine stability. The TLAnti solution can be neutralized prior to administration by the addition of approximately 10-25 mEq of sodium bicarbonate. An appropriate amount of sodium bicarbonate can be included for addition to the prefilled tumescent reservoir bag.

Although TLAnti solution is safe when infiltrated into subcutaneous tissue; rapid, systemic infusion of TLAnti may be lethal. There is thus a need to prevent inadvertent IV administration of tumescent solutions. Various safety features may be incorporated into the prefilled tumescent reservoir bags. Tumescent reservoir bags can be designed to be readily distinguishable from standard IV bags. Distinguishing features include, but are not limited to, unique shape, color-coding, and/or printed warnings. In some embodiments, tumescent reservoir bags may be provided as kits in conjunction with a non-standard (non-luer) connector system to prevent inadvertent connection to an IV line.

Tumescent solution can be injected into the subcutaneous space during surgical procedures using a variety of infiltration cannula that are well known to persons skilled in performing surgical procedures. In some embodiments, the TLAnti can be injected into the treatment area using an infiltration cannula comprising a flexible cannula, a hub, and a rigid stylet. The flexible cannula has a proximal end and a distal end. The flexible cannula can also have a plurality of apertures disposed in a pattern about the distal end. The apertures are configured to infiltrate fluid into the subcutaneous tissue of a patient. The hub is configured to be held by a person performing the infiltration procedure. The hub has a first end and an opposing second end. The first end is attached to the proximal end of the flexible cannula and the second end includes a connector configured to connect to an input source for receiving the fluid to be infiltrated into the subcutaneous tissue of the patient. The fluid flows from the connector, through the hub and into the flexible cannula.

In some embodiments, the tumescent solution can also be delivered via a disposable catheter that can be used in emergency situations or under conditions when establishing intravenous access is difficult or impossible. In such embodiments, the tumescent solution can be injected into the subcutaneous space via a flexile cannula with a rigid stylet that can be fabricated from stainless metal or rigid plastic. The distal end of the cannula can be closed to cover the tip of the rigid stylet or open with a hole allowing the tip of the rigid stylet to protrude. In some embodiments, the tip of the rigid stylet can be sharp to facilitate the direct insertion through the skin of the patient. Other embodiments comprise a blunt tip requiring a skin incision to permit insertion of the rigid stylet and the cannula into the subcutaneous space. The stylet can be formed to have either a solid or hollow cross-sectional configuration. The hollow rigid stylet may have small holes distributed along its length in a pattern dissimilar or identical to the pattern of holes placed along the flexible cannula into which the stylet is inserted. Thus, in some embodiments, the stylet itself can be used as an infiltration cannula.

Our research has provided objective pharmacokinetic data that, in some embodiments, support approximately 28 mg/kg for infiltration local anesthesia. Compared to general anesthesia, Tumescent Infiltration Lidocaine Anesthesia has the ability to:

1) Improve patient safety (reduce the need for general anesthesia),

2) Improve patient comfort by reducing PONV (post-operative nausea and vomiting) reducing hypothermia and providing prolonged post-operative analgesia 3) Reduce cost, 4) Reduce the risk of post-operative venous thromboembolism (tumescent lidocaine significantly reduces systemic platelet activation without adversely affecting surgical hemostasis, manuscript in preparation).

5) Provide improved pre-emptive, intraoperative and postoperative anesthesia and analgesia and thus reduce the need for narcotic analgesia while accelerating earlier post-op ambulation 6) Reduce the risk of post-surgical neuropathic pain by reducing inflammation and neurologic peripheral and central sensitization.

7) Reduce the risk of excessive systemic inflammatory response (systemic lidocaine attenuates activity of inflammatory mediator associated with innate immunity and thus reduce the risk of sepsis and systemic inflammatory response syndrome.

8) Reduce the risk of surgical site infections (SSI) by subcutaneous infiltration of tumescent solution containing antibiotic(s), e.g., cefazolin and metronidazole.

9) Completely eliminate the pain and reduce the duration of acute *Herpes zoster* dermatitis and reduce the risk of chronic post-herpetic neuralgia (PHN) by tumescent infiltration of a TLA solution containing a dilute solution of acyclovir.

In contrast to the tumescent infiltration technique disclosed herein, which allows for relatively high drug dosages, including for lidocaine, continued FDA insistence on a lower maximum lidocaine dosage of 7 mg/kg by conventional methods presents a major impediment to improvement in patient care and a dramatic reduction in the cost of care.

Methods of Treating a Localized Viral Infection

The tumescent technique may be used to treat localized viral infections. Surprisingly, while some antibiotics and antiviral agents are not recommended for subcutaneous use, the tumescent technique allows such agents to be safely used at relatively high, localized therapeutic dosages. For instance, the antibiotic gentamycin and the antiviral compound Acyclovir, which is commonly used to treat infections caused by herpes viruses, such as genital herpes, cold sores, shingles, and chicken pox, are not recommended for subcutaneous administration. With the tumescent technique, there is a relatively large total amount of drug in the patient's body, but the drug is isolated from the systemic circulation because only the drug on the outer boundary of the mass of drug is the available for absorption, whereas the portion of the drug located within the central portion of the mass of fluid is virtually isolated from the systemic circulation by virtue of profound capillary vasoconstriction.

The tumescent technique is amenable to treatment of localized viral infection, such as for treatment of viral diseases related to herpes virus (including *Herpes Simplex* I, *Herpes Simplex* II, *herpes zoster* (shingles), herpetic conjunctivitis, keratitis, and genital herpes). Other types of localized viral infection include Molluscum Contagiosum, a common skin infection caused by a pox virus that affects both children and adults and Kaposi's sarcoma (KS), a connective tissue cancer caused by human herpes virus 8.

A non-exhaustive list of antiviral agents used to treat localized viral infection, e.g., shingles, includes: Abacavir, Acyclovir, Adefovir, Amantadine, Amprenavir, Ampligen, Arbidol, Atazanavir, Atripla, Balavir, Brivudine, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Ganciclovir, Ibacitabine, Imunovir, Idoxuridine, Imiquimod, Interferon type I, Interferon, Lamivudine, Lopinavir, Loviride, Maraviroc, Moroxydine, Methisazone, Nelfinavir, Nevirapine, Nexavir, Nucleoside analogues, Novir, Oseltamivir, Peginterferon alfa-2a, Penciclovir, Peramivir, Pleconaril, Raltegravir, Ribavirin, Rimantadine, Ritonavir, Pyramidine, Saquinavir, Sofosbuvir, Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, Zidovudine.

In tumescent antiviral drug delivery, the subcutaneous concentration of the antiviral agent achieved is simultaneously: (i) below the threshold for local tissue toxicity while sufficiently concentrated to result in a significant positive local therapeutic effect, and (ii) greater than the maximum subcutaneous interstitial fluid concentration that can be achieved by conventional intravenous delivery or oral delivery of the antiviral agent. For example the subcutaneous concentration of the antiviral agent achieved is equal to or about 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, 200%, 250%, 300%, 350%, 400%, 450% or 500% greater than the maximum subcutaneous interstitial fluid concentration that can be achieved by conventional intravenous delivery or oral delivery of the antiviral agent.

In some embodiments, Acyclovir is used at a diluted concentration of 0.1 g/L-10 g/L, preferably 0.5 g/L-5 g/L, more preferably 1-2 g/L, or at 1 g/L.

In some embodiments, Gentamycin is used at a diluted concentration of 0.1 mg/L-1 g/L, preferably 50-800 mg/L, more preferably 50-200 mg/L or at 80 mg/L.

A tumescent composition used to treat localized viral infection typically contains an antiviral component and a vasoconstrictor. The tumescent composition may optionally comprise other components, such as antibiotic, anesthetic and anti-inflammatory components.

Tumescent Drug Delivery of an Antiviral Agent for *Herpes zoster*

Pathophysiology of *Herpes zoster* Dermatitis

Varicella-zoster virus (VZV) causes varicella (chickenpox) and *herpes zoster* (shingles). Varicella (chickenpox) is highly contagious. It initially enters the host by penetrating the respiratory epithelium causing viremia and the classic vesicular chickenpox rash. From the skin, VZV migrates within cutaneous sensory neurons to arrive at sensory dorsal root ganglia (DRG). As the host develops a cellular immunity involving CD4 & CD8 cells and a serologic immune response, the rash subsides and the VZV virus within the ganglion becomes latent.

Years later, with age-related waning of cellular immunity or with immunodeficiency (chemotherapy or HIV infection) the latent VZV can reactivate, proliferate and migrate along a sensory nerve from the dorsal root ganglion toward the skin of the corresponding dermatome.

The initial manifestation of *H zoster* is abrupt onset of localized pain that extends over the next few days within a localized unilateral area of skin spanning 1 to 3 adjacent dermatomes. Patients often attribute the acute onset of the pain to be the result of muscle strain, back-muscle spasm, or a bacterial infection. Within 2-4 days there is the onset of. The host's immune response produces an intense inflammatory reaction with a potential for permanent sensory nerve injury.

The area and intensity of painful skin tends to enlarge over the next 2 to 3 days. Zoster pain is intense, and has 3 clinically distinct components: a deep burning unremitting pain, sporadic acute sharp lancinating pain, and a paresthetic pain that is elicited by light touch or temperature change (mechanical allodynia).

Within 2 to 3 days after the onset of pain, there is the appearance of a characteristic erythematous papulovesicular rash. Soon the vesicles enlarge and coalesce into bullae distributed over the affected dermatome(s). The vesiculation and bulla formation progress to epidermal crusting and necrosis, which then resolves over 14 days or so. Usually the pain of zoster gradually resolves over several weeks to months.

Post Herpetic Neuralgia (PHN)

Post herpetic neuralgia (PHN) is the most common and perhaps the most dreaded complication of *Herpes zoster*. PHN is defined as pain that persists for more than 3 months after acute *herpes zoster*. PHN often does not respond well to narcotics or other analgesics. The incidence of post herpetic neuralgia (PHN) is approximately 10%, but among patients with hematologic malignancy it is at least 48%.

*Herpes zoster* patients with greater pain and rash severity have greater risk of PHN. This suggests that greater neural damage (caused by more severe acute infection) contributes to risk of PHN. Indeed, acute pain severity is a major risk factor for PHN (Dworkin R H, Boon R J, Griffin D R G. Postherpetic neuralgia: Impact of Famciclovir, age, rash severity and acute pain in *Herpes zoster* patients. JID 1998; 178 (Suppl) S76-S80). Current approaches to acute zoster pain rely on aggressive analgesic intervention that merely attenuates zoster pain. Only TI acyclovir (tumescent lidocaine and acyclovir) is capable of eliminating 100% of acute zoster pain for up to 12 to 18 hours and providing unprecedented high tissue concentrations, superior bioavailability within affected cutaneous tissue and prolonged time within the tumescent therapeutic ambit range (TTAR) of acyclovir.

Because PHN is a neuropathic pain that is resistant to treatment, preventing PHN is of prime importance. TI of acyclovir delivers unprecedented high and prolonged subcutaneous concentrations of lidocaine, eliminates 100% of pain for up to 12 hours or more without repeat dosing and thus reduces the risk of neuropathic pain and PHN. In this fashion Tumescent lidocaine+ acyclovir is more effective than IV acyclovir at reducing the risk of PHN.

It is known that the risk of developing *H zoster* is closely correlated with a person's age and immune competence in suppressing VZV proliferation. However once the *H zoster* occurs the pathogenesis of PHN is not completely understood.

The zoster blister contains large amounts of infectious VZV viral particles. The risk of severe *H. zoster* and the risk of PHN are closely correlated with the intensity of the host's secondary inflammatory immune response to VZV, the degree of pathologic damage to sensory nerves, the total area of blistering, the intensity and duration of epidermal necrosis, and the intensity and duration of acute pain.

Early treatment with oral anti-VZV drugs or IV acyclovir shortens the duration and intensity of acute zoster pain. Higher doses of famciclovir have been shown to reduce the duration of zoster pain and the risk of PHN. However, the bioavailability of systemic delivery of anti-VZV drugs within zoster-affected subcutaneous tissue is limited by cutaneous edema and capillary necrosis. Results of our pharmacokinetic research (our unpublished data) show that tumescent infiltration of a drug dramatically increases drug bioavailability in cutaneous interstitial fluid by one to two orders of magnitude.

Antiviral drugs do not provide anesthesia and do not eliminate acute zoster pain. The intensity and duration of any acute pain increases the risk of a permanent neuropathic pain syndrome. PHN is an example of neuropathic pain. Acyclovir, valacyclovir and famciclovir treat certain, but not all, aspects of *H. zoster*. They reduce the intensity and duration of zoster pain and decrease the risk of developing PHN. Only Tumescent lidocaine+acyclovir can both eliminate 100% of pain (for hours) and can decrease viral replication rate and the extent and intensity. The risk factors that have been shown to increase the incidence of PHN include: a) increasing age, b) intensity of pain upon initial presentation, c) duration of pain upon initial presentation, d) extent of the *H. zoster* rash upon presentation, e) intensity of pain one week after initiating antiviral therapy, f) progression of pain one week after initiating antiviral therapy and g) progression of dermatitis one week after initiating antiviral therapy.

An important embodiment of the present invention is the safe and effective subcutaneous infiltration of an antiviral agent for the treatment of *Herpes zoster*. *Herpes Zoster* or Shingles is an unusually painful disease caused by the varicella zoster virus that affects one million people in the United States annually. Among persons 85 years of age or older, 50% will eventually have *herpes zoster*. *H. zoster* can progress into chronic, potentially devastating, post-herpetic neuralgia (PHN).

Methods disclosed herein involve the subcutaneous infiltration of a tumescent solution of dilute lidocaine and epinephrine and one or more zoster-specific antiviral drugs (e.g. acyclovir) and/or a broad-spectrum antiviral (e.g., cidofovir), with or without anti-inflammatory drugs (e.g., steroidal anti-inflammatory drugs such as triamcinolone, non-steroidal anti-inflammatories)), and with or without sodium bicarbonate.

The beneficial result of subcutaneous delivery of acyclovir by tumescent infiltration (TI) to treat shingles is unexpected and not obvious. The FDA-approved package insert for ZOVIRAX® (5%=1 gm/20 ml) (acyclovir sodium) for Injection states, "WARNINGS: ZOVIRAX for Injection is intended for intravenous infusion only, and should not be administered topically, intramuscularly, orally, subcutaneously, or in the eye."

There are no published accounts of the clinical use of subcutaneously injected acyclovir in human subjects. Thus tumescent infiltration of acyclovir is unexpected and not obvious. Extravasated acyclovir is a known complication of IV delivery and can produce significant inflammation, bullae and pain.

In contrast to the teachings of those skilled in the art of treating patients with zoster, we have found that a subcutaneous infiltration of dilute solution of an antiviral agent, such as acyclovir, in a tumescent solution is remarkably safe and effective at 1) eliminating acute zoster pain for at least 12 hours or more, 2) attenuating the progression of blistering zoster dermatitis and 3) reducing the risk of developing PHN.

The antiviral drugs acyclovir (Zovirax®), valacyclovir (Valtrex®) and famcyclovir (Famvir®) effectively treat *H. zoster*. Only Acyclovir is available for IV delivery. At present, oral delivery is considered sufficient for most cases of *H. zoster*. IV delivery is usually reserved for patients requiring hospitalization, for example disseminated *H. zoster* in immunocompromised hematopoetic transplant patients or HIV (AIDS) patients, severe forms of zoster such as *herpes zoster* ophthalmicus that can cause blindness, herpes oticus (Ramsay-Hunt syndrome) which can cause unilateral facial paralysis and/or permanent hearing loss, CNS zoster and Zoster pneumonia. In general, the sooner treatment begins, the less severe the intensity of the rash and pain and the shorter its duration.

Subcutaneous tumescent drug delivery of acyclovir and lidocaine (TAD-acyclovir) typically eliminates 100% of acute zoster pain for 12 hours or more. This is unique among all forms of *Herpes zoster* treatments. Using an elastomeric pump to provide continuous subcutaneous infiltration, TI-acyclovir can eliminate zoster pain for days.

Greater subcutaneous acyclovir bioavailability and concentrations:

1) decrease VZV replication/proliferation within the dermatomal skin and nerves,
2) decrease VZV-induced inflammation,
3) decrease damage to skin and decrease local sensory nerve damage,
4) reduce the intensity, extent and duration of acute pain,
5) reduce the likelihood of developing chronic post herpetic neuralgia, and
6) reduce post-zoster hypopigmentation and scaring.

Tumescent Infiltration Antifungal Delivery

Tumescent infiltration can also be used to treat local and systemic fungal infections. A partial list of antifungal drugs includes:

Polyenes: amphotericin B, candicidin, Filipin, Hamycin, Natamycin, Nystatin and Rimocidin;

Imidazoles: Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole and Tioconazole;

Triazoles: Albaconazole, Efinaconazole, Epoxiconazole, Fluconazole, Isavuconazole, Itraconazole, Posaconazole, Propiconazole, Ravuconazole, Terconazole and Voriconazole; and Thiazoles: Abafungin.

Tumescent Infiltration Antiprotozoal Delivery

Tumescent infiltration can also be used to treat local and systemic protozoa infections. A partial list of antiprotozoal drugs includes:

Antinematodes: Mebendazole, Pyrantel pamoate, Thiabendazole, Diethylcarbamazine, and Ivermectin;

Anticestodes: Niclosamide, Praziquantel, and Albendazole;

Antitrematodes: Praziquantel;

Antiamoebics: Rifampin and Amphotericin B; and

Antiprotozoals: Melarsoprol, Eflornithine, Metronidazole, Tinidazole and Miltefosine.

Methods of Treating Localized Neuropathic Pain

Neuropathic pain is a complex, chronic pain state that is generally accompanied by tissue injury. With neuropathic pain, the nerve fibers themselves might be damaged, dysfunctional, or injured. These damaged nerve fibers send incorrect signals to other pain centers. The clinical causes of neuropathic pain are diverse and include both trauma and disease. For example, traumatic nerve compression or crush and traumatic injury to the brain or spinal cord are common causes of neuropathic pain. Furthermore, most traumatic nerve injuries also cause the formation of neuromas, in which pain occurs as a result of aberrant nerve regeneration. In addition, cancer-related neuropathic pain is caused when tumor growth painfully compresses adjacent nerves, brain or spinal cord. Neuropathic pain can be caused by various diseases, such as viral infections and diabetes and alcoholism. For example, post herpetic neuralgia is caused by herpes viral infection and can cause moderate to severe chronic pain in the infected skin area to the subject.

Unfortunately, the available drug therapies for neuropathic pain often do not provide adequate pain relief. In addition, current therapies have serious side-effects including, for example, cognitive changes, sedation, nausea and, in the case of narcotic drugs, addiction. Many patients suffering from neuropathic pain are elderly or have other medical conditions that particularly limit their tolerance of the side-effects associated with available drug therapy. A number of anti-inflammatory, anxiolytic, narcotic and even anti-convulsants are currently used by the practitioners to treat neuropathic pain, but with limited success.

Selective serotonin reuptake inhibitors (SSRIs like paroxetine and citalopram) and other antidepressants (venlafaxine, bupropion) have been used in some patients.

Another common treatment of neuropathic pain includes anti-seizure medications (carbamazepine, phenytoin, gabapentin, lamotrigine, and others). Pregabalin and duloxetine can also be effective for nerve pain. Like amitriptyline, they may be given alongside other pain medications in the most troublesome nerve pain conditions. Duloxetine is licensed for pain from nerve damage resulting from diabetes, which most often starts in the feet.

The inadequacy of current therapy in relieving neuropathic pain calls for new compositions and methodologies of addressing the physical and social needs of the patient suffering from such condition. Methods of alleviating neuropathic pain would improve the quality of life for many people suffering from pain due to trauma or disease.

Neuropathic pain may be brought on by trauma, disease or irritation. There are countless types of neuropathic pain. Some of the common types include:

Postherpetic neuralgia. Postherpetic neuralgia is neuropathic pain that is brought on by an outbreak of shingles, and persists after the condition has cleared.

Trigeminal neuralgia. Trigeminal neuralgia is characterized by shooting neck and facial pain. The pain is often worse with light touch, and may make activities like shaving very painful.

Phantom limb pain. Phantom limb pain can occur in some people after a limb is amputated. This pain feels as if it is coming from part of the limb that is no longer there.

Diabetic neuropathy. Diabetic neuropathy causes burning or stabbing pain in the hands and feet of some people who suffer from diabetes.

Carpal tunnel syndrome. Carpal tunnel syndrome is caused by nerve compression in the wrists, and causes pain in the wrist, thumb and fingers.

Sciatica. Sciatica is caused by compression or irritation of the sciatic nerve, and often results in shooting pain that radiates down the back of leg.

Chronic neuropathic pain can also be caused by other chronic pain disorders. For instance, someone with degenerative disk disease, a form of arthritis, may experience neuropathic back pain if the condition causes damage to the nerves entering or exiting the spine. Some other conditions that may cause chronic neuropathic pain include spinal cord injury, post-surgical pain and cancer.

In tumescent drug delivery for neuropathic pain, the subcutaneous concentration of drug achieved is simultaneously: (i) below the threshold for local tissue toxicity while sufficiently concentrated to result in a significant positive local therapeutic effect, and (ii) greater than the maximum subcutaneous interstitial fluid concentration that can be achieved by conventional intravenous delivery or oral delivery of the drug. For example the subcutaneous concentration of the drug achieved is equal to or about 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, 200%, 250%, 300%, 350%, 400%, 450% or 500% greater than the maximum subcutaneous interstitial fluid concentration that can be achieved by conventional intravenous delivery or oral delivery of the drug.

Methods of Treating a Localized Inflammation

In cases of localized inflammation, the tumescent technique allows anti-inflammatory agents to be safely administered at relatively high concentrations. Examples of anti-inflammatories include but are not limited to glucocorticoids and non-steroidal anti-inflammatory drugs (NSAIDS). Persons skilled in the art will note that there are a number of potential compounds that can be added to the tumescent composition.

Example glucocorticoids include triamcinolone, dexamethsasone, prednisolone, methylprednisolone, budesonide betamethasone, hydrocortisone and cortisone.

Example NSAIDS include Aspirin (Anacin®, Ascriptin®, Bayer®, Bufferin®, Ecotrin®, Excedrin®); choline and magnesium salicylates (choline magnesium trisalicylate (CMT), Tricosal®, Trilisate®); Choline salicylate (Arthropan®); Celecoxib (Celebrex®); Diclofenac potassium (Cataflam®); Diclofenac sodium (Voltaren®, Voltaren XR®); Diclofenac sodium with misoprostol (Arthrotec®); Diflunisal (Dolobid®); Etodolac (Lodine®, Lodine XL®); Fenoprofen calcium (Nalfon®); Flurbiprofen (Ansaid®); Ibuprofen (Advil®, Motrin®, Motrin IB®, Nuprin®); Indomethacin (Indocin®, Indocin SR®); Ketoprofen (Actron®, Orudis®, Orudis KT®, Oruvail); Magnesium salicylate (Arthritab®, Bayer Select®, Doan's Pills®, Magan®, Mobidin®, Mobogesic®); Meclofenamate sodium (Meclomen®); Mefenamic acid (Ponstel®); Meloxicam (Mobic®); Nabumetone (Relafen®); Naproxen (Naprosyn®, Naprelan); Naproxen sodium (Aleve®, Anaprox®); Oxaprozin (Daypro®); Piroxicam (Feldene®); Rofecoxib (Vioxx®); Salsalate (Amigesic®, Anaflex 750®, Disalcid®, Marthritic®, Mono-Gesic®, Salflex®, Salsitab®); Sodium salicylate (various generics); Sulindac (Clinoril®); Tolmetin sodium (Tolectin®) and Valdecoxib (Bextra®).

Natural and synthetic glucocorticoids remain at the forefront of anti-inflammatory and immunosuppressive therapies. They are widely used to treat both acute and chronic inflammations, including rheumatoid arthritis, inflammatory bowel disease, multiple sclerosis, psoriasis and eczema, as well as being used in treatment of certain leukaemias and in immunosuppressive regimes following organ transplant. The anti-inflammatory effects are mediated either by direct binding of the glucocorticoid/glucocorticoid receptor complex to glucocorticoid responsive elements in the promoter region of genes, or by an interaction of this complex with other transcription factors, in particular activating protein-1 or nuclear factor-kappaB. Glucocorticoids inhibit many inflammation-associated molecules such as cytokines, chemokines, arachidonic acid metabolites, and adhesion molecules.

NSAIDs comprise a large class of drugs with many different options. In addition to aspirin, there are currently several types of both non-prescription (over-the-counter) NSAIDs and prescription brands of NSAIDs. The three types of NSAIDs most commonly used to treat many types of back pain and neck pain include: Ibuprofen (e.g. brand names Advil®, Motrin®, Nuprin®); Naproxen (e.g. brand names Aleve®, Naprosyn®), and COX-2 inhibitors (e.g., Celebrex®).

In tumescent delivery of an anti-inflammatory drug, the subcutaneous concentration of the anti-inflammatory drug achieved is simultaneously: (i) below the threshold for local tissue toxicity while sufficiently concentrated to result in a significant positive local therapeutic effect, and (ii) greater than the maximum subcutaneous interstitial fluid concentration that can be achieved by conventional intravenous delivery or oral delivery of the anti-inflammatory drug. For example the subcutaneous concentration of the anti-inflammatory drug achieved is equal to or about 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, 200%, 250%, 300%, 350%, 400%, 450% or 500% greater than the maximum subcutaneous interstitial fluid concentration that can be achieved by conventional intravenous delivery or oral delivery of the anti-inflammatory drug.

Methods of Treating a Localized Cancer

Treating a localized cancer or reducing the growth of a tumor by localized delivery of a cancer medication can be achieved by using the tumescent technique. Using chemotherapy to treat cancer typically has unpleasant side effects. The toxic effects of the medication affect healthy cells, as well as those of the tumor itself. This leads to symptoms like nausea, hair loss or reduced effectiveness of the immune system. The tumescent technique allows higher doses of medication to be used, while the rest of the patient's body remains unaffected.

Chemotherapy agents are selected based on the type of cancer, the stage of the cancer (how far it has spread), the patient's age, the patient's overall health, other serious health problems (such as heart, liver, or kidney diseases) and the types of cancer treatments given in the past.

Chemotherapy regimens or treatment plans may use a single drug or a combination of drugs, which may be more effective than a single drug, because the cancer cells can be attacked in several different ways.

Alkylating Agents

Alkylating agents directly damage DNA (the genetic material in each cell) to keep the cell from reproducing. These drugs work in all phases of the cell cycle and are used to treat many different cancers, including leukemia, lymphoma, Hodgkin disease, multiple myeloma, and sarcoma, as well as cancers of the lung, breast, and ovary. Because these drugs damage DNA, they can cause long-term damage to the bone marrow. In rare cases, this can lead to acute leukemia. The risk of leukemia from alkylating agents is "dose-dependent," meaning that the risk is small with lower doses, but goes up as the total amount of the drug used gets higher. The risk of leukemia after getting alkylating agents is highest about 5 to 10 years after treatment.

Alkylating agents are divided into different classes, including: Nitrogen mustards: such as mechlorethamine (nitrogen mustard), chlorambucil, cyclophosphamide (Cytoxan®), ifosfamide, and melphalan; Nitrosoureas: such as streptozocin, carmustine (BCNU), and lomustine; Alkyl sulfonates: busulfan; Triazines: dacarbazine (DTIC) and temozolomide (Temodar®); and Ethylenimines: thiotepa and altretamine (hexamethylmelamine).

The platinum drugs (such as cisplatin, carboplatin, and oxalaplatin) are sometimes grouped with alkylating agents because they kill cells in a similar way. These drugs are less likely than the alkylating agents to cause leukemia later.

Antimetabolites

Antimetabolites interfere with DNA and RNA growth by substituting for the normal building blocks of RNA and DNA. These agents damage cells during the S phase, when the cell's chromosomes are being copied. They are commonly used to treat leukemias, cancers of the breast, ovary, and the intestinal tract, as well as other types of cancer.

Examples of antimetabolites include: 5-fluorouracil (5-FU), 6-mercaptopurine (6-MP), Capecitabine (Xeloda®), Cytarabine (Ara-C®), Floxuridine, Fludarabine, Gemcitabine (Gemzar®), Hydroxyurea, Methotrexate and Pemetrexed (Alimta®).

Anti-Tumor Antibiotics

These drugs are not like antibiotics used to treat infections. They work by altering the DNA inside cancer cells to keep them from growing and multiplying.

1. Anthracyclines

Anthracyclines are anti-tumor antibiotics that interfere with enzymes involved in DNA replication. These drugs work in all phases of the cell cycle. They are widely used for a variety of cancers. Examples of anthracyclines include: Daunorubicin, Doxorubicin (Adriamycin®), Epirubicin and Idarubicin. A major concern when giving these drugs systemically is that they can permanently damage the heart if given in high doses. For this reason, lifetime dose limits are often placed on these drugs. However, with the tumescent technique, this problem is avoided.

2. Other Anti-Tumor Antibiotics

Anti-tumor antibiotics that are not anthracyclines include: Actinomycin-D, Bleomycin, Mitomycin-C, and Mitoxantrone (also acts as a topoisomerase II inhibitor).

Topoisomerase Inhibitors

These drugs interfere with enzymes called topoisomerases, which help separate the strands of DNA so they can be copied during the S phase. (Enzymes are proteins that cause chemical reactions in living cells.) Topoisomerase inhibitors are used to treat certain leukemias, as well as lung, ovarian, gastrointestinal, and other cancers. Topoisomerase inhibitors are grouped according to which type of enzyme they affect.

Topoisomerase I inhibitors include Topotecan and Irinotecan (CPT-11). Topoisomerase II inhibitors include Etoposide (VP-16), Teniposide and Mitoxantrone (which also acts as an anti-tumor antibiotic). Topoisomerase II inhibitors can increase the risk of a second cancer—acute myelogenous leukemia (AML)—as early as 2 to 3 years after the drug is given.

Mitotic Inhibitors

Mitotic inhibitors are often plant alkaloids and other compounds derived from natural products. They work by stopping mitosis in the M phase of the cell cycle but can damage cells in all phases by keeping enzymes from making proteins needed for cell reproduction. Examples of mitotic inhibitors include: Taxanes: paclitaxel (Taxol®) and docetaxel (Taxotere®); Epothilones: ixabepilone (Ixempra®); Vinca alkaloids: vinblastine (Velban®), vincristine (Oncovin®), and vinorelbine (Navelbine®); and Estramustine (Emcyt®). They are used to treat many different types of cancer including breast, lung, myelomas, lymphomas, and leukemias. These drugs may cause nerve damage, which can limit the amount that can be given.

Corticosteroids

Corticosteroids, often simply called steroids, are natural hormones and hormone-like drugs that are useful in the treatment of many types of cancer, as well as other illnesses. When these drugs are used as part of cancer treatment, they are considered chemotherapy drugs. Examples of corticosteroids include: Prednisone, Methylprednisolone (Solumedrol®); and Dexamethasone (Decadron®). Steroids are also commonly used to help prevent nausea and vomiting caused by chemotherapy. They are used before chemotherapy to help prevent severe allergic reactions, too.

Other Chemotherapy Drugs

Some chemotherapy drugs act in slightly different ways and do not fit well into any of the other categories. Examples include drugs like L-asparaginase, which is an enzyme, and the proteosome inhibitor bortezomib (Velcade®).

A localized cancer is usually found in the tissue or organ where it began, and has not spread to nearby lymph nodes or to other parts of the body, or the spread is limited in scope.

Non-limiting examples of localized cancers include single-lesion skin cancers, solitary pulmonary nodules (single lung tumor), Adrenal Cancer, Anal Cancer, Bile Duct Cancer, Bladder Cancer, Bone Cancer, Brain/CNS Tumors In Adults, Brain/CNS Tumors In Children, Breast Cancer, Breast Cancer In Men, Cancer in Adolescents, Cancer in Children, Cancer in Young Adults, Cancer of Unknown Primary, Castleman Disease, Cervical Cancer, Colon/Rectum Cancer, Endometrial Cancer, Esophagus Cancer, Ewing Family Of Tumors, Eye Cancer, Gallbladder Cancer, Gastrointestinal Carcinoid Tumors, Gastrointestinal Stromal Tumor (GIST), Gestational Trophoblastic Disease, Hodgkin Disease, Kaposi Sarcoma, Kidney Cancer, Laryngeal and Hypopharyngeal Cancer, Leukemia, Liver Cancer, Lung Cancer, Lung Cancer—Non-Small Cell, Lung Cancer—Small Cell, Lung Carcinoid Tumor, Lymphoma, Lymphoma of the Skin, Malignant Mesothelioma, Multiple Myeloma, Myelodysplastic Syndrome, Nasal Cavity and Paranasal Sinus Cancer, Nasopharyngeal Cancer, Neuroblastoma, Non-Hodgkin Lymphoma, Non-Hodgkin Lymphoma In Children, Oral Cavity and Oropharyngeal Cancer, Osteosarcoma, Ovarian Cancer, Pancreatic Cancer, Penile Cancer, Pituitary Tumors, Prostate Cancer, Retinoblastoma, Rhabdomyosarcoma, Salivary Gland Cancer, Sarcoma—Adult Soft Tissue Cancer, Skin Cancer, Skin Cancer—Basal and Squamous Cell, Skin Cancer—Melanoma, Skin Cancer—Merkel Cell, Small Intestine Cancer, Stomach Cancer, Testicular Cancer, Thymus Cancer, Thyroid Cancer, Uterine Sarcoma, Vaginal Cancer, Vulvar Cancer, Waldenstrom Macroglobulinemia, and Wilms Tumor In particularly preferred embodiments, localized cancers suitable for treatment by tumescent delivery of a chemotherapy drug include: Pancreatic cancer, Ovarian cancer, Lung cancer, Breast cancer, Liver cancer, Melanoma, Kidney cancer, Colon cancer, as well as discrete metastatic lesions.

In tumescent delivery of chemotherapy drug, the subcutaneous concentration of the chemotherapy drug achieved is simultaneously: (i) below the threshold for local tissue toxicity while sufficiently concentrated to result in a significant positive local therapeutic effect, and (ii) greater than the maximum subcutaneous interstitial fluid concentration that can be achieved by conventional intravenous delivery or oral delivery of the chemotherapy drug. For example the subcutaneous concentration of the chemotherapy drug achieved is equal to or about 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, 200%, 250%, 300%, 350%, 400%, 450% or 500% greater than the maximum subcutaneous interstitial fluid concentration that can be achieved by conventional intravenous delivery or oral delivery of the chemotherapy drug.

Biologic Drug Delivery

Biologic drugs generally consist of large organic molecules derived from biological sources. Traditional anticancer chemotherapy drugs are akin to weapons of mass destruction that can damage any living cell. An anticancer chemotherapy drug is only therapeutic if it is more toxic to cancer cells than to healthy cells. In contrast, biologic drugs are focused weapons that targets specific pathologic cells or pathologic cellular products. Examples of Biologic drugs include: cytokines, chemokines, growth factors, viral antigens, enzymes, hormones, neurotrophins, antibodies, proteins that target specific genes, antibody to a specific antigen.

An important subset of biologic anticancer drugs consists of antibodies that target specific CD antigens or CD markers on malignant cells. Cluster of Differentiation or Classification Determinant (CD) is a protocol for identifying cell surface molecules and for immunopheno-typing of cells. CD molecules can act as receptors or ligands for altering the behavior of the cell or other functions cell adhesion.

Lymph Node Targeted Drug Delivery

Lymph node targeted drug delivery of anticancer medications using tumescent infiltration provides a unique mode of drug delivery. Lymphatic vessels specifically absorb large molecules from interstitial tissue spaces and return these large molecules to the systemic circulation via lymph nodes. Tumescent infiltration drug delivery can target metastatic cancer cells within lymph nodes. For example, a large volume of dilute solution of proteinaceous anti-melanoma drugs, if infiltrated into the subcutaneous tissue around the site of a primary melanoma tumor, will be absorbed into the lymph vessels that drain the primary tumor site and deliver the drugs directly to the lymph nodes which might have trapped metastatic melanoma cells, thus preventing further, more wide spread metastases.

Snake Antivenin Delivery

Snake antivenin delivery is another unique application of tumescent infiltration. Snake venom contains multiple large proteins, which have both local and systemic effects. Antivenin contains antibodies to the venomous proteins. Snakebite is painful. Tumescent infiltration of a snake antivenin can, 1) immediately relieve the pain (lidocaine effect), dilute the venom decreasing tissue toxicity, neutralize much of the venom at the site of the bite before it is systemically absorbed. Venom is absorbed via lymphatic vessels. Large molecular antivenin antibodies are also specifically absorbed via lymphatic vessels. Following tumescent infiltration around the site of a snakebite, the antivenin is absorbed into the same lymphatic vessels as the venom. In this fashion, tumescent antivenin can neutralize the venom within lymphatic vessels before the venom reaches the systemic circulation.

Methods of Preventing or Treating Sepsis

Sepsis is a body's overwhelming and life-threatening response to an infection, which can lead to tissue damage, organ failure, and even death. Patients are given a diagnosis of sepsis when they develop clinical signs of infections or systemic inflammation. Sepsis is not diagnosed based on the location of the infection or by the name of the causative microbe. Physicians draw from a list of signs and symptoms in order to make a diagnosis of sepsis, including abnormalities of body temperature, heart rate, respiratory rate, and white blood cell count. For example, sepsis may be diagnosed in a 72-year-old man with pneumonia, fever, and a high white blood cell count, and in a 3-month-old with appendicitis, low body temperature, and a low white blood cell count.

Sepsis is defined as severe when these findings occur in association with signs of organ dysfunction, such as hypoxemia, oliguria, lactic acidosis, elevated liver enzymes, and altered cerebral function. Nearly all victims of severe sepsis require treatment in an intensive care unit for several days or weeks. While most cases of sepsis are associated with disease or injury, many events follow routine, even elective surgery.

Some embodiments disclosed herein relate to prevention or treatment of sepsis in a subject. Tumescent drug delivery can achieve a localized reservoir of a drug, which is present at a relatively high concentration in local interstitial tissues. While the high concentration of drug delivered by the tumescent technique is confined to localized tissues targeted, a lower systemic level of the drug can also be attained, originating from the localized reservoir established by tumescent delivery. For example, antibiotic or anti-inflammatory agents delivered tumescently can provide ongoing systemic levels of the antibiotic or anti-inflammatory agent, which can effectively prevent or treat sepsis in a subject.

Method of Performing Liposuction Using Tumescent Antibiotic Solution

Some embodiments of TLAnti can be used to provide anesthesia, hemostasis, and antibiotic prophylaxis during liposuction or other medical procedures. Liposuction is a well-known procedure that is disclosed in U.S. Pat. Nos. 5,052,999 and 5,472,416, the disclosures of which are incorporated herein in their entirety by reference thereto. In the procedure disclosed herein, once the liposuction site is adequately sterilized and prepared, TLAnti is infiltrated into the subcutaneous fat compartment ("infiltration procedure") using a small gauge injection cannula, typically beginning at the location that the practitioner expects to be the deepest portion of adipose tissue removal. This area is filled with a sufficient quantity of TLAnti so that it becomes saturated and swollen or "tumescent." Typically, the operator can recognize whether sufficient TLAnti has been injected during the infiltration procedure if the area appears swollen, pale and relatively cool because of vasoconstriction. Once the practitioner has determined that sufficient TLAnti has been injected, the removal of adipose tissue can begin through a cannula capable of suctioning fat out of the body and into a reservoir. An example of such a procedure, albeit one involving standard tumescent anesthesia without the use of TLAnti is described in Jeffrey A. Klein, *Tumescent Technique Chronicles*, DERMATOLOGIC SURGERY, vol. 21, pp. 449-457, 1995.

The cannula typically used in such procedures include a tubular needle portion with proximal and distal ends. In some embodiments, the proximal end of the tubular needle is attached to a hub that is used by the anesthesiologist or surgeon to grasp and hold the cannula during the infiltration procedure. The hub is connected to the tubular needle at a first end and has a connector, such as a luer lock, at an opposing second end. The connector is, in turn, connected to a fluid source, such as tubing connected to a fluid reservoir containing the TLAnti such as an IV bag. The TLAnti enters via the connector. In some embodiments, the distal end of the cannula is sealed and the TLAnti exits the cannula through a plurality of apertures located proximate of the distal end in a linear, helical, or spiral pattern distributed over the distal 33% to 100% of the tubular needle. A detailed description of cannula of this type can be found in pending U.S. patent application Ser. No. 11/800,355. However, the present disclosure is compatible with a numerous types of cannula that are capable of being used in the infiltration procedure. Some examples can be found in U.S. Pat. Nos. 4,863,439, 6,336,925 and 7,018,354 the disclosures of which are incorporated by reference in their entirety by reference thereto. Such cannula are typically connected to a handle and a hollow tube that is operable coupled to a pumping system and receptacle for physiologic tissue and fluids.

In some embodiments, the TLAnti can be withdrawn from the reservoir and injected into the patient manually using a syringe, hand pump or electrical pumping system. In other embodiments, the TLAnti is injected from the reservoir using a peristaltic pump. One example of this type of pump can be found in U.S. Pat. No. 5,236,414, the disclosure of which is incorporated herein in its entirety by reference thereto. Another embodiment of a peristaltic pump that can be used with the current disclosure is described in pending U.S. patent application Ser. No. 11/641,228. Persons skilled in the art will recognize that there are a number of possible mechanisms that can be used to transfer the TLAnti from the reservoir to the subcutaneous fat compartment.

In some embodiments, the same cannula that is used for the removal of adipose tissue can be used for the delivery of TLAnti. In some such embodiments, the cannula can have two lumens, one for incoming adipose tissue and blood and a second lumen for outgoing TLAnti. In other embodiments, such cannula can have a single lumen that can be used alternatingly for the removal of adipose tissue and the injection of TLAnti. In such embodiments, the practitioner can switch the cannula from a mode wherein incoming adipose tissue and blood is being drawn into the cannula lumen, to an alternative mode wherein TLAnti passes out of the cannula lumen into the subcutaneous fat compartment. An example of such a switching system can be found in U.S. Pat. No. 4,696,669, the disclosure of which is incorporated herein in its entirety by reference thereto. Such embodiments can comprise separate pumping systems, for example, one for incoming tissue and fluid and another for the TLAnti. Other embodiments can utilize a single, reversible pumping system. An example of this technique, albeit one using standard tumescent anesthesia can be found in U.S. Pat. No. 5,472,416 the disclosures of which are incorporated herein in their entirety by reference thereto.

The Use of Tumescent Antibiotics in Mastectomy

TLAnti can be used during mastectomy procedures. The surgical excision of breast cancer is associated with a better prognosis than other therapeutic options such as chemotherapy, immunotherapy, endocrine therapy, or radiation therapy. However, surgery under general anesthesia is associated with significant systemic metabolic, neuroendocrine, and cytokine side-effects which may induce a transient perioperative inhibition of immune function including immune mediated anticancer surveillance thus enabling malignant cells to successfully spread to other parts of the body during the surgical procedure. Local anesthesia using the tumescent technique can reduce or prevent the immunosuppressive effects of general anesthesia. Lumpectomy and mastectomy are safer when performed by tumescent local anesthesia instead of general anesthesia. The tumescent technique also reduces or eliminates the need for postoperative narcotics which can inhibit immune function.

TLAnti can also help to reduce the risk of metastases by preventing malignant cells from entering the bloodstream through a number of mechanisms. The tumescent technique induces profound vasoconstriction, thus providing a physical barrier to malignant cells entering the blood stream and thereby reducing the risk of metastasis to distant organs. In addition, the use of TLAnti can reduce platelet activation which prevents endothelial wall retraction and reduces the likelihood of cancer cells entering the body. The surface of an activated platelet contains newly synthesized bioactive molecules including thromboxane $A_2$ and thrombin. Activated platelets may produce and release products which augment tumor cell survival and decrease the effectiveness of immune surveillance. High localized tissue concentrations of tumescent lidocaine inhibit platelet activation and thereby reduce the risk of surgery-precipitated metastasis.

In some embodiments, TLAnti is administered utilizing the Klein infiltration cannula (Klein cannula) described in pending U.S. patent application Ser. No. 11/800,355. Klein cannula are sealed on the distal end so that the TLAnti can exit the cannula from a series of apertures on the side of the cannula. This enables the operator to insert the cannula into the target area without the need for the operator to repeatedly push the cannula in and out of the surgical area during the infiltration procedure. By minimizing the amount of trauma to the treatment area and thereby reducing the risk of dislodging tumor cells, the likelihood of precipitating metastasis is reduced. In other embodiments, the procedure can be performed using cannula other than the Klein cannula.

The use of TLAnti during this procedure also adds the benefit of the administration of antibiotics during the surgical procedure. Just as in the liposuction procedures described above, surgical site infections can be problematic during mastectomy and lumpectomy. In addition to providing anesthesia and reducing the risk of metastasis, TLAnti can help to reduce the risk of surgical site infection. Some embodiments relate to the tumescent delivery of chemotherapeutic agents.

Some embodiments relate to the prevention of chronic pain after mastectomy or other surgical procedures by administration of TLAnti to achieve preemptive analgesia and reduce post-surgical pain. Use of TLAnti along with a Klein cannula can reduce the risk of chronic pain after mastectomy. Post-mastectomy pain syndrome (PMPS) is a common complication of breast surgery. The prevalence rate of PMPS is estimated to be 43%. In a study from Northeast Scotland, of 408 women who reported PMPS in 1996, nearly half continued to experience PMPS at a mean of 9 years after surgery. The most important factor associated with chronic pain and phantom pain after mastectomy is the intensity of acute post-operative pain. This fact suggests that aggressive management of acute postoperative pain may reduce chronic post-mastectomy pain. Preemptive surgical analgesia, such as can be achieved by tumescent delivery of local anesthetic, has been shown to reduce the degree and incidence of significant post-surgical pain. Preincisional paravertebral block (a form of local anesthesia) reduces the prevalence of chronic pain after mastectomy. However paravertebral blocks are relatively difficult achieve, require considerable clinical expertise, and are associated with a relatively high risk of systemic local anesthetic toxicity as a result of inadvertent IV injection. In contrast, the tumescent technique is relatively easy to perform with virtually no risk of toxicity associated with tumescent infiltration using a Klein cannula.

Additional Advantages of Using Tumescent Antibiotics in Surgical Procedures

TLAnti can be used in a variety of surgical procedures. When so employed, TLAnti can also reduce the risk of deep vein thrombosis and post-operative thromboembolism. Thromboembolism, a leading cause of perioperative morbidity and mortality, is the direct result of platelet activation by surgical trauma. There is both clinical and experimental evidence that lidocaine can reduce surgical trauma-associated platelet activation and aggregation. For example, in vivo bleeding volume and bleeding time tests show prolonged bleeding after local subcutaneous infiltration of tumescent local anesthesia containing dilute lidocaine, indicating a decrease in platelet activity. Blood platelet activation is associated with a degranulation and release of vasoactive and thrombogenic chemical mediators including serotonin and thromboxane-A2, which play a role in acute coronary thrombosis and arrhythmias. However, the lidocaine present in the TLAnti solution can affect platelet function by means of several diverse mechanisms: For example, the release of the phospholipid messenger lysophosphatidate from activated platelets is inhibited by the extracellular application of lidocaine in concentrations injected into surgical wounds. In addition, lidocaine may inhibit platelet aggregation by acting on adenosine diphosphate (ADP). Lidocaine, as well as other local anesthetics, benzocaine and bupivacaine, have been shown to inhibit platelet aggregation induced by ADP. In addition, at concentrations much higher than that required to decrease platelet aggregation, lidocaine inhibits the shape change associated with platelet aggregation. The actual mechanism of platelet inhibition by lidocaine is not known. Not wishing to be bound to a particular theory, however, the concentration of calcium ions may play a role in platelet inhibition by lidocaine and other local anesthetics. Lidocaine and bupivacaine have been shown to inhibit lysophosphate signaling, which induces Ca(2+)-activated Cl-currents. Thus, Lidocaine and bupivacaine may act to impair trans-membrane calcium transportation. In addition, there is evidence that increasing the concentration of calcium decreases the inhibitory effect of lidocaine on platelets.

The tumescent drug delivery system, in conjunction with tumescent local anesthesia and tumescent antibiotic delivery, is uniquely able to deliver long-lasting elevated lidocaine concentration to the site of surgical trauma and thereby prevent thromboembolism. Unlike other delivery systems, the tumescent technique is capable of producing sufficient concentrations for lidocaine to achieve its antithrombic effects. At safe systemic concentrations (e.g. ≤6 micrograms/ml) lidocaine seems to have no effect on platelet aggregation. However at tissue concentrations achieved after infiltration of TLAnti there is a significant inhibition of in-vitro platelet aggregation. In-vitro platelet aggregation induced by ADP, epinephrine and collagen is consistently inhibited by lidocaine concentrations equal to or greater than 0.5 mg/ml. The concentration of lidocaine in TLAnti typically ranges from 0.4 mg/ml to 1.2 mg/ml. Furthermore, in-vitro testing of the effect of lidocaine on platelet aggregation has shown that the longer the incubation time with lidocaine, the more efficient the anti-aggregating effect. The local tissue vasoconstriction associated with TLAnti impairs systemic absorption of tumescent lidocaine and dramatically prolongs the local tissue concentrations of lidocaine. Tumescent local anesthesia infiltrated into the site of surgical incision produces very high and prolonged local tissue concentrations of lidocaine and can thereby significantly reduce platelet activation and the risk of perioperative thromboembolism.

It is well known that thromboembolism is a greater risk with surgery under general anesthesia compared to the same surgery under local anesthesia. For example, comparisons of orthopedic surgical procedures of the knee done under general anesthesia versus procedures done under epidural/spinal regional local anesthesia show that the incidence of pulmonary embolism and deep vein thrombosis associated with the procedure is reduced. Lidocaine, a component of the regional local anesthesia used may have contributed to the reduction in thromboembolism observed. Circumstantial evidence also supports the potential role of TLAnti in preventing the occurrence of thromboembolism. When liposuction is performed under general anesthesia, pulmonary embolism is the leading cause of death. However, there have been no reported cases of pulmonary embolism associated with liposuction under tumescent local anesthesia.

In some embodiments, TLAnti may be delivered to the surgical site while the patient is under general anesthesia. Not wishing to be bound by a particular theory, the higher tissue concentration of lidocaine achieved with TLAnti may inhibit platelet function far more effectively than either IV delivery or peripheral nerve block delivery. The preoperative infiltration with of the surgical site with TLAnti enables the lidocaine concentration within surgically traumatized tissues to reach sufficiently high levels for the lidocaine to achieve an antithrombic effect. Thus TLAnti can reduce the risk of perioperative thromboembolic disease such as deep vein thrombosis (DVT) and pulmonary embolism (PE), while the systemic concentrations of lidocaine remain uniformly well below the toxic threshold.

In some embodiments, lidocaine provided in TLAnti may act synergistically with other antibiotics to decrease the risk of surgical site infection. Lidocaine is known to affect nerve conduction by inhibiting cell membrane sodium pumps. Not wishing to be bound to a particular theory, it is likely that lidocaine exerts its antibiotic affect through inhibition of trans-membrane ion transport or antibiotic efflux channels. Synergy between lidocaine and other antibiotics, such as cefazolin or metronidazole, is tested by performing minimum inhibitory concentration (MIC), minimum bactericidal concentration (MBC), and Time-Kill studies involving methacillin-resistant *Staphylococcus aureus*, *Bacteroides fragilis*, and *Escherichia coli*.

Several embodiments relate to methods and compositions for reducing the risk of thromboembolism by oral administration of lidocaine. The bioavailability of orally administered lidocaine is limited by rapid degradation of lidocaine by cytochrome P450 enzymes. Several embodiments described herein relate to methods of reducing the risk of thromboembolism by oral administration of lidocaine in combination with an inhibitor of cytochrome P450 enzymes. Examples of cytochrome P450 inhibitors include free bases or pharmacologically acceptable salts of: alpha-naphthoflavone, beta-naphthoflavone, apigenin, baicalein, beta-myrcene, catechin, 3-phenylpropyl acetate, formononetin, gallic acid, hesperetin, hesperidin, isoquercitrin, lauryl alcohol, luteolin, luteolin-7-glycoside, narigin, nordihydroguaiaretic acid, quercitrin, swertiamarin, terpineol, and trans-cinnamaldehyde. Lidocaine and one or more cytochrome P450 inhibitors may be administered simultaneously or sequentially.

The Use of Tumescent Antibiotics in Emergency Medical Procedures

TLAnti can be delivered using a disposable, plastic cannula as described in U.S. patent application Ser. No. 11/800,355, the disclosures of which are incorporated herein in their entirety by reference thereto. This device provides a method for relatively rapid fluid resuscitation and the administration of anesthesia and antibiotics in situations wherein establishing intravenous (IV) access is not feasible (e.g., in a remote area, an obese patient with poor venous access, burn/trauma victim, unavailable trained medical professional, etc.). A significant advantage of using the tumescent technique to deliver fluids and medications is that the infiltration procedure is relatively easy to perform. This can make it a particularly valuable technique, for example, in the setting of overwhelming mass casualties where there is no hope or expectation of trained clinical personnel being available. In such cases, the ability of untrained first-responders to provide immediate fluid resuscitation can save many lives. Such situations can include disasters with overwhelming numbers of trauma or burn victims, or when a cholera epidemic results in widespread dysentery and dehydration, in conditions of biological warfare or widespread radiation exposure, etc. It is unlikely that under such conditions, there will be sufficient trained personnel to start an IV line for IV fluid resuscitation. In such a setting, anyone (e.g., an adult of average intelligence with minimal clinical training), perhaps even a victim himself, could simply insert one or more disposable plastic infiltration cannula directly through the skin on the thigh(s) and into subcutaneous tissue, attach an IV bag and allow the force of gravity to propel the TLAnti into the subcutaneous space in a tumescent fashion. In a setting where rapid systemic absorption of fluids and systemic absorption of antibiotics is critical to resuscitation of a patient with dehydration and an infection, the tumescent antibiotic solution can be modified by eliminating a vasoconstrictor such as epinephrine, and instead adding a vasodilator such as methyl nicotinate. The resulting systemic absorption and redistribution of TLAnti into the intracellular and intravascular compartments could be life-saving.

The tumescent technique performed with disposable catheters and TLAnti provides a useful method of administering fluids and medications to patients when establishing an IV line is difficult or impossible. For example, it can be extremely difficult to obtain IV access among patients who are obese, elderly, have a history of IV drug abuse, or with severe dehydration. By contrast, the subcutaneous infiltration of medications using the tumescent technique can often be achieved relatively easily in many such cases. In such cases, the ability to administer IV fluids, anesthetic, and antibiotics through the alternative subcutaneous route can be invaluable and, at times, lifesaving. The use of tumescent drug delivery for emergency fluid resuscitation when IV access is not feasible has been previously described in U.S. Pat. No. 7,572,613 the disclosure of which is incorporated herein in their entirety by reference thereto.

The tumescent technique can also be useful in certain conditions where various aspects of the environment make IV insertion difficult or impractical. Such conditions could include the treatment of wounded soldiers in night-time combat conditions when establishing an IV access in total darkness is nearly impossible and the use of a flash light might attract enemy fire. It could also be useful in low gravity environments, such as on the International Space Station where a normal gravity-fed IV could not function, but injecting medications subcutaneously using the tumescent technique would not be affected. Cannula with pre-mixed dosages of TLAnti could be provided in emergency medical kits for use in such conditions if and when the need arises.

Methods of Conducting Pharmacokinetic Measurements of Interstitial Space Fluid

It is important to reach pharmacologically active drug concentrations at the site of action for effective treatment of infectious diseases. Since the interstitial space fluid (ISF) of tissue represents the site of action for a majority of bacterial infections and since only free (unbound) molecules account for the drug effect, direct measurement of the free drug fraction in ISF is desirable. However, it is considerably more challenging to conduct pharmacokinetic measurements of interstitial space fluid (ISF) than serum. For example, measurements of extravascular antibiotic concentrations using excised tissue is problematic because tissue homogenates contain blood, intracellular organelle-bound, and protein-bound drug concentrations, which differ significantly from the concentrations of antibiotics within ISF, which is relatively blood and protein free. Recently, clinical pharmacologic studies of antibiotics have used microdialysis to determine drug concentrations in ISF; however, at present microdialysis technology is complex, expensive and not widely available.

Several embodiments described herein relate to a novel method for conducting pharmakinetic measurements of ISF by sequential sampling of tumescent interstitial space fluid (TISF). Several embodiments relate to a method of conducting pharmakinetic measurements of one or more drugs in ISF comprising obtaining from subcutaneous adipose tissue sequential samples of TISF by hand-held syringe liposuction for a period of time after tumescent delivery of the one or more drugs and measuring the amount of one or more drugs in each sample. In some embodiments, sequential sampling of TISF is conducted hourly, every two hours, every three hours, every four hours, every five hours, every six hours, every seven hours, every eight hours, every nine hours, or every ten hours for up to 2, 3, 4, 5, 6, 7, 8, 9, 10, 11, 12, 13, 14, 15, 16, 17, 18, 19, 20, 21, 22, 23, 24, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, or 68 hours. In some embodiments, the methods described herein may be used to investigate the absorption pharmacokinetics of antibiotics.

Several embodiments described herein relate to a novel method for conducting pharmakinetic measurements of one or more antibiotics in ISF comprising obtaining sequential samples of TISF from subcutaneous adipose tissue by hand-held syringe liposuction for a period of time after tumescent delivery of TLAnti solution and measuring the amount of the one or more antibiotics in each sample. In some embodiments, a sample of TISF is obtained every 5, 10, 15, 20, 25, 30, 35, 40, 45, 50, or 55 minutes after TAD. In some embodiments, a sample of TISF is obtained hourly after TAD. In some embodiments, a sample of TISF is obtained every 2, 3, 4, 5, 6, 7, 8, 9, 10, 11, 12, 13, 14, 15, 16, 17, 18, 19, 20, 21, 22, 23, or 24 hours after TAD. In some embodiments, sequential samples of TISF are obtained for a period of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, or 68 hours after TAD. One embodiment relates to a method of conducting pharmakinetic measurements of one or more antibiotics in ISF comprising obtaining a sample of TISF hourly for a period of 10 hours after TAD and measuring the amount of one or more antibiotics in each sample.

Since only free (unbound) antibiotic molecules account for the antimicrobial effect, determination of the free antibiotic fraction in ISF is desirable. The concentration of free (unbound) antibiotic in TISF after tumescent antibiotic delivery can reasonably be assumed to be equivalent to the entire antibiotic content in TISF (i.e., total[TISF]TAD≈free[TISF]TAD) because the antibiotic concentration of TAD solution is high, while the protein content of TISF is low. For intravenous antibiotic delivery, the physiology of molecular osmosis, where free (unbound) antibiotic molecules move without restriction across capillary walls, results in an equilibrium of free antibiotic in the serum and extra-vascular interstitial fluid (ISF) (free[ISF]IVAD≈free[Serum]IVAD).

The methods described herein may be utilized to measure important pharmacokinetic (PK) metrics for bioavailability of drugs, such as antibiotics, within subcutaneous adipose tissue, such PK metrics including: area under the curve of concentration as a function of time (AUC) and the maximum concentration (Cmax) of the drug. The magnitude of the cumulative tissue exposure a tissue over time to a given drug can be measured by determining the AUC of drug concentration within the interstitial fluid (ISF) as a function of time. With regard to the PK metrics of antibiotics, the methods described herein may further be utilized to measure the duration of time that the antibiotic concentration exceeds the minimal inhibitory concentration (MIC) for a specific bacteria (T>MIC).

The methods described herein may be utilized to evaluate the effectiveness of tumescent drug delivery compared to other modes of delivery. For example, in one embodiment, the methods described herein may be utilized to evaluate the effectiveness of tumescent antibiotic delivery (TAD) and intravenous antibiotic delivery (IVAD) for preventing surgical site infection (SSI). Only free (unbound) antibiotic molecules interact with bacteria or diffuse across capillary walls between serum and ISF; thus, for SSI prevention, the most effective modes of antibiotic delivery would result in the greatest free-antibiotic concentration in subcutaneous ISF. Accordingly, TAD is superior to IVAD for preventing SSIs where free[ISF]IVAD<free[TISF]TAD. Since the total concentration of antibiotic is equivalent to free (unbound) antibiotic in TISF after tumescent antibiotic delivery and the concentrations of free antibiotic in the serum and ISF are equivalent after IVAD, then TAD is superior to IVAD for preventing SSIs where experimental data demonstrates total [Serum]IVAD<total[TISF]TAD.

Definitions

Adit: a small round hole in the skin (typically 1 mm, 1.5 mm or 2 mm diameter) made by a skin-biopsy punch, and intended to be an access port for percutaneous entry into the subcutaneous fat by a tumescent infiltration cannula and/or a liposuction cannula.

Infiltration: an injection that causes a fluid to permeate or percolate through pores and/or interstices. Thus an infiltration refers to an injection directly into tissue.

Infusion: an injection that pours a fluid into a place or into the lumen of a blood vessel. Thus an infusion refers to an intravascular injection.

Injection: The action of forcing a fluid, etc. into tissue or cavity, as by means of a syringe, or by some impulsive force.

Tumescent Technique, Tumescent Infiltration: The tumescent technique is a method of subcutaneous drug delivery of large volumes of very dilute solution of a medication together with either a dilute vasoconstrictor such as epinephrine or a dilute vasodilator such a methyl nicotinate in an isotonic solution of crystalloid (e.g. physiologic saline, lactated Ringer's solution, Hartman's solution) infiltrated directly into subcutaneous fat or muscle or along the exterior of a length of vein or other tissue to produce either a vasoconstrictor-induced very slow systemic absorption or a vasodilator-induced rapid systemic absorption, as well as direct hydrostatic effect on capillaries, veins, and arterioles. The tumescent technique can be used to deliver large volumes of very dilute medication together with dilute epinephrine in isotonic solution of crystalloid (e.g., physiologic saline, lactated Ringer's solution, Hartman's solution, etc). Inclusion of a vasoconstrictor in the tumescent solution produces very slow systemic absorption as a result of intense subcutaneous vasoconstriction, as well as direct hydrostatic compression of capillaries and veins.

Minimum Bactericidal Concentration (MBC) is the lowest concentration of antibiotic required to kill a particular bacterial isolate in vitro. Antimicrobials are usually regarded as bactericidal if the MBC is no more than four times the MIC.

Minimum Inhibitory Concentration (MIC) is the lowest concentration of an antimicrobial that will inhibit the visible growth of a particular bacterial isolate. Measurements of MIC are used to confirm resistance of microorganisms to an antimicrobial agent and also to monitor the activity of new antimicrobial agents. Clinically, the minimum inhibitory concentrations may be used not only to determine the amount of antibiotic that the patient will receive but also the type of antibiotic used, which prevents the development of microbial resistance to antimicrobial agents.

Tumescent Drug Delivery, Tumescent Delivery: Tumescent drug delivery and synonyms refer to the tumescent technique for delivering a drug into the subcutaneous space. In other words, tumescent delivery is a process of infiltration of very large volumes of very dilute solutions of therapeutic substances dissolved in a crystalloid solution with either a vasoconstrictor such as epinephrine or a vasodilator such as methyl nicotinate into subcutaneous tissue to the point of producing tumescence of the targeted tissue.

Tumescent Local Anesthesia (TLA) is local anesthesia produced by direct infiltration into subcutaneous tissue of large volumes of dilute local anesthetic.

Tumescent Local Anesthetic Solution (TLA Solution) is the local anesthetic solution used to produce TLA. Several embodiments relate to a TLA solution comprising an antibiotic component, an anesthetic component, a vasoconstrictor component and a solvent. In some embodiments, TLA Solution consists of a 10 to 20 fold dilution of commercially available concentration of lidocaine and epinephrine. In one embodiment, TLA Solution comprises very dilute lidocaine ≤1 gram/liter) and epinephrine (≤1 milligram/liter) with sodium bicarbonate (10 milliequivalents/liter) in a crystalloid solution such as physiologic saline or lactated Ringer's solution. Typically the volume of TLA Solution infiltrated into the target tissue is so large that the skin and subcutaneous tissue becomes tumescent, in other words swollen and firm.

As used herein, the terms "tumescent local antibiotic solution," "TLAnti solution," "tumescent antibiotic delivery solution," or "TAD solution," may be used interchangeably to refer to a solution comprising an antibiotic component, an anesthetic component, a vasoconstrictor component and a solvent/pharmaceutically acceptable carrier.

Tumescent, tumescence: swollen and firm.

Tumescent liposuction: liposuction performed by local anesthesia using tumescent local anesthesia.

Tumescent fluid, tumescent solution: dilute solutions of therapeutic substances dissolved in an aqueous solvent, such as crystalloid solution, intended for tumescent delivery into subcutaneous tissue.

Tumescent "drug": the "drug" in the context as an ingredient in a tumescent solution and its pharmacokinetic behavior as a result of the pharmacokinetics of a tumescent solution; for example tumescent lidocaine, tumescent epinephrine, tumescent antibiotic.

Tumescent Pharmacokinetics: The absorption pharmacokinetics (the pharmacologic and physiologic factors associated with the systemic absorption of a drug) after tumescent infiltration of a drug is either dramatically slower with a vasoconstrictor such as epinephrine or dramatically faster with a vasodilator such as methyl nicotinate than the rate of systemic absorption of routine injection of the drug. In some embodiments, the intense vasoconstriction induced by epinephrine, slows the rate of drug absorption into the central circulation and prolongs the local effects of the drug. For example, the duration of routine local anesthesia with lidocaine is typically 2 hours; in contrast the duration of tumescent local anesthesia may be 12 to 18 hours or more. A similar prolonged effect of tumescent antibiotic infiltration significantly improves the prophylactic effect of preoperative antibiotic therapy in the prevention of surgical site infections.

As used herein, the term "[FLUID]MODE" refers to the concentration of a drug (e.g., an antibiotic) in a specified FLUID, for example, interstitial fluid, blood serum, whole blood, amniotic fluid, aqueous humour, breast milk, cerebrospinal fluid, lymph, peritoneal fluid, pleural fluid, saliva, sweat, mucus, etc., after a specified MODE of drug delivery. Examples of MODES of drug delivery include, but are not limited to ingestion, topical administration, transmuscosal administration, inhalation, injection, intravenous administration, intrarterial administration, intramuscular administration, intraosseous administration, intrathecal administration, intraperitoneal administration, intravesical administration, intravitreal administration, intradermal administration, and tumescent administration. As used herein, [ISF]IVAD and [Serum]IVAD represent the antibiotic concentration in interstitial fluid (ISF) and serum, respectively, after IVAD. Similarly, [TISF]TAD and [Serum]TAD refer to the antibiotic concentrations in TISF and serum after TAD.

As used herein, the term "bound[FLUID]MODE" refers to the concentration of protein bound drug (e.g., antibiotic) in the specified FLUID after delivery by a specified MODE.

As used herein, the term "free[FLUID]MODE" refers to the concentration of free drug (e.g., antibiotic) (not bound to protein) in the specified FLUID after delivery by a specified MODE.

As used herein, the term "pharmacodynamic quantity" refers to a quantitative measure of drug effect in terms of drug concentration as a function of time. For example, the terms "area under the curve (AUC)" and "time to Cmax" refer to pharmacokinetic quantities.

As used herein, the term "Cmax" refers to the peak drug (e.g., antibiotic) concentration in a tissue after drug delivery. As used herein, the term "Cmax[FLUID]MODE" refers to the peak drug (e.g., antibiotic) concentration in a specified FLUID after delivery by a specified MODE.

As used herein, the term "T(Cmax)" refers to the time from initiation of drug (e.g., antibiotic) delivery to the time when Cmax is achieved.

As used herein, T>MIC refers to the length of time during which the drug concentration exceeds the Minimum Inhibitory Concentration (MIC) for a given pathogen. As used herein, T[TISF]TAD>MIC refers to the length of time the antibiotic concentration exceeds the MIC for a given bacteria in Tumescent Interstitial Space Fluid (TISF) after TAD.

As used herein, the term "interstitial space fluid (ISF)" refers to an extracellular and extravascular fluid that fills the spaces between most of the cells of the body. ISF is relatively blood and protein free.

As used herein, the term "Tumescent Interstitial Space Fluid (TISF)" refers to a mixture of a small volume of ISF and a larger volume of tumescently-delivered solution, for example, TLA Solution, TLAnti Solution, TAD solution, etc., said mixture resulting from tumescent infiltration. Immediately after tumescent infiltration, TISF is chemically equivalent to the TAD solution.

As used herein, the term "Minimum Inhibitory Concentration (MIC)" refers to the lowest concentration of a drug (e.g., an antimicrobial) that will inhibit the visible growth of a pathogen (e.g., a microorganism) after overnight incubation. MIC is a function of both the pathogen and the drug under consideration.

As used herein, the term "area under the curve (AUC)" is a pharmacokinetic term that refers to drug concentration as a function of time following drug delivery. AUC is calculated from the area under the plot of body fluid concentration of drug (not logarithm of the concentration) against time after drug administration. The AUC is of particular use in estimating bioavailability of drugs, and in estimating total clearance of drugs. Area under the curve (AUC) of drug concentration within blood or tissue as a function of time is a pharmacokinetic metric for measuring the magnitude of the cumulative tissue exposure over time to a given drug. Whenever drug concentration is measured continuously then AUC is defined as $AUC = \int_0^{t_n} C(\tau)$ evaluated from time $t=0$ to $t_n$. Whenever drug concentration is measured at discrete time points $\{t_0, t_1, t_2, \ldots, t_n\}$, AUC can be estimated using the trapezoid rule:

$$AUC = \sum_{i=t}^{i=n} \frac{[C(ti) + C(t(i-1))]}{2} (t(i) - t(i-1)).$$

As used herein, the term "AUC[FLUID]MODE" refers to the AUC of the drug in a specified body FLUID by a specified MODE. For example, the term "AUC[ISF]TAD" refers to the AUC in interstitial space fluid of the drug administered by tumescent delivery; the term "AUC[Serum]TAD" refers to the AUC in serum of the drug administered by tumescent delivery; the term "AUC[ISF]IVAD" refers to the AUC in interstitial space fluid of the drug administered by IV delivery; and the term "AUC[Serum]TAD" refers to the AUC in serum of the drug administered by IV delivery.

Each antibiotic has a characteristic fraction of its total concentration which is bound to proteins. Only free antibiotic molecules interact with bacteria or diffuse across capillary walls between serum and ISF. As used herein, the term "freeAUC[TISF]TAD" refers to the AUC of free (unbound) antibiotic in ISF after TAD. As used herein, the term "totalAUC[Serum]IVAD" refers to the AUC of total (bound and unbound) antibiotic in Serum after IVAD. Similarly, a fraction of an antibiotic in ISF is protein bound.

As used herein, the term "patient" refers to the recipient of a therapeutic treatment and includes all organisms within kingdom animalia. In preferred embodiments, the animal is within the family of mammals, such as humans, bovine, ovine, porcine, feline, buffalo, canine, goat, equine, donkey, deer and primates. The most preferred animal is human.

As used herein, the terms "treat" "treating" and "treatment" include "prevent" "preventing" and "prevention" respectively. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

The term "effective amount" includes an amount effective, at dosages and for periods of time necessary, to achieve the desired result, e.g., sufficient to prevent thromboembolism or infection. An effective amount of TLAnti or other tumescent solution may vary according to factors such as the disease state, age, and weight of the subject, and the ability of TLAnti or other tumescent solution to elicit a desired response in the subject. Dosage regimens may be adjusted to provide the optimum therapeutic response. An effective amount is also one in which any toxic or detrimental effects (e.g., side effects) of TLAnti or other tumescent solution are outweighed by the therapeutically beneficial effects. The language "a prophylactically effective amount" of TLAnti refers to an amount of TLAnti which is effective, upon single or multiple dose administration to the subject, in preventing or treating infection or thromboembolism.

All documents, or portions of documents, cited in this application, including but not limited to patents, patent applications, articles, books, and treatises, are hereby expressly incorporated by reference in their entirety for any purpose.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved.

As used herein, an "increase" or "decrease" in a measurement, unless otherwise specified, is typically in comparison to a baseline value. For example, an increase in time to hospitalization for subjects undergoing treatment may be in comparison to a baseline value of time to hospitalization for subjects that are not undergoing such treatment. In some instances an increase or decrease in a measurement can be evaluated based on the context in which the term is used.

The following are provided for illustrative purposes only, and are in no way intended to limit the scope of the present invention.

EXAMPLES

Example 1

Clinical Evaluation of Tumescent Antibiotic Delivery

With IRB-approval, 4 subjects received Cefazolin IV Antibiotic Delivery (IVAD) or Tumescent Antibiotic Delivery (TAD) on repeated occasions. One patient received Metronidazole and Cefazolin.

TAD was achieved using blunt-tipped Monty infiltration cannula and peristaltic tumescent infiltration pump. Treated areas included: abdomen (Patient 1 & Patient 4); female breasts (Patient 2); and hips-outer thighs (Patient 3). Patient 4 received Cefazolin and Metronidazole.

Figure 8:
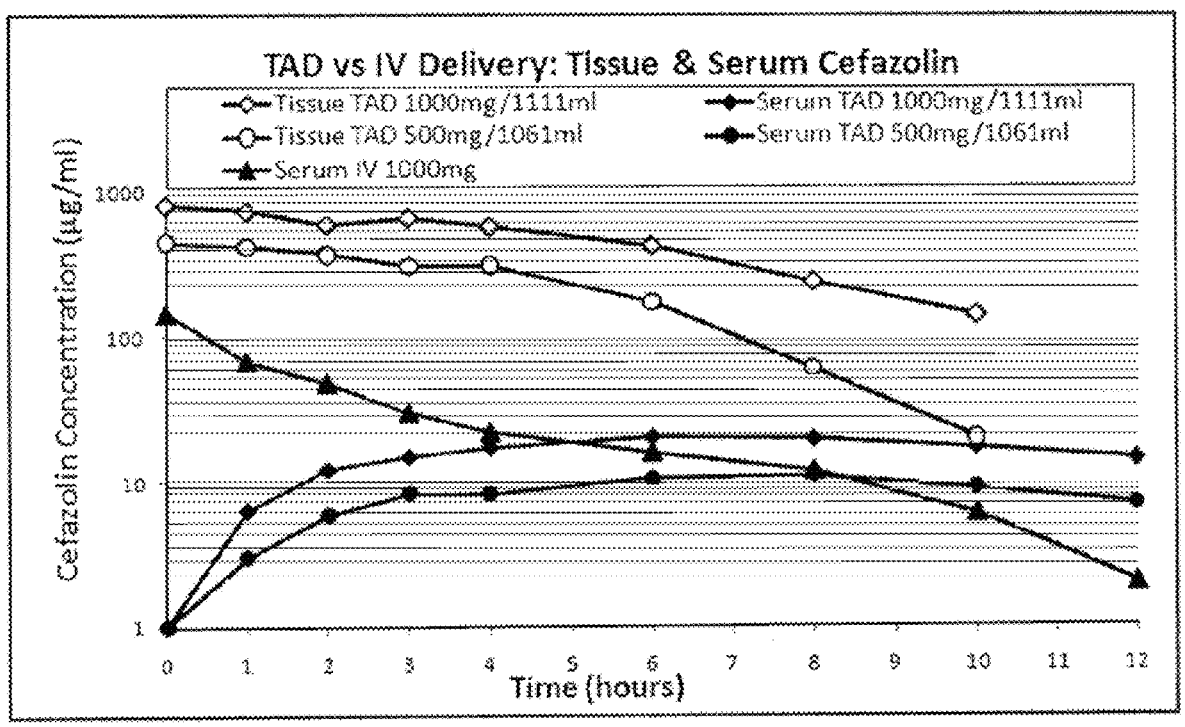
FIG. 8 shows the results of a comparison study of tumescent antibiotic delivery (TAD) versus IV delivery of Cefazolin.
Figure 9:
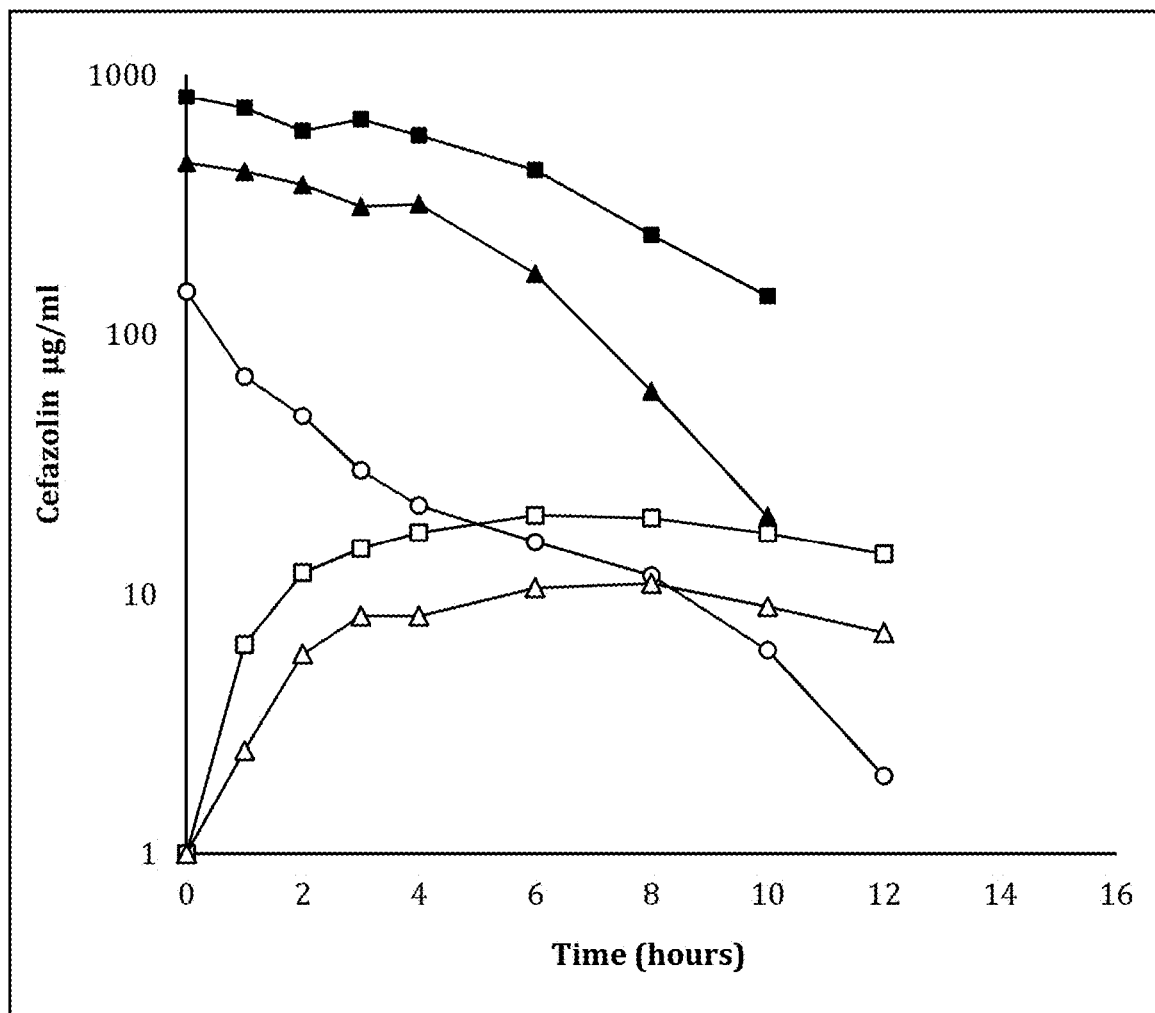
FIG. 9. Cefazolin log-linear concentration vs time profiles following one IV antimicrobial delivery (IVAD) and two tumescent antimicrobial deliveries (TAD). The IVAD dose was 1000 mg. The TAD doses were both 1000 mg, but the cefazolin concentrations in the TAD solutions were different at 900 mg/L and 450 mg/L. Following subcutaneous TAD of a solution containing 900 mg/L, the bioavailability in tumescent interstitial fluid (TISF) was AUC∞=5349. This was 16.5 times greater than the bioavailability in serum following IVAD, AUC∞=324. Doubling the cefazolin mg/L concentration in the tumescent solution, at a constant mg dose, doubles the Cmax in TISF and increases the subsequent cefazolin concentrations in serum at every time point.
Figure 10:
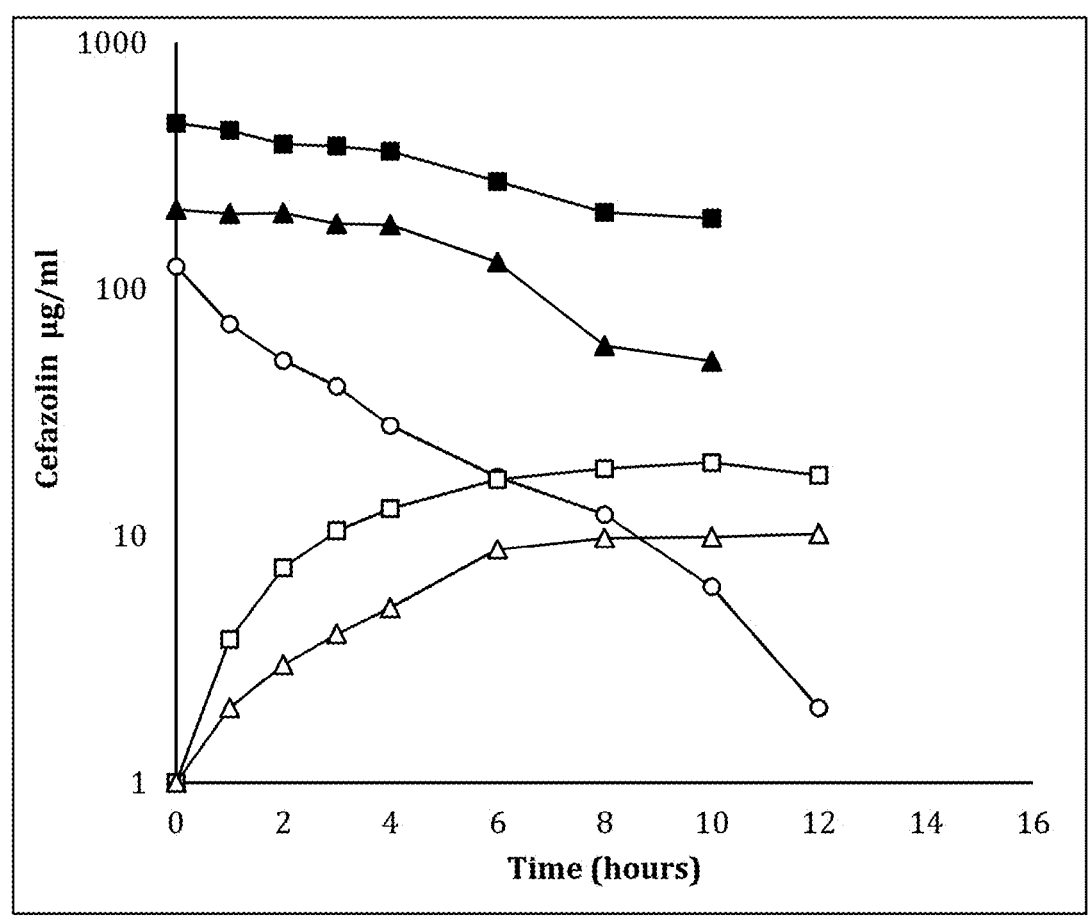
FIG. 10. Cefazolin log-linear concentration vs time profiles following one IV antimicrobial delivery (IVAD) and two tumescent antimicrobial deliveries (TAD). The IVAD dose was 1000 mg. Both TAD doses were 500 mg, but cefazolin concentrations in the TAD solutions were different at 450 mg/L and 225 mg/L. Following subcutaneous TAD of a solution containing 450 mg/L tumescent solution, the bioavailability in tumescent interstitial fluid (TISF) was AUC∞=4071. This was 12 times greater than the bioavailability in serum following IVAD, AUC∞=340. Doubling the antibiotic concentration in the TAD solution doubles the Cmax in TISF and increases the subsequent cefazolin concentrations in serum at every time point.
Figure 11:
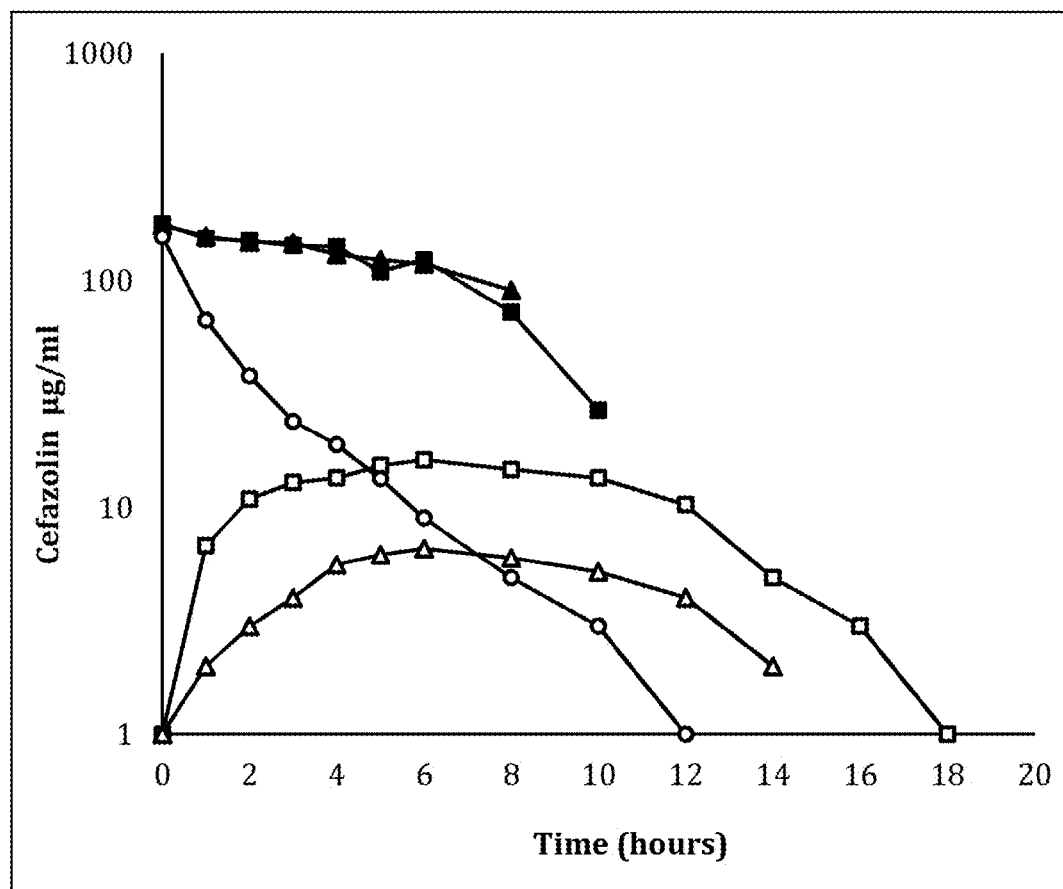
FIG. 11. Cefazolin log-linear concentration vs time profiles following one IV antimicrobial delivery (IVAD) and two tumescent antimicrobial deliveries (TAD). The IVAD dose was 1000 mg. The two TAD doses were different. 870 mg and 435 mg but the concentrations in the TAD solution were constant at 228 mg/L. When the antibiotic concentration in the TAD solutions were held constant, but the total mg dose of cefazolin was doubled from 435 mg (into one hip & outer thigh) to 870 mg (into both hips & outer thighs) the Cmax and the cefazolin concentration-time profiles in tumescent interstitial fluid (TISF) were identical. Increasing the mg dose of cefazolin (from 435 mg to 870 mg) by TAD increases its concentration in serum at every time point.
Figure 12:
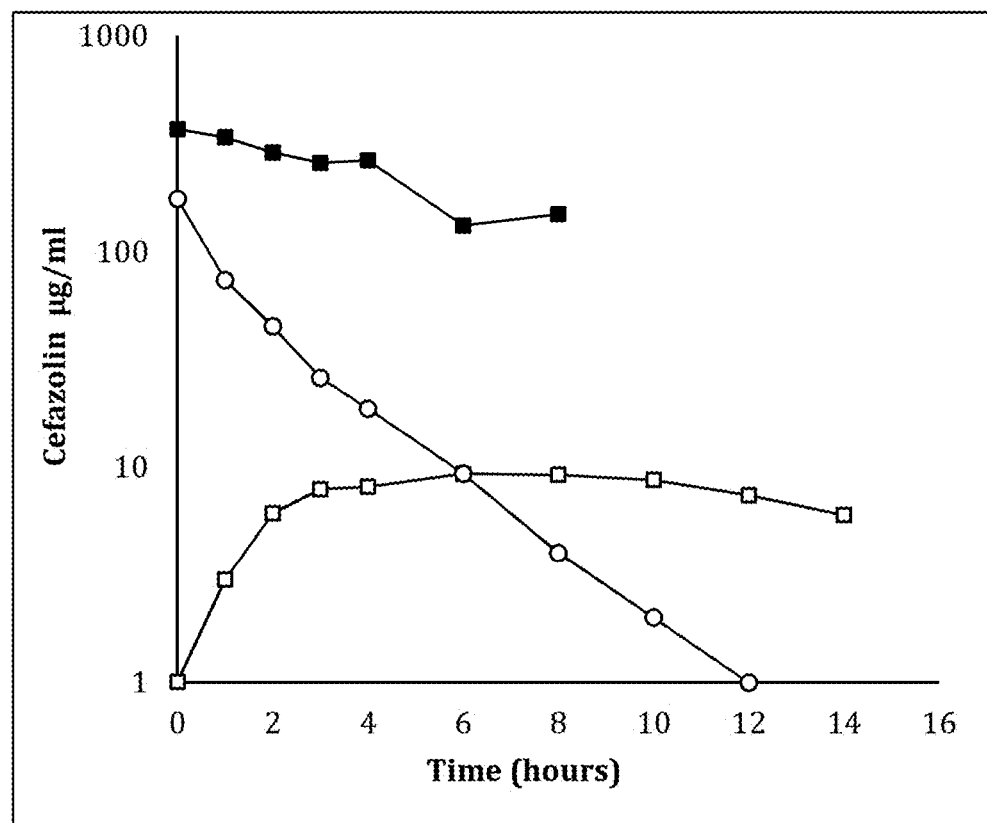
FIG. 12. (A) Cefazolin log-linear concentration vs time profiles following one IV antimicrobial delivery (IVAD) and one tumescent antimicrobial delivery (TAD). The IVAD solution contained equal 500 mg doses of cefazolin and metronidazole. The TAD solution contained equal 500 mg doses and equal 413 mg/L concentrations of cefazolin and metronidazole. (B) Metronidazole log-linear concentration vs time profiles following one IV antimicrobial delivery (IVAD) and one tumescent antimicrobial delivery (TAD). The IVAD solution contained equal 500 mg doses of metronidazole and cefazolin. The TAD solution contained equal 500 mg doses and equal 413 mg/L concentrations of metronidazole and cefazolin. (C) Log-linear concentration-time profiles of cefazolin and metronidazole. When equal 500 mg doses of cefazolin (open circles) and metronidazole (open diamonds) were given by IV antimicrobial delivery, the concentration-time profiles in serum were significantly different. In contrast, when equal doses and concentrations of cefazolin (closed squares) and metronidazole (closed triangles) were given by tumescent antimicrobial delivery, the concentration-time profiles in tumescent interstitial fluid were identical.
Figure 12:
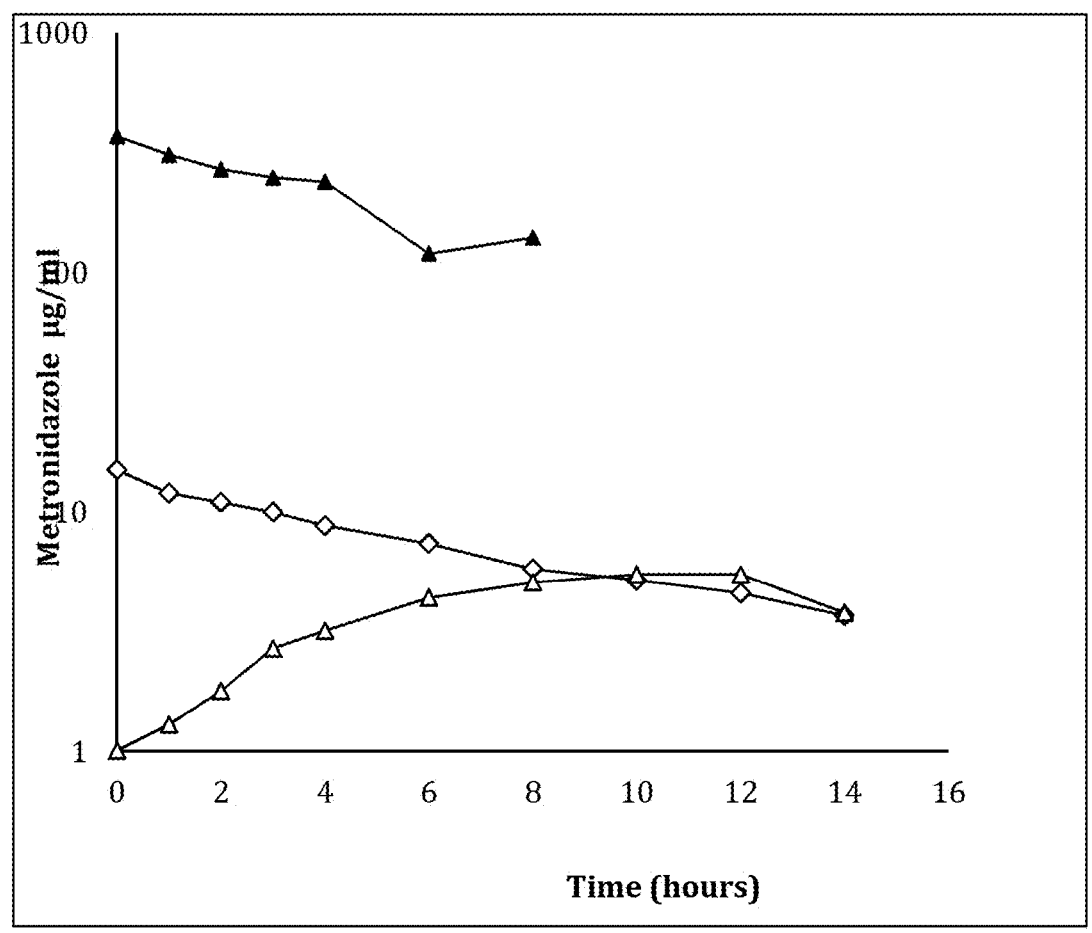
Figure 12:
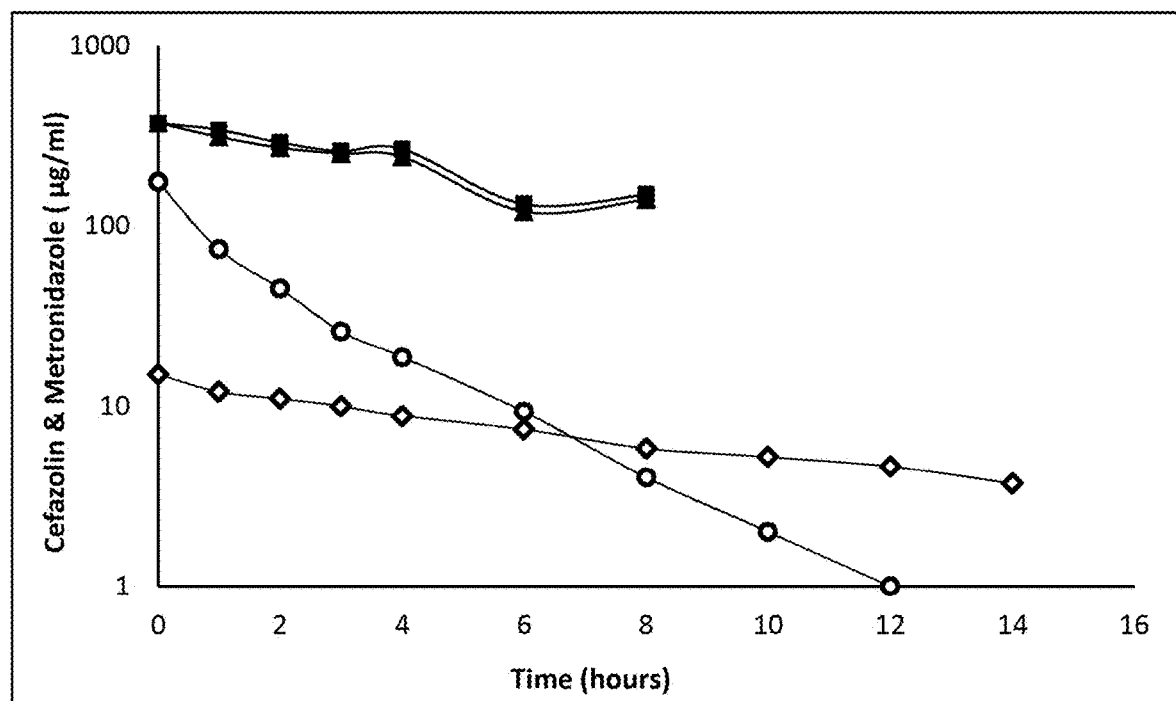
Figure 13:
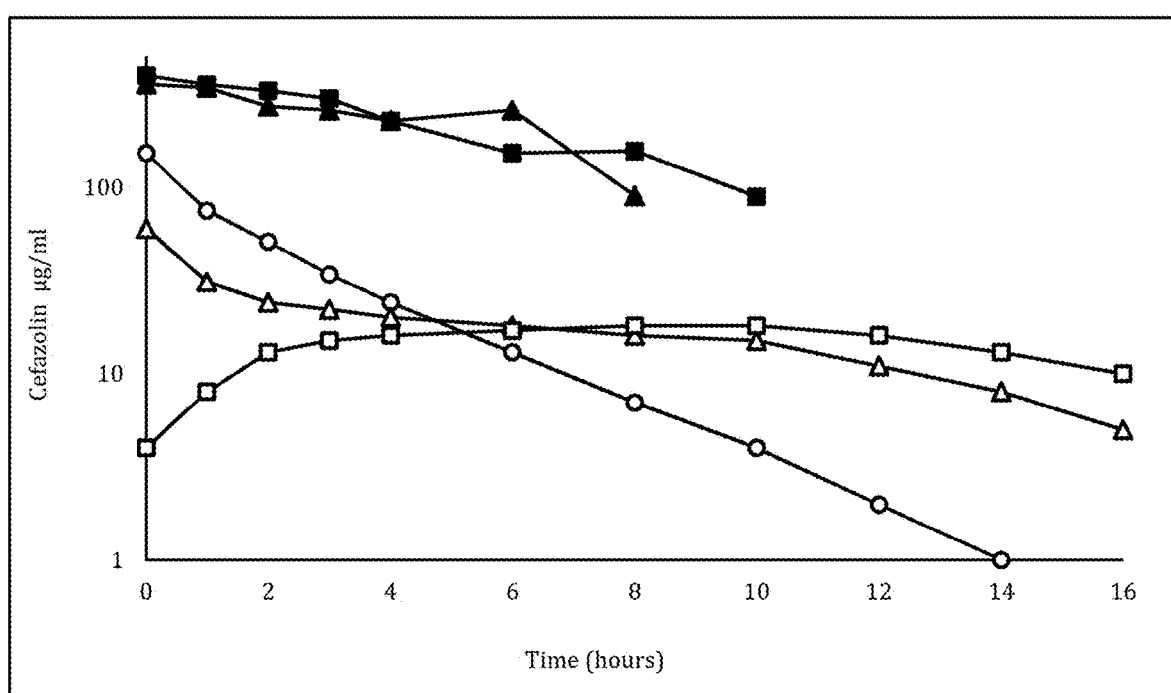
FIG. 13. (A) Antibiotic log-linear concentration-time profiles of cefazolin comparing tumescent antimicrobial delivery (TAD) alone with IV antimicrobial delivery (IVAD) alone and with concomitant TAD+IVAD. When 1200 mg of cefazolin was simultaneously delivered by TAD (800 mg) and by IVAD (400 mg), the Cmax for cefazolin in subcutaneous TISF was 9.2 times higher than in serum following 1200 mg of cefazolin delivered by IVAD alone. (B) Antibiotic log-linear concentration-time profiles of metronidazole comparing tumescent antimicrobial delivery (TAD) alone with IV antimicrobial delivery (IVAD) alone and with concomitant TAD+IVAD. When 600 mg of metronidazole was simultaneously delivered by TAD (400 mg) and by IVAD (200 mg), the Cmax for metronidazole in subcutaneous TISF was 10 times higher than in serum following 600 mg of metronidazole delivered by IVAD alone.
Figure 13:
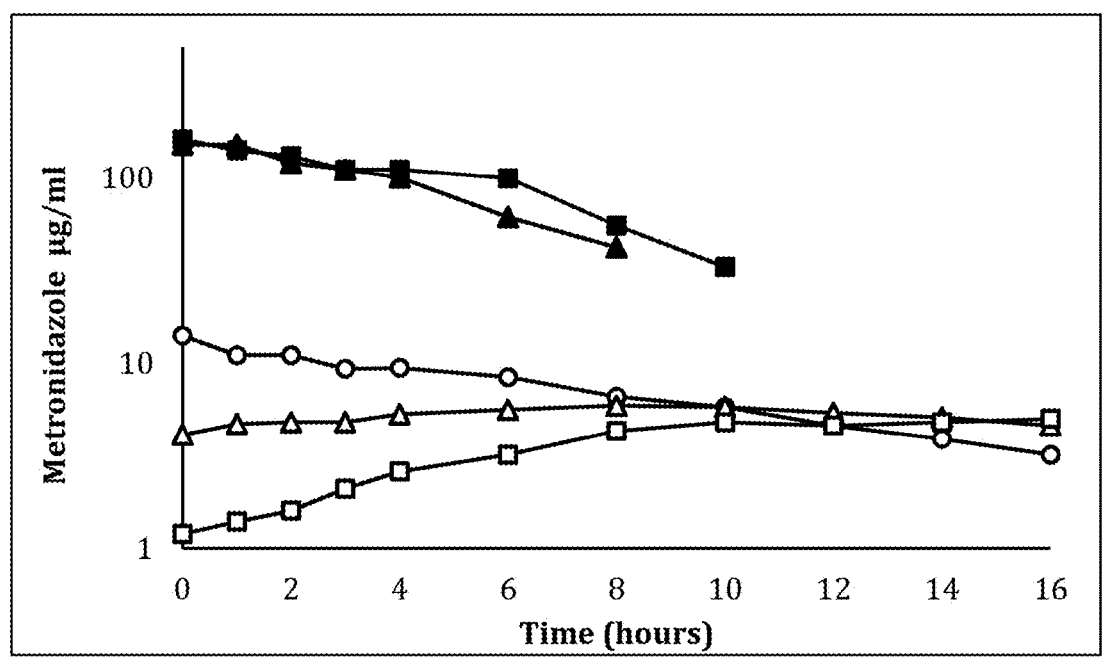

After TAD or IVAD treatment, blood was sampled at 1 to 2 hour intervals for a period of ≥12 hours. After TAD treatment, samples of subcutaneous fat/tumescent fluid were aspirated by hand-held syringe-liposuction at 1 to 2 hrs for a period of ≥8 hrs. Samples were centrifuged. Serum and subcutaneous interstitial tissue fluid were assayed for Cefazolin or Metronidazole by HPLC. Results are shown in FIG. 8.

Patient 1 was studied on 3 separate occasions with treatments occurring at least one week apart. Patient 1 was treated with: TAD 1000 mg Cefazolin/1111 ml; TAD 500 mg Cefazolin/1061 ml; or IVAD 1000 mg Cefazolin. The 10 hour Cefazolin AUC and Cmax for TAD (abdomen) and IVAD treatments for Patient 1 are shown in Table 1. Other patients studied gave similar results (not shown).

TABLE 1

| 10 HOUR CEFAZOLIN AUC AND CMAX FOR TAD (ABDOMEN) & IVAD | | |
|---|---|---|
| Sample | AUC | Cmax |
| Subcutaneous Cefazolin (TAD 1000 mg) | 4782 | 823 |
| Subcutaneous Cefazolin (TAD 500 mg) | 2280 | 456 |
| Serum Cefazolin (TAD 1000 mg) | 167 | 20 |
| Serum Cefazolin (TAD 500 mg) | 82 | 11 |
| Serum Cefazolin (IV 1000 mg) | 315 | 146 |

AUC Ratio TAD 1000 mg: IV 1000 mg = 4782/315 = 15.2
AUC Ratio TAD 500 mg: IV 1000 mg = 2280/315 = 7.2

In conclusion, subcutaneous tissue fluid AUC for TAD 1000 mg Cefazolin and TAD 500 mg Cefazolin yielded 15.2 and 7.2 times AUC, respectively, compared to IVAD 1000 mg Cefazolin (assuming Cefazolin concentration in subcutaneous tissue after IVAD is less than or equal to the concomitant Cefazolin concentration in serum). In serum, TAD yields reduced AUC & Cmax, while prolonging duration of serum Cefazolin compared to IVAD. Based on unique pharmacokinetic absorption characteristics, antibiotic surgical site infection prophylaxis by TAD may be better and have fewer risks compared to the current standard of care, IVAD.

Example 2

Evaluation of Antimicrobial Activity of Lidocaine and Cefazolin by Determination of Minimum Inhibitory Concentration and Minimum Bactericidal Concentration The bactericidal properties of three antimicrobial compounds (Cefazolin, Lidocaine and Lidocaine+Cefazolin) were evaluated by measuring the Minimum Inhibitory Concentration (MIC) and Minimum Bactericidal Concentration for *Staphylococcus aureus* (MRSA) ATCC 33592.

A standardized suspension of *Staphylococcus aureus* (MRSA) ATCC 33592 was prepared by culturing on tryptic soy agar for 3-5 days at 35° C. The agar slant was washed with sterile phosphate buffer solution and the organism concentration was adjusted. Inoculum levels of *Staphylococcus aureus* (MRSA) ATCC 33592 were between $4.4 \times 10^5$ to $4.7 \times 10^5$ CFU/ml.

In order to determine Minimum Inhibitory Concentrations (MIC) of Lidocaine, Cefazolin, and Lidocaine+Cefazolin standardized suspensions of *Staphylococcus aureus* (MRSA) ATCC 33592 were added into separate 10 ml aliquots of varied concentrations of Lidocaine, Cefazolin, and Lidocaine plus Cefazolin. Following inoculation, survival of test microorganisms was determined. This method of determining MIC was based on the method described in the NCCLS document M7: Methods for Dilution Antimicrobial Susceptibility Tests for Bacteria that Grow Aerobically; Approved Standard-Seventh Edition. The results of MIC analysis are summarized in Tables 2-7.

TABLE 2

DAY 1 RESULTS OF MINIMUM INHIBITORY CONCENTRATION (MIC) OF CEFAZOLIN VS. MRSA

| Cefazolin Concentration (mg/L) | 1000 | 500 | 250 | 125 | 62.5 | 31.25 | 15.6 | 7.8 | 3.9 | 1.95 | Positive Control | Sterility |
|---|---|---|---|---|---|---|---|---|---|---|---|---|
| MRSA 4.7 × $10^5$ CFU/ml | O | O | O | O | + | + | + | + | + | + | | |
| MRSA 4.7 × $10^5$ CFU/ml | O | O | O | O | + | + | + | + | + | + | | |
| Cefazolin Only | O | O | O | O | O | O | O | O | O | O | | |
| MRSA Only 4.7 × $10^5$ CFU/ml | + | + | + | + | + | + | + | + | + | + | | |
| Controls | | | | | | | | | | | + | O |

Legend: + = Positive  O = Negative

TABLE 3

DAY 2 RESULTS OF MINIMUM INHIBITORY CONCENTRATION (MIC) OF CEFAZOLIN VS. MRSA

| Cefazolin Concentration (mg/L) | 8000 | 4000 | 2000 | 1000 | 500 | 250 | 125 | 62.5 | 31.25 | 15.6 | Positive Control | Sterility |
|---|---|---|---|---|---|---|---|---|---|---|---|---|
| MRSA 4.4 × $10^5$ CFU/ml | O | O | O | O | O | O | + | + | + | + | | |
| MRSA 4.4 × $10^5$ CFU/ml | O | O | O | O | O | O | + | + | + | + | | |
| Cefazolin Only | O | O | O | O | O | O | O | O | O | O | | |
| MRSA Only 4.4 × $10^5$ CFU/ml | + | + | + | + | + | + | + | + | + | + | | |
| Controls | | | | | | | | | | | + | O |

Legend: + = Positive  O = Negative

TABLE 4

DAY 1 RESULTS OF MINIMUM INHIBITORY CONCENTRATION (MIC) OF LIDOCAINE VS. MRSA

| Lidocaine Concentration (mg/L) | 1000 | 500 | 250 | 125 | 62.5 | 31.25 | 15.6 | 7.8 | 3.9 | 1.95 | Positive Control | Sterility |
|---|---|---|---|---|---|---|---|---|---|---|---|---|
| MRSA 4.7 × $10^5$ CFU/ml | + | + | + | + | + | + | + | + | + | + | | |
| MRSA 4.7 × $10^5$ CFU/ml | + | + | + | + | + | + | + | + | + | + | | |
| Lidocaine Only | O | O | O | O | O | O | O | O | O | O | | |
| MRSA Only 4.7 × $10^5$ CFU/ml | + | + | + | + | + | + | + | + | + | + | | |
| Controls | | | | | | | | | | | + | O |

Legend: + = Positive  O = Negative

TABLE 5

DAY 2 RESULTS OF MINIMUM INHIBITORY CONCENTRATION (MIC) OF LIDOCAINE VS. MRSA

| Lidocaine Concentration (mg/L) | 10000 | 5000 | 2500 | 1250 | 625 | 312.5 | 156 | 78 | 39 | 19.5 | Positive Control | Sterility |
|---|---|---|---|---|---|---|---|---|---|---|---|---|
| MRSA $4.4 \times 10^5$ CFU/ml | O | O | + | + | + | + | + | + | + | + | | |
| MRSA $4.4 \times 10^5$ CFU/ml | O | O | + | + | + | + | + | + | + | + | | |
| Lidocaine Only | O | O | O | O | O | O | O | O | O | O | | |
| MRSA Only $4.4 \times 10^5$ CFU/ml | + | + | + | + | + | + | + | + | + | + | | |
| Controls | | | | | | | | | | | + | O |

Legend: + = Positive  O = Negative

TABLE 6

DAY 1 RESULTS OF MINIMUM INHIBITORY CONCENTRATION (MIC) LIDOCAINE (1000 mg/L) + CEFAZOLIN vs. MRSA

| Cefazolin Concentration (mg/L) | 200 | 100 | 50 | 25 | 12.5 | 6.25 | 3.125 | 1.56 | 0.78 | 0.39 | Positive Control | Sterility |
|---|---|---|---|---|---|---|---|---|---|---|---|---|
| MRSA $4.4 \times 10^5$ CFU/ml | O | O | + | + | + | + | + | + | + | + | | |
| MRSA $4.4 \times 10^5$ CFU/ml | O | O | + | + | + | + | + | + | + | + | | |
| Lidocaine + Cefazolin Only | O | O | O | O | O | O | O | O | O | O | | |
| MRSA Only $4.4 \times 10^5$ CFU/ml | + | + | + | + | + | + | + | + | + | + | | |
| Controls | | | | | | | | | | | + | O |

Legend: + = Positive  O = Negative

TABLE 7

DAY 2 RESULTS OF MINIMUM INHIBITORY CONCENTRATION (MIC) OF LIDOCAINE (1000 mg/L) + CEFAZOLIN VS. MRSA

| Cefazolin Concentration (mg/L) | 200 | 100 | 50 | 25 | 12.5 | 6.25 | 3.125 | 1.56 | 0.78 | 0.39 | Positive Control | Sterility |
|---|---|---|---|---|---|---|---|---|---|---|---|---|
| MRSA $4.6 \times 10^5$ CFU/ml | O | + | + | + | + | + | + | + | + | + | | |
| MRSA $4.6 \times 10^5$ CFU/ml | O | + | + | + | + | + | + | + | + | + | | |
| Lidocaine + Cefazolin Only | O | O | O | O | O | O | O | O | O | O | | |
| MRSA Only $4.6 \times 10^5$ CFU/ml | + | + | + | + | + | + | + | + | + | + | | |
| Controls | | | | | | | | | | | + | O |

Legend: + = Positive  O = Negative

Table 8 shows the results of the analysis of the Minimum Bactericidal Concentration (MBC) of Lidocaine, Cefazolin, and Lidocaine+Cefazolin. Determinations of MBC followed the method described in "Report on the Working Party on Antibiotic Sensitivity Testing of the British Society of Antimicrobial Chemotherapy: A Guide to Sensitivity Testing."

TABLE 8

MINIMUM BACTERICIDAL CONCENTRATION (BAC)

| Test Compound | Day | Concentration (mg/L) | | |
|---|---|---|---|---|
| | | 250 | 125 | 62.5 |
| Cefazolin | 1 (MRSA Inoculum 4.7 × 10$^5$ CFU/ml) | 0 | + | + |
| Cefazolin | 2 (MRSA Inoculum 4.4 × 10$^5$ CFU/ml) | 0 | + | + |

| Test Compound | Day | Concentration (mg/L) | | |
|---|---|---|---|---|
| | | 10,000 | 5,000 | 1,000 |
| Lidocaine | 1 (MRSA Inoculum 4.7 × 10$^5$ CFU/ml) | NA | NA | + |
| Lidocaine | 2 (MRSA | 0 | + | + |

TABLE 8-continued

MINIMUM BACTERICIDAL CONCENTRATION (BAC)

| Test Compound | Day | Concentration (mg/L) | | |
|---|---|---|---|---|
| | | 200 | 100 | 50 |
| Cefazolin + Lidocaine (1000 mg/L) | 1 (MRSA Inoculum 4.4 × 10$^5$ CFU/ml) | 0 | + | + |
| Cefazolin + Lidocaine (1000 mg/L) | 2 (MRSA Inoculum 4.6 × 10$^5$ CFU/ml) | 0 | 0 | + |

Legend: + = Positive 0 = Negative

Endpoints were achieved for all 3 test products, Lidocaine, Cefazolin, and Lidocaine+Cefazolin, evaluated in the MIC and MBC study. The MIC endpoints are shown in Table 9 and the MBC endpoints are shown in Table 10. The results of this evaluation indicate that the MIC for Cefazolin is between 125 and 250 mg/L, Lidocaine was around 5,000 mg/L and the combination of both Cefazolin and Lidocaine had an MIC of 100 mg/L. The slight reduction in the MIC and MBC endpoints for the combined (Lidocaine+Cefazolin) test product indicated that the potency of the Cefazolin was not inhibited by the presence of Lidocaine against MRSA (ATCC #33592). All controls met the criteria established for a valid test.

TABLE 9

MIC END POINTS

| | Cefazolin | | Lidocaine | | Cefazolin + Lidocaine (1000 mg/L) | |
|---|---|---|---|---|---|---|
| Challenge Organism | Day 1 | Day 2 | Day 1 | Day 2 | Day 1 | Day 2 |
| Staphylococcus aureus (MRSA) ATCC 33592 | 125 mg/L | 250 mg/L | NA* | 5000 mg/L | 100 mg/L | 100 mg/L |

*Growth present in all wells/dilutions. No endpoint could be determined on Day 1.

TABLE 10

MBC END POINTS

| | Cefazolin | | Lidocaine | | Cefazolin + Lidocaine (1000 mg/L) | |
|---|---|---|---|---|---|---|
| Challenge Organism | Day 1 | Day 2 | Day 1 | Day 2 | Day 1 | Day 2 |
| Staphylococcus aureus (MRSA) ATCC 33592 | 250 mg/L | 250 mg/L | NA* | 10,000 mg/L | 100 mg/L | 200 mg/L |

*No endpoint could be determined on Day 1.

Example 3

Tumescent Antibiotic Delivery in Treatment of Infection

A patient presenting with a localized infection characterized by a central abscess and inflammation is treated by tumescent antibiotic delivery to the affected area. A solution of 250 mg of cefazolin (150 ml from a solution consisting of 500 mg of cefazolin), 300 mg lidocaine. 0.3 mg epinephrine, 3 meq sodium bicarbonate is dissolved in saline to a total volume of 280 ml. The solution is then infiltrated in the area of inflammation. The patient is examined approximately 12-24 hours after infiltration for visible evidence of inflammation and/or redness.

Example 4

Prophylactic Tumescent Antibiotic Delivery to a Surgical Site of a Patient Under General Anesthesia TLAnti is administered to the subcutaneous compartment of a surgical site in a 70 kg adult patient under general anesthesia. The patient is subsequently monitored for perioperative and postoperative thromboembolism.

Example 5

Prophylactic Tumescent Antibiotic Delivery to a Surgical Site of a Patient without General Anesthesia TLAnti is administered to the subcutaneous compartment of a surgical site or site of other injury in a 70 kg adult patient without general anesthesia. The patient is subsequently monitored for perioperative and postoperative thromboembolism.

Example 6

Tumescent Antibiotic Delivery in Treatment of Infection

TLAnti is administered to the subcutaneous compartment at a site of infection in a 70 kg adult patient without general anesthesia. The concentrations of the antibiotic component and anesthetic component used in TLAnti for the treatment of infection exceed concentrations considered safe for systemic use. The progress of the infection is subsequently monitored in the treated patient.

Example 7

Tumescent Antibiotic Delivery in Surgical Treatment of Breast Cancer

A catheter is inserted into the surgical site and the area infiltrated with a tumescent solution. The tumescent solution comprising 0.9% normal saline, 500 mg of cefazolin, 500 mg lidocaine 2%, 1 mg epinephrine, and 10 mEq bicarbonate. Once sufficient anesthesia is achieved, the surgeon removes cancerous tissue with sufficient margins to ensure complete removal of the tumor. The site can subsequently be closed and dressed.

Example 8

Comparison of Tumescent Antibiotic Delivery (TAD) Vs. IV Antibiotic Delivery (IVAD) in Reducing the Risk of Surgical Site Infections (SSI)

Two modes of antibiotic delivery, Tumescent Antibiotic Delivery (TAD) and IV Antibiotic Delivery (IVAD), are compared in their ability to reduce the risk of infection following inoculation with *Staphylococcus* aureus.

Solutions of cefazolin are prepared for TAD and IVAD. When a single route of delivery of cefazolin is used (either IVAD or TAD), the total dosage of antibiotic is equal to 250 mg/kg. When both routes of delivery are used (both IVAD & TAD), the total dosage of antibiotic is equal to 250 mg/kg; however, the relative IVAD and TAD dosages may vary. In this protocol, the relative dosages of antibiotic delivered via IVAD and TAD are 125 mg/kg each.

Eighty rats are anesthetized and their backs shaved and cleansed. Groups of 20 rats each are given a 250 mg/kg dose of cefazolin either by subcutaneous tumescent administration (TAD), intraperitoneal injection (IVAD), or a combination of TAD and IVAD 15 to 35 minutes prior to making a 4 cm sterile vertical incision through the skin of the back into the subcutaneous tissue. The incisions are then immediately inoculated with *Staphylococcus aureus* at concentrations of $10^2$, $10^3$, $10^4$ or $10^5$ organisms per ml and closed. As controls, one group of 10 rats is untreated prior to undergoing incision and inoculation as described above and one group of 10 rats is given a 250 mg/kg dose of cefazolin by a combination of TAD and IVAD prior to incision, but the incision is closed without inoculation. Four days after surgery, the rats are euthanized and samples of 1 $cm^2$ of tissue from the lateral side of the incisions is collected for microbiological assessment.

The collected tissue is weighed and placed in individual sterile tubes containing 1 ml of sterile tryptic soybean broth (TBS). The tissue is homogenized and four 1:10 serial dilutions of each homogenate with 0.5-ml aliquots and diluted with 4.5 ml of sterile TSB: $10^{-1}$ to $10^{-4}$ are made. Blood agar plates are inoculated with 0.1 ml of each dilution and the plates are incubated at 35° C. for 18 to 24 hours. On each plate containing 30-300 CFU the colonies are counted and the number of CFU per gram of tissue is calculated using the formula described in Barron E J, Peterson L R, Finegold S M, Catalase-positive gram positive-cocci, *Staphylococcus, Micrococcus*, and similar organisms. Baily and Scott's Diagnostic Microbiology, $9^{th}$ ed., St Louis Mo.: Mosby 1994. p. 284-95. One-way ANOVA statistical analysis is performed to determine the effectiveness of TAD vs. IVAD in reducing the risk of infections.

Example 9

Ability of Lidocaine in Tumescent Local Anesthesia to Impair Platelet Activation The Duke method of determining bleeding time is used to assess effect of tumescent administration of TLAnti comprising 0.5 mg/ml lidocaine on hemostatic function (platelet response to injury and functional capacity of vasoconstriction).

The skin of the left and right thigh of a subject is cleaned and allowed to dry. A 1 liter solution of TLAnti comprising 0.9% normal saline, 500 mg of cefazolin, 500 mg lidocaine 2%, 1 mg epinephrine, 10 mEq bicarbonate is infiltrated into the subcutaneous tissue of the left thigh until the skin becomes swollen and taught—tumescent. Simultaneous 4 mm deep puncture wounds are made to the same area of the left and right thighs with disposable lancets. The puncture sites are blotted with filter paper every 30 seconds, until bleeding stops and the bleeding time for each thigh is recorded. The bleeding times of the left and right thigh are compared to determine if administration of TLAnti increases bleeding time. Normal bleeding time measured by the Duke method is 1 to 3 minutes.

In a preliminary experiment, bleeding time and bleeding area were measured in a patient before and after tumescent lidocaine exposure. The results are shown in Table 11. There was essentially no change in Average Bleeding Time (BT). In contrast, there was a 40% increase in Average Bleeding Area (BA). Bleeding Area (BA) was a more sensitive and a more specific test for platelet function compared to Bleeding Time (BT). Thus, this pilot study provides the hypothesis that tumescent lidocaine may impair platelet function and may decrease the risk of post-op thromboembolism. In other words, TAD may reduce the risk of both post-operative surgical site infection and post-operative thromboembolism.

TABLE 11

COMPARING PRE-OP CONTROLS TO POST-OP TUMESCENT LIDOCAINE EXPOSURE

| Pt # | Name last first initial | Test # | Bleeding Time BT × 2 | Bleeding Area BA |
|---|---|---|---|---|
| 1 | Patient 1 M | T1 Control | 12 | 579.42 |
| 1 | Patient 1 M | T2 Control | 12 | 502.52 |
| | | | Control BT = 6 | Control BA = 541 |
| 1 | Patient 1 M | T3 Lidocaine | 10 | 791.81 |
| 1 | Patient 1 M | T4 Lidocaine | 13 | 726.03 |
| | | | Lidocaine BT = 5.75 | Lidocaine BA = 759 |

Example 10

Subcutaneous Tumescent Antimicrobial Delivery: Pharmacokinetics for Prevention of Surgical Site Infection The time from surgical incision until wound closure is when bacterial contamination is most likely to occur. Surgical site infections (SSIs) increase morbidity, length of hospitalization, and hospital costs. SSIs can be devastating for patients and a tremendous financial burden on a health care system. The incidence of SSI among certain common clean and clean-contaminated surgical procedures ranges from 1% to 11%, respectively. The Center for Disease Control (CDC) has defined 3 classes of surgical site infection (SSI): 1) Superficial Incisional SSI, an infection involving skin or subcutaneous tissue within 30 days of surgery; 2) Deep Incisional SSI, an infection involving fascia and muscle layers within 30 days after surgery without an implant or 1 year if an implant is left in place and the infection appears to be related to the surgery and the incision; and 3) Organ/Space SSI, an infection involving any organ or spaces opened and manipulated during the surgery occurring within 30 days of surgery without an implant or 1 year if an implant is left in place and the infection appears to be related to the surgery and the infection.

Prevention of SSI by antibiotics depends upon the concentration profile of the antibiotic (magnitude and duration) within the interstitial space fluid (ISF) at the site of potential bacterial contamination. In turn, antibiotic concentration in ISF depends upon the mode of antibiotic delivery and the total dose of antibiotic. The area under the curve of concentration as a function of time (AUC), the maximum concentration (Cmax) and the duration of time that the antibiotic concentration exceeds the MIC for specific bacteria (T>MIC) are important pharmacokinetic (PK) metrics for bioavailability of antibiotics within subcutaneous adipose tissue. The mode of antibiotic delivery with the greatest AUC, Cmax and T>MIC in subcutaneous tissue is expected to be the most effective at preventing surgical incision site infections.

Modes of Antibiotic Delivery

Most pharmacokinetic studies of antibiotics for SSI prevention consider only one mode of antibiotic delivery, intravenous antibiotic delivery (IVAD). A common metric used to quantitatively compare cumulative antibiotic exposure in different clinical situations after IVAD is the penetration ratio (P) of an antibiotic from serum into subcutaneous ISF, where P=freeAUC[ISF]IVAD/freeAUC[SERUM]IVAD. Penetration ratios can be used to compare different drugs or different formulations of the same drug after IVAD. Antibiotic penetration ratio varies widely between different patients and between different tissues and is decreased by surgery, diabetes and obesity. For example, the penetration of an antibiotic is quantitatively different after IVAD among obese patients compared to normal patients.

Peri-incisional or intra-incisional injection of antibiotics has been found to reduce the risk of SSI compared to IVAD. Such techniques for local delivery of antibiotics involve the infiltration of small volumes of antibiotic solution, resulting in a minimal reservoir effect and minimal dispersion into adjacent tissue. Antibiotic solutions introduced by peri-incisional or intra-incisional injection, which do not contain a vasoconstrictor drug like epinephrine, are rapidly absorbed with rapid decline of antibiotic concentrations within the targeted tissue. The small volumes of antibiotic solutions introduced by peri-incisional or intra-incisional injection do not produce hyper-hydration of the targeted tissues or prevent wound surface desiccation, which impairs migration of neutrophils and macrophages onto the wound surface. Despite some evidence that peri-incisional or intra-incisional injection of antibiotics can reduce SSI risk, such techniques are not used for SSI prophylaxis and consensus opinion suggests that subcutaneous administration of antibiotics for SSI prophylaxis shows "unreliable results and therefore should be avoided as far as possible." See Stratchounski L S, Taylor E W, Dellinger E P, Pechere J C. Antibiotic policies in surgery: a consensus paper. Int J Antimicrob Agents 26:312-322, 2005.

Unlike peri-incisional or intra-incisional antibiotic injection, tumescent antibiotic delivery (TAD) involves the infiltration of a relatively large volume of an antibiotic-containing solution into the subcutaneous compartment, such that the surrounding tissue becomes swollen and firm, i.e., tumescent. A TAD solution comprises one or more antibiotics dissolved in tumescent local anesthesia (TLA), which comprises relatively large volumes of dilute lidocaine ($\leq 1$ grams/L), epinephrine ($\leq 1$ milligrams/L), sodium bicarbonate (10 milliequivalents/L) in physiologic saline or lactated Ringer's solution. The physical and physiologic effects of infiltrating a TAD solution are identical to the effects of a solution of TLA and include prolonged and profound local anesthesia, extensive local epinephrine-induced capillary and venous constriction for surgical hemostasis, hydrostatic pressure-induced capillary and venous compression, inhibition of incisional-trauma-induced platelet activation and delayed systemic absorption of solution components, for example, lidocaine and antibiotics.

The spread of tumescent fluid within subcutaneous tissue occurs by means of rapid bulk flow through the interstitial gel substance. Efficient infiltration of up to five liters of solution or more into subcutaneous fat may be facilitated by use of specialized infiltration cannulas, peristaltic infiltration pumps and tubing. Equilibration of ISF pressures results in a uniform distribution of tumescent fluid throughout the infiltrated tissues. A process of detumescence occurs during 1 to 2 hours following infiltration. The rate of systemic absorption of antibiotics from tumescent subcutaneous tissue is slow as a result of wide spread tumescent vasoconstriction. TAD produces a prolonged large-volume subcutaneous reservoir of an antibiotic solution within a mass of vasoconsticted local tissues. The pharmacokinetic behavior of this reservoir is analogous to a slow-release oral tablet or a slow constant IV Infusion.

Tumescent techniques were developed for local delivery of to enable liposuction to be done totally by local anesthesia. Tumescent local anesthesia (TLA) produces profound surgical local anesthesia persisting for more than 6 to 8 hours with peak serum lidocaine concentrations occurring between 10 to 16 hours after completion of the subcutaneous infiltration. In contrast, 1% or 2% commercial concentrations of lidocaine with epinephrine reliably provide local anesthesia for 2 to 3 hours or less. Because of its prolonged local anesthesia and profound local vasoconstriction, tumescent local anesthesia (TLA) has become the standard of care for a number of surgical procedures limited to skin, subcutaneous tissue, or vascular structures including liposuction totally by local anesthesia, endovenous laser ablation of large leg-vein venous varicosities, skin grafting in burn patients. TLA has been successfully be used for mastectomy and subclavian steal syndrome repair totally by local anesthesia in patients who were not good candidates for general anesthesia. When TLA is used for liposuction the maximum safe mg/kg dosage of tumescent lidocaine is 45 mg/kg to 55 mg/kg. In adults, the maximum safe mg/kg dosage of tumescent lidocaine for TLA without liposuction is estimated to be 30 mg/kg, while the current dosage limitation approved by the FDA for infiltration local anesthesia using commercial lidocaine (1%=10 gm/L) with epinephrine (1:100,000=10 mg/L) is 7 mg/kg.

Intravenous antibiotic delivery (IVAD) may not reliably achieve adequate subcutaneous antibiotic concentrations for prevention of surgical site infections (SSIs). Tumescent antimicrobial delivery (TAD) consists of subcutaneous infiltration of an antimicrobial (antibiotic, antiviral, antifungal) dissolved in a large volume of dilute tumescent lidocaine anesthesia (TLA), containing lidocaine ≤1 gm/L, epinephrine ≤1 mg/L, sodium bicarbonate 10 mEq in 0.9% physiologic saline. The primary aim of this research was to measure cefazolin and metronidazole concentrations as a function of time in subcutaneous interstitial fluid after TAD, in serum after TAD and in serum after IVAD. We hypothesize that TAD provides uniformly higher subcutaneous antibiotic concentrations compared to IVAD and that the area under the curve (AUC∞) of the concentration-time profile and the peak concentrations (Cmax) of concomitant TAD+IVAD are superior to IVAD alone for SSI prevention.

Five pharmacokinetic studies each involved one IVAD procedure and one or two TAD procedures or a concomitant TAD+IVAD procedure. After TAD of cefazolin alone and after TAD of cefazolin plus metronidazole, antibiotic concentrations in tumescent interstitial fluid (TISF) and serum were measured sequentially over 8 to 16 hours. After IVAD, serum antibiotic concentrations of cefazolin and metronidazole were measured sequentially over 14 to 16 hours. The AUC∞ and Cmax with TAD and with IVAD were compared.

TAD of 1 gm of cefazolin resulted in AUC∞ and Cmax in subcutaneous interstitial fluid 16.5 and 5.6 times greater, respectively, than in serum after 1 gm by IVAD. TAD of 500 mg of metronidazole resulted in AUC∞ and Cmax in TISF that was 8.1 and 24.7 times greater, respectively, than in serum after 500 mg by IVAD. After TAD, subcutaneous Cmax is approximately equal to the antibiotic concentration in the TAD solution. Slow systemic absorption after subcutaneous infiltration by TAD resulted in serum antibiotic concentration-time profiles that resemble a slow IV infusion. There were no adverse events or evidence of tissue toxicity associated with TAD.

Compared to IVAD alone, TAD+IVAD provides superior antibiotic bioavailability in both local subcutaneous tumescent interstitial fluid and serum, suggesting TAD+IVAD might improve SSI prevention. For surgery involving only skin and subcutaneous tissue, tumescent antibiotic delivery alone may be superior to IV drug delivery alone.

A phase I pharmacokinetic clinical trial was conducted comparing the subcutaneous and systemic bioavailability of antibiotics following subcutaneous tumescent antimicrobial delivery (TAD) or IV antibiotic delivery (IVAD). After tumescent infiltration, subcutaneous interstitial fluid (ISF) is designated tumescent interstitial fluid (TISF).

TAD is the direct subcutaneous infiltration of antimicrobial drug(s) dissolved in a large volume of a TLA solution. A TLA solution consists of lidocaine (≤1 gm), epinephrine (≤1 mg), and sodium bicarbonate (10 mEq) per liter bag of physiologic saline or lactated Ringer's solution. Sodium bicarbonate neutralizes the acidic pH of commercial local anesthetics thereby reducing the stinging-pain associated with subcutaneous infiltration of commercial solutions of lidocaine with epinephrine (McKay W, Morris R, Mushlin P. Sodium Bicarbonate Attenuates Pain on Skin Infiltration with Lidocaine, with or without Epinephrine. Anesth Analg 1987, 66:572-57). In other words, a TLA solution consists of at least a 10-fold dilution of commercial 1% lidocaine with epinephrine 1:100,000.

In this research we studied TAD of cefazolin and metronidazole. Cefazolin and metronidazole were selected because they are water soluble and generally safe, effective and economical for prevention of SSIs (Meyer N L, Hosier K V, Scott K, Lipscomb GH. Cefazolin versus cefazolin plus metronidazole for antibiotic prophylaxis at cesarean section. South Med J. 2003; 96:992-5; Morris W T, Innes D B, Richardson R A, Lee A J, Ellis-Pegler R B. The prevention of post-appendicectomy sepsis by metronidazole and cefazolin: a controlled double blind trial. Aust N Z J Surg. 1980; 50:429-33; Brown G R, Clarke A M. Therapeutic interchange of cefazolin with metronidazole for cefoxitin. Am J Hosp Pharm. 1992; 49:1946-50; Hospenthal D R, Murray C K, Andersen R C, et al. Guidelines for the prevention of infections associated with combat-related injuries: 2011 update: endorsed by the Infectious Diseases Society of America and the Surgical Infection Society. J Trauma. 2011; 71 (2 Suppl 2):5210-34; Cho M J, Kurtz R R, Lewis C, Machkovech S M, Houser D J. Metronidazole phosphate—a water-soluble prodrug for parenteral solutions of metronidazole. J Pharm Sci. 1982; 71:410-4). Cefazolin and metronidazole, when mixed together in a saline solution for IV delivery, are both chemically stable for at least 72 hours at 8° C. (Rivers T E, McBride H A, Trang J M. Stability of cefazolin sodium and metronidazole at 8 degrees C. for use as an i.v. admixture. J Parenter Sci Technol. 1993; 47:135-7).

Despite I V antibiotic prophylaxis, surgical site infections (SSIs) remain a significant problem (Watanabe M, Suzuki, H, Nomura S, Maejima K, Chihara N, Komine O, Mizutani S, Yoshino M, Uchida E. Risk factors for surgical site infection in emergency colorectal surgery: a retrospective analysis. Surg Infect (Larchmt) 2014; 15:256-61; Smith R L, Bohl J K, McElearney S T, Friel C M, Barclay M M, Sawyer R G, Foley E F. Wound infection after elective colorectal resection. Ann Surg. 2004; 239:599-605; Bot J, Piessen G, Robb W B, Roger V, Mariette C. Advanced tumor stage is an independent risk factor of postoperative infectious complications after colorectal surgery: arguments from a case-matched series. *Dis Colon Rectum.* 2013; 56:568-76). SSIs devastate patients and are a tremendous financial burden on health care systems (de Lissovoy G, Fraeman K, Hutchins V, Murphy D, Song D, Vaughn B B. Surgical site infection: incidence and impact on hospital utilization and treatment costs. Am J Infect Control, 2009; 37:387-97; Vogel T R, Dombrovskiy V Y, Lowry S F. Trends in postoperative sepsis: are we improving outcomes? Surg Infect 2009; 10:71-8; Fukuda N, Wada J, Niki M, Sugiyama Y, Mushiake H. Factors predicting mortality in emergency abdominal surgery in the elderly. World J Emerg Surg 2012; 7:12; Broex E C, van Asselt A D, Bruggemann C A, van Tiel F H. Surgical site infections: how high are the costs? J Hosp Infect 2009; 72:193-201). In recent years, major efforts to reduce SSIs have only achieved incremental improvements (Alexander J W, Solomkin J S, Edwards M J. Updated recommendations for control of surgical site infections. Ann Surg. 2011; 253:1082-93; Larochelle M, Hyman N, Gruppi L, Osler T. Diminishing surgical site infections after colorectal surgery with surgical care improvement project: is it time to move on? Dis Colon Rectum. 2011; 54:394-400; Serra-Aracil X, Garcia-Domingo M I, Pares D, Espin-Basany E, Biondo S, Guirao X, Orrego C, Sitges-Serra A. Surgical site infection in elective operations for colorectal cancer after the application of preventive measures. Arch Surg. 2011; 146:606-12; Owens P L, Barrett M L, Raetzman S, Maggard-Gibbons M, Steiner C A. Surgical site infections following ambulatory surgical procedures. JAMA 2014; 311:709-716). Anesthesiologists are most frequently responsible for administering perioperative antimicrobial prophylaxis (Sinha B, van Assen S, Friedrich A W. Important issues for perioperative systemic antimicrobial prophylaxis in surgery. Curr Opin Anaesthesiol. 2014; 27:377-81; Roth J V. More reasons why anesthesiologists should administer preoperative antibiotics. Anesthesiology 2004; 101:258-259).

The cause of subcutaneous surgical site infections (SSI) is bacterial contamination of subcutaneous interstitial fluid on the surface of incised tissue. Increased antibiotic bioavailability in subcutaneous interstitial fluid reduces the risk of SSI. After IVAD antibiotic penetration from serum into subcutaneous interstitial fluid at a surgical incision site varies widely between different patients and between different tissues and is decreased by diabetes and obesity. Surgical incision reduces local subcutaneous antibiotic bioavailability following IVAD as the result of capillary hypotension, vasoconstriction, capillary thrombosis, tissue edema and tissue desiccation (Kennedy M J, Van Riji A. Effects of surgery on the pharmacokinetic parameters of drugs. Clin Pharmacokinet 1998; 35:293-312; Cardinale F, Chinellato I, Caimmi S, Peroni D G, Franceschini F, Miraglia Del Giudice M, Bernardini R. Perioperative period: immunological modifications. Int J Immunopathol Pharmacol. 2011; 24 (3 Suppl):53-12; Markantonis S L, Kostopanagiotou G, Panidis D, Smirniotis V, Voros D. Effects of blood loss and fluid volume replacement on serum and tissue gentamicin concentrations during colorectal surgery. Clin Ther. 2004; 26:271-81; Skhirtladze K, Hutschala D, Fleck T, Thalhammer F, Ehrlich M, Vukovich T, Müller M, Tschernko E M. Impaired target site penetration of vancomycin in diabetic patients following cardiac surgery. Antimicrob Agents Chemother. 2006; 50:1372-5; Lagneau F, Marty J, Beyne P, Tod M. Physiological modeling for indirect evaluation of drug tissular pharmacokinetics under non-steady-state conditions: an example of antimicrobial prophylaxis during liver surgery. J Pharmacokinet Pharmacodyn. 2005; 32:1-32; Nimmo W S, Peacock J E. Effects of anesthesia and surgery on pharmacokinetics and pharmacodynamics. Br Med Bull. 1988; 44:286-301; Berríos-Torres S I, Yi S H, Bratzler D W, Ma A, Mu Y, Zhu L, Jernigan J A. Activity of Commonly Used Antimicrobial Prophylaxis Regimens against Pathogens Causing Coronary Artery Bypass Graft and Arthroplasty Surgical Site Infections in the United States. 2006-2009. Infect Control Hosp Epidemiol. 2014; 35:231-9; Andreas M1, Zeitlinger M, Hoeferl M, Jaeger W, Zimpfer D, Hiesmayr J M, Laufer G, Hutschala D. Internal mammary artery harvesting influences antibiotic penetration into presternal tissue. Ann Thorac Surg. 2013; 95:1323-9; Barbour A, Schmidt S, Sabarinath S N, Grant M, Seubert C, Skee D, Murthy B, Derendorf H. Soft-tissue penetration of ceftobiprole in healthy volunteers determined by in vivo microdialysis. Antimicrob Agents Chemother. 2009; 53:2773-6; Burkhardt O, Brunner M, Schmidt S, Grant M, Tang Y, Derendorf H. Penetration of ertapenem into skeletal muscle and subcutaneous adipose tissue in healthy volunteers measured by in vivo microdialysis. J Antimicrob Chemother 2006; 58:632-636; Müller M, dela Peña, A, Derendorf H. Issues in pharmacokinetics and pharmacodynamics if anti-infective agents: distribution in tissue. Antimicrob Agents Chemother 2004; 48:1441-1453; Brunner M, Pernerstorfer T, Mayer B X, Eichler H, Müller M. Surgery and intensive care procedures affect the target site distribution of piperacillin. Crit Care Med 2000; 28:1754-1759; Kim A, Suecof L A, Southerland C A, Gao L, Kuti J L, Nicolau D P. In vivo microdialysis study of the penetration of daptomycin into soft tissues in diabetic versus healthy volunteers. Antimicrob Agents Chemother 2008; 52: 3941-3946; Toma O, Suntrup P, Stefanescu A, London A, Mutch M, Kharasch E. Pharmacokinetics and tissue penetration of cefoxitin in obesity: implications for risk of surgical site infection. Anesth Analg. 2011; 113:730-7). General anesthesia can further reduce antibiotic bioavailability by decreasing cardiac output.

The remarkable safety of TLA is documented by years of worldwide experience with tumescent liposuction as well as pharmacokinetics analysis (Klein J A, Jeske D R. Maximum safe dosage of tumescent lidocaine. Anesth Analg in 2015; in press). As the result of delayed systemic absorption, the estimated risk of mild lidocaine toxicity from tumescent lidocaine at a dosage of 28 mg/kg is less than 1/100,000. At a lidocaine dosage of 28 mg/kg, a 70 kg adult can receive 2 liters of TAD solution with an insignificant risk of toxicity. The current FDA approved package-insert labeling of lidocaine with epinephrine for infiltration local anesthesia states that the maximum recommended lidocaine dosage is 7 mg/kg.

TAD is a novel form of drug delivery. TAD has unexpected local and systemic effects. Wide spread subcutaneous vasoconstriction resulting from a large volume of dilute tumescent epinephrine produces in slow steady systemic absorption of drugs dissolved in the TLA solution, persistent high local tissue concentrations of the drugs, prolonged local anesthesia and reduced surgical blood loss (Klein J A. Tumescent technique for local anesthesia improves safety in large volume liposuction. Plast Reconstr Surg 1993; 92:1085-1098).

The mean inhibitory concentration (MIC) is an ex-vivo predictor of the susceptibility of a specific strain of bacteria to a specific antibiotic. In-vivo predictors of susceptibility of a specific bacterium to a specified antibiotic within a specified tissue depend on both the MIC as well as antibiotic access to the site of infection. Antibiotic access to the site of infection is measured by the area under the curve (AUC∞) of a drug's concentration-time profile, the drug's peak concentration (Cmax) and the length of time that the MIC is exceeded by antibiotic concentration (T>MIC). AUC∞, Cmax and T>MIC depend upon the antibiotic's pharmacokinetic properties, formulation and mode of delivery. In this research AUC∞ is used as the metric for bioavailability.

The principal aim of this research was to measure concentrations of cefazolin and metronidazole over time in subcutaneous tissue and serum following TAD and in serum following IVAD. We hypothesize that TAD can provide uniformly higher and more prolonged subcutaneous antibiotic concentrations compared to IVAD.

There were six secondary research aims. The first of these research aims was to determine the bioavailability (AUC∞), the peak serum concentrations (Cmax) and the time of Cmax (Tmax) of cefazolin and metronidazole in tumescent interstitial fluid (TISF) and serum following TAD and in serum following IVAD. We hypothesized that, at equal mg doses, both AUC∞ and Cmax in serum after IVAD alone are smaller than in TISF after TAD alone. In addition, we hypothesized that, at equal doses, subcutaneous AUC∞ and Cmax are always smaller after IVAD alone than after TAD alone or after TAD+IVAD.

A second research aim was to determine the correlation between the antibiotic concentration (μg/ml) in a TAD solution and the resulting antibiotic concentration (mg/L) in TISF immediately after TAD. We hypothesized that the respective concentrations are highly correlated and nearly equal.

A third research aim was 1) to observe the concentration vs time profiles of cefazolin and metronidazole in serum after rapid IVAD and in TISF after TAD, at equal mg doses and equal mg/L concentrations in the TAD solution. We hypothesize that concentration-time profiles of these two drugs are different in serum after IVAD and identical in TISF after TAD.

A fourth research aim was to document evidence of adverse effects of subcutaneous delivery of large volumes of dilute cefazolin, metronidazole, lidocaine and epinephrine. We hypothesize that there would be no evidence of either systemic or local tissue toxicity associated with subcutaneous delivery of these drugs and therefore TAD represents a non-significant risk of harm to patients.

A fifth research aim was to observe the serum concentration-time profile of the antibiotics after TAD and subsequent systemic absorption. We hypothesize that, following TAD, the slow systemic absorption of the antibiotics from the subcutaneous TISF would produce a serum concentration-time profile of the antibiotics similar to that of a continuous slow IV infusion.

A sixth aim was to apply the present research results to generate new hypotheses that can be tested in future randomized clinical trials comparing tumescent antimicrobial delivery versus IV antimicrobial delivery for surgical site infection prophylaxis or for other clinical applications.

The protocol received institutional review board approval and written informed consent was obtained prior to each research procedure. We compared tumescent antibiotic delivery (TAD) and intravenous antibiotic delivery (IVAD) with respect to concentration-time profile, AUC∞, Cmax and T>MIC.

Only after a prospective patient had requested liposuction surgery was the person offered the opportunity to participate in this research. Volunteer subjects were offered liposuction at no cost.

Eligibility requirements were: good health (ASA I) and good candidate for liposuction, age at least 18, not pregnant, no history of allergy to lidocaine, cefazolin or metronidazole, and good venous access. Exclusion criteria were: current significant health problems, history or evidence of HIV or Hepatitis C infection and no current use of drugs that block cytochrome P450 3A4 or 1A2 or impair hemostasis.

The first 3 pharmacokinetic studies involved only cefazolin. The last two studies involved simultaneous delivery of cefazolin and metronidazole. Each of the 5 studies consisted of one IV antibiotic delivery (IVAD) procedure and one or two TAD infiltration procedures. In individual subjects, procedures were performed at least one week apart.

Standard tumescent lidocaine anesthesia (TLA) solution was prepared by transferring 100 ml of commercial lidocaine (1%) with epinephrine (1:100,000), for a total of 1 gm of lidocaine and 1 mg of epinephrine in 100 ml, together with 10 ml of 8.4% sodium bicarbonate, into a 1,000 ml bag of physiologic saline. The resulting TLA solution contained 1000 mg of lidocaine in 1,110 ml of solution, which is equivalent to 900 mg/L or 0.09% lidocaine. For some procedures the lidocaine concentration was reduced in order not to exceed a total lidocaine dosage of 45 mg/kg.

The standard TAD solution of cefazolin was prepared by withdrawing 10 ml of TLA solution and injecting this 10 ml into a vial containing 1000 mg of cefazolin powder. The solubilized cefazolin was then re-injected into the TLA solution. Metronidazole for IV delivery is available as 500 mg in 100 ml. TAD with metronidazole was prepared by adding 500 mg in 100 ml to 1110 ml of a TLA solution. A bag of TAD solution with 1000 mg of cefazolin and 500 mg of metronidazole contained 1210 ml. In other words the TAD solution contained 826 mg/L of cefazolin (1000 mg/1210 ml), 423 mg/L of metronidazole (500 mg/1210 ml) and 826 mg/L=0.083% lidocaine (1000 mg/1210 ml) with epinephrine (1 mg/1210 ml=1:1,200,000).

Large volume tumescent infiltration (≥0.5 liter) was accomplished using a tumescent infiltration cannulas, peristaltic infiltration pump and infiltration tubing (HK Surgical, Inc., San Clemente, Calif. 92673). The discomfort of tumescent infiltration was minimized by a sequential infiltration technique: first using a spinal needle to infiltrate a relatively small volume of TAD sufficient to provide minimal anesthesia to allow comfortable insertion of blunt-tipped 16 gauge tumescent infiltration cannulas that provide large volume infiltration. The spinal needle and blunt-tipped infiltration cannulas were inserted through the skin via 1 mm adits made by a 1 mm skin biopsy punch. All patients were fully awake and received no parenteral sedation.

Sample Collection: After IVAD, only serum concentrations were measured. After TAD both serum and TISF concentrations were measured. IVAD was achieved via an antecubital vein. Serum samples were obtained via an indwelling IV catheter in the contralateral antecubital vein.

Sequential serum samples for antibiotic concentrations were obtained every 1 to 2 hours for up to 12 to 18 hours beginning at T0 immediately after completion of the antibiotic delivery. A two-syringe sampling technique first removed 2 mL of blood, which was discarded, and then 10 mL of blood was obtained in a second syringe for drug assay. After each blood sample the IV catheter was flushed with 2 ml of saline and then 0.5 mL of heparin (10 units/mL).

Sequential samples of tumescent adipose tissue (10 ml to 20 ml) were obtained by the hand-held syringe liposuction technique. Sampling began at time TO immediately after completing TAD infiltration and continued every 1 to 2 hours until the subject experienced significant discomfort as the result of diminishing local anesthesia. Samples of the subcutaneous tissue aspirate were centrifuged. The supranatant fat was discarded. The aqueous infranate tumescent interstitial fluid (TISF) was assayed for cefazolin and metronidazole content by high-pressure liquid chromatography (cefazolin by Toxicology and Drug Monitoring Laboratory, Mayo Clinic, Rochester, Minn. 55905 and metronidazole by NMS Labs, 3701 Welsh Road, Willow Grove, Pa. 19090.

Data Analysis: We recorded the effect of varying the mg dose and mg/L concentration of antibiotics within TAD solutions between procedures in individual subjects and between different subjects.

After TAD the Cmax in the TISF occurred at time TO. Linear regression analysis was used to determine the correlation (coefficient of determination R2) between the antibiotic concentration (mg/L) in a TAD solution and Cmax in the infranatant liposuctioned subcutaneous tissue TISF. After TAD and after IVAD, Cmax in serum was determined by inspection of the sequential assays. AUC∞ was determined by the trapezoid rule.

At the time when each sample of TISF was obtained, patients were examined and questioned about signs and symptoms of subcutaneous tissue toxicity including unusual soreness, tenderness, discoloration, swelling at sites of subcutaneous tumescent infiltration. At the same time, subjects were observed and questioned about objective signs or subjective symptoms of lidocaine or epinephrine toxicity. One week after TAD patients were questioned by telephone about any signs and symptoms of subcutaneous tissue toxicity at the sites of TAD.

Results

The research cohort consisted of non-obese healthy adult females, age range 37-64 years. There were 5 separate studies. Each study consisted of 2 to 3 pharmacokinetic procedures involving an individual subject. There were a total of 14 pharmacokinetic procedures.

The range of cefazolin concentrations in the TAD solutions ranged from 225 mg/L to 900 mg/L. The range of metronidazole concentrations in the TAD solutions ranged from 345 mg/L or 413 mg/L.

The antibiotic concentration in serum after IVAD was less than the antibiotic concentration in TISF after TAD at every time point. For each study the antibiotic concentration over time is shown in FIGS. 9-13 with corresponding data presented in Tables 12-16 below. Patient-level data regarding mg drug doses and TAD mg/L drug concentrations is provided in Tables 17 and 18.

After TAD the Cmax in TISF for both cefazolin and metronidazole occurred immediately after completion of the TAD infiltration, followed by a slow linear decline. After TAD the Cmax in serum for cefazolin occurred at time Tmax, with a mean Tmax=8.5 (range 8-12) and for metronidazole the mean Tmax=11 (range 10-12). After TAD, both the cefazolin and metronidazole antibiotic concentration-time profiles in serum resemble that of a constant slow IV infusion. After a bolus IVAD, the Cmax in serum is achieved almost immediately, followed by an exponential decline of antibiotic concentration.

Serum concentrations of cefazolin during the first 6 hours after delivery were always greater following IVAD than after TAD. Beyond the initial 6 hours, serum cefazolin concentrations after TAD were uniformly greater than serum concentration after IVAD.

Serum concentrations of metronidazole during the first 10 hours after delivery were always greater following IVAD than after TAD. Beyond the initial 10 hours, serum metronidazole concentrations after TAD were uniformly greater than serum concentrations after IVAD.

At equal antibiotic doses, the Cmax in TISF after TAD was always greater than the Cmax in serum after IVAD, which in turn was always greater than the Cmax in serum after TAD.

At equal antibiotic doses, the magnitude of AUC∞, Cmax and T>MIC (for an arbitrary MIC) in serum following IVAD were less than the AUC∞, Cmax and T>MIC in subcutaneous TISF after TAD. Even when the TAD dose was less than half the IVAD dose, the antibiotic concentration in serum after IVAD was uniformly less than the antibiotic concentration in TISF after TAD. The mean Cmax in TISF after TAD was 90% of the antibiotic concentration in the TAD solution (range 76.9% to 104%). For TAD, increasing the antibiotic dose or increasing the antibiotic concentration in the TAD solution increases the AUC, Cmax and T>MIC in serum.

Figure 14:
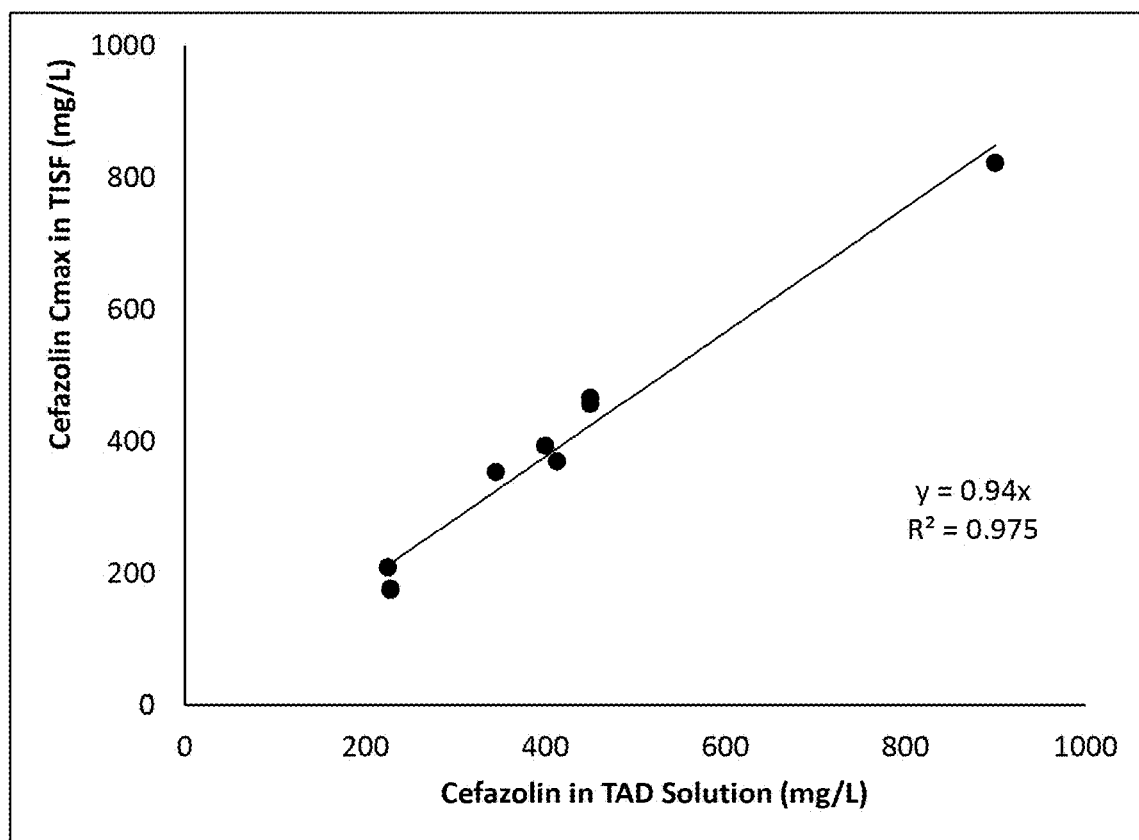
FIG. 14. There is a strong linear correlation ($R^2$=0.975) between the mg/L concentration of cefazolin in the TAD solution and the resulting peak (initial) mg/L concentration (Cmax) of cefazolin within the aspirated tumescent interstitial fluid (TISF) after TAD. The concentration of antibiotic in the TAD solution is approximately equal to the antibiotic concentration within the subcutaneous tissue following tumescent infiltration.

There was a strong positive linear correlation between the cefazolin concentrations in the TAD solution and Cmax in the subcutaneous TISF (coefficient of determination R2=0.975). See FIG. 14.

At equal mg doses different in serum after IVAD the concentration-time profiles of cefazolin and metronidazole were significantly different. In contrast, at equal mg doses and equal mg/L concentrations in the TAD solution, the concentration-time profiles of cefazolin and metronidazole were identical in TISF after TAD. See FIG. 12C.

There was no evidence of tissue toxicity associated with subcutaneous delivery of these antibiotics in a TAD solution and no evidence of adverse events associated with large volumes of dilute tumescent lidocaine and epinephrine.

Discussion

TAD provides prolonged local subcutaneous antibiotic concentrations, prolonged systemic therapeutic concentrations of antibiotics and lidocaine, prolonged local anesthesia for intraoperative and postoperative analgesia, prolonged local vasoconstriction for surgical hemostasis and local tissue hydration to prevent incision site desiccation. The most important findings of this research were as follows.

For surgical procedures involving deep organs or tissues, TAD+IVAD provides a pharmacokinetically superior AUC∞ and Cmax compared to TAD alone or IVAD alone with respect to preventing surgical site infections (SSI).

For surgical procedures limited to skin and subcutaneous tissue, TAD alone is pharmacokinetically superior to IVAD alone or TAD+IVAD for preventing SSI while minimizing exposure of the gut microbiota to antibiotics.

The antibiotic concentration in TISF immediately after TAD is virtually identical to the antibiotic concentration in the TAD solution. TAD can provides a predictable high initial subcutaneous antibiotic concentration at the site of a proposed surgical incision.

There were no adverse local or systemic effects of dilute cefazolin, metronidazole, lidocaine or epinephrine after subcutaneous tumescent infiltration.

The slow rate of systemic absorption of antibiotic following TAD produces a serum antibiotic concentrations-time profile resembling a constant slow IV infusion.

A significant finding was that two drugs with remarkably dissimilar pharmacokinetic profiles in serum after IVAD have virtually identical pharmacokinetic profiles in tumescent interstitial fluid (TISF) after TAD. This suggests that other drugs, for example lidocaine, antiviral, antifungal, or anti-tumor drugs may also demonstrate prolonged high subcutaneous concentrations in TISF after tumescent delivery. TAD may provide safe prolonged extraordinary high concentrations of drugs in subcutaneous TISF where similar concentrations in serum following IVAD would result in significant systemic toxicity. In other words, TAD may be able to achieve localized therapeutic results that would be impossible with IVAD.

Logic of Research Design

Although we did not measure antibiotic concentrations in interstitial fluid (ISF) after IVAD, our research establishes that, at equal doses, the antibiotic concentrations in ISF after IVAD are always less than the antibiotic concentrations in tumescent interstitial fluid (TISF) after TAD at every time point. The algebraic transitivity of mathematical inequalities establishes that if a<b and b<c, then a<c. We have applied this logic to the design of the present research. Consider the following two inequalities:

Inequality 1: Concentrations of cefazolin and metronidazole in ISF after IVAD are always less than, or equal to, their concentrations in serum after IVAD (Müller M, dela Pella A, Derendorf H. Minireview: issues in pharmacokinetics and pharmacodynamics of anti-infective agents: distribution in tissue. *Antimicrob Agents Chemother,* 2004; 48: 1441-1453; van Kralingen S, Taks M, Diepstraten J, van de Garde E M, van Dongen E P, Wiezer M J, van Ramshorst B, Vlaminckx B, Deneer V H, Knibbe C A. Pharmacokinetics and protein binding of cefazolin in morbidly obese patients. Eur J Clin Pharmacol. 2011; 67: 985-992, Howard G W, Begg E J, Chambers S T, Brincat J V, Zhang M, Kirkpatrick C M J. Free and total cefazolin plasma and interstitial fluid concentrations at steady state during continuous infusion. J Antimicrob Chemother. 2002; 50: 429-432; Bielecka-Grzela S, Klimowicz A. Application of cutaneous microdialysis to evaluate metronidazole and its main metabolite concentrations in the skin after a single oral dose. J Clin Pharm Therapeut. 2003; 28: 465-469; Kiang T K L, Hafeli U O, Ensom M H H. A Comprehensive Review on the Pharmacokinetics of Antibiotics in Interstitial Fluid Spaces in Humans: Implications on Dosing and Clinical Pharmacokinetic Monitoring. Clin Pharmacokinet. 2014; 53: 695-730; Brill M J, Houwink A P, Schmidt S, Van Dongen E P, Hazebroek E J, van Ramshorst B, Deneer V H, Mouton J W, Knibbe C A. Reduced subcutaneous tissue distribution of cefazolin in morbidly obese versus non-obese patients determined using clinical microdialysis. J Antimicrob Chemother. 2014; 69: 715-23).

Inequality 2: Our data show that the concentrations of cefazolin and metronidazole in serum after IVAD are always less than their concentrations in subcutaneous TISF after TAD (within the range of antibiotic concentrations in TAD solution utilized in the present study).

Inequality 3: Concentrations of cefazolin and metronidazole in ISF after IVAD are always less than the antibiotic concentrations in TISF after TAD.

This result establishes that TAD is pharmacokinetically superior to IVAD for preventing incisional surgical site infections (SSI). By virtue of the mathematical definitions of AUC∞, Cmax and T>MIC, this result also proves that AUC∞, Cmax and T>MIC in ISF after IVAD are always less than in TISF after TAD.

Prolonged open gastrointestinal surgical procedures require redosing with IV antibiotics for optimal SSI prophylaxis (Jeong S J, Ann H W, Kim J K, Choi H, Kim C O, Han S H, Choi J Y, Peck K R, Kang C I, Yeom J S, Choi Y H, Lim S K, Song Y G, Choi H J, Yoon H J, Kim H Y, Kim Y K, Kim M J, Park Y S, Kim J M. Incidence and risk factors for surgical site infection after gastric surgery: a multicenter prospective cohort study. Infect Chemother. 2013; 45: 422-30). There is a high rate of non-compliance with intraoperative redosing (Goede W J, Lovely J K, Thompson R L, Cima R R. Assessment of prophylactic antibiotic use in patients with surgical site infections. Hosp Pharm. 2013; 48: 560-7). Our data suggests that, because of the prolonged systemic absorption of antibiotics following TAD, the combination of TAD+IVAD provides prolonged high subcutaneous and serum antibiotic concentrations and may reduce the need for re-dosing (Adembri C, Ristori R, Chelazzi C, Arrigucci S, Cassetta M I, De Gaudio A R, Novelli A. Cefazolin bolus and continuous administration for elective cardiac surgery: Improved pharmacokinetic and pharmacodynamic parameters. J Thorac Cardiovasc Surg. 2010; 140: 471-475).

Tumescent Lidocaine Anesthesia

Dilute lidocaine, epinephrine and sodium bicarbonate are essential components of the TAD solution. Dilute epinephrine in a local tumescent antibiotic solution produces delayed systemic absorption of antibiotics, prolonged localized high concentrations of antibiotics, long-lasting local capillary vasoconstriction and incision-site hemostasis. Dilute lidocaine eliminates the pain of subcutaneous antibiotic injection. Large volumes of dilute lidocaine with epinephrine provide rapid onset of prolonged local anesthesia, systemic lidocaine absorption with prolonged therapeutic serum lidocaine concentrations and pre-emptive, interoperative and post-operative analgesia, reduced post-operative narcotic use and earlier postoperative ambulation (De Oliveira G S Jr, Fitzgerald P, Streicher L F, Marcus R J, McCarthy R J. Systemic lidocaine to improve postoperative quality of recovery after ambulatory laparoscopic surgery. Anesth Analg. 2012; 115: 262-67; Fierheller E E, Caulkett N A, Haley D B, Florence D, Doepel L. Onset, duration and efficacy of four methods of local anesthesia of the horn bud in calves. Vet Anaesth Analg. 2012; 39: 431-5; Katz J, Clarke H, Seltzer Z. Preventive analgesia: quo vadimus? Anesth Analg 2011; 113: 1242-1253; Rosaeg O P, Bell M, Cicutti N J, Dennehy K C, Lui A C, Krepski B. Pre-incision infiltration with lidocaine reduces pain and opioid consumption after reduction mammoplasty. Reg Anesth Pain Med. 1998; 23: 575-579; Cui W, Li Y, Li S, Wang R, Li J. Systemic administration of lidocaine reduces morphine requirements and postoperative pain of patients undergoing thoracic surgery after propofol-remifentanil-based anaesthesia. Eur J Anaesthesiol. 2010; 27: 41-46). Lidocaine is has bactericidal effects (Sakuragi T, Ishino H, Dan K. Bactericidal activity of clinically used local anesthetics on *Staphylococcus aureus.* Reg Anesth. 21: 239-42, 1996; Parr A M, Zoutman D E, Davidson J S. Antimicrobial activity of lidocaine against bacteria associated with nosocomial wound infection. Ann Plast Surg. 43: 239-45, 1999; Igarashi T, Suzuki T, Mori K, Inoue K, Seki H, Yamada T, Kosugi S, Minamishima S, Katori N, Sano F, Abe T, Morisaki H. The Effects of Epidural Anesthesia on Growth of *Escherichia coli* at Pseudosurgical Site: The Roles of the Lipocalin-2 Pathway. Anesth Analg. 2015; 121: 81-89).

Published clinical research supports our hypothesis that TAD decreases the risk of SSI compared to IVAD. In a 1995 study, IVAD of metronidazole (500 mg) for abdominal wall surgery, resulted in plasma and muscle levels of metronidazole ranging from 5.7 to 15.7 µg/mL, well above the MIC for 90 percent of *Bacteroides fragilis*, however metronidazole concentration in subcutaneous fat was 0.6-1.7 µg/ml and did not achieve therapeutic levels (Badia J M, de la Torre R, Farré M, Gaya R, Martínez-Ródenas F, Sancho J J, Sitges-Serra A. Inadequate levels of metronidazole in subcutaneous fat after standard prophylaxis. Br J Surg. 1995; 82: 479-82). In the present study, a TAD solution containing 500 mg of metronidazole produced a Cmax=370 µg/mL in tumescent interstitial fluid.

In a 2011 study, 8 of 10 obese subjects and 3 of 10 normal controls had a subcutaneous bioavailability (AUC) of free cefoxitin after IVAD that was 10 times less than the serum bioavailability after IVAD (Toma O, Suntrup P, Stefanescu A, London A, Mutch M, Kharasch E. Pharmacokinetics and tissue penetration of cefoxitin in obesity: Implications for risk of surgical site infection. Anesth Analg 2011; 113: 730-737). Cefoxitin and cefazolin have similar pharmacokinetic profiles (Wise R, Gillett A P, Cadge B, Durham S R, BakerS. The influence of protein binding upon tissue fluid levels of six β-lactam antibiotics. J Infect Dis. 1980; 142: 77-82; Waterman N G, Raff M J, Scharfenberger L, Barnwell P A. Protein binding and concentrations of cephaloridine and cefazolin in serum and interstitial fluid of dogs. J Infect Dis. 1976; 133:642-647; Howard W G, Begg E J, Chambers S T, Brincat J V, Zhang M, Kirkpatrick C M J. Free and total plasma interstitial fluid concentrations as steady state during continuous infusion. J Antimicrob Chemo. 2002; 50: 429-432; Kirby W M M, Regamey C. Pharmacokinetics of Cefazolin Compared with Four Other Cephalosporins J Infect Dis 1973; 128: S341-S346; Wise R, Donovan A, Ambrose N S, Allcock J E. The penetration of cefoxitin into peritoneal fluid. J Antimicrob Chemoth 1981; 8: 453-457; Neu H C. Comparison of pharmacokinetics of cefamandole and other cephalosporin compounds. J Infect Dis. 1978; 137 Supp: S80-S87). In our study serum bioavailability of cefazolin after IVAD was 16 times less than subcutaneous bioavailability of cefazolin after TAD. It follows that IVAD provides approximately 160 (10×16) times less subcutaneous bioavailability (of cefoxitin or cefazolin) than does TAD for a significant proportion of patients. Note that TAD produces such an extreme dilution of subcutaneous interstitial fluid that essentially all antibiotic in TISF can be regarded as unbound protein-free.

Subcutaneous antibiotic delivery for local subcutaneous effect is uncommon. However, subcutaneous antibiotic delivery for systemic effect is commonly used for palliative therapy in Europe (Azevedo E F, Barbosa L A, DeBortoli Cassiani S H. Administration of antibiotics subcutaneously: an integrative literature review. Acta Paul Enferm. 2012; 25: 817-22; Robelet A, Caruba T, Corvol A, Bégué D, Gisselbrecht M, Saint-Jean O, Prognon P, Sabatier B. Antibiotiques par voie sous-cutanee chezla personne agee. Presse Med. 2009; 38: 366-76; Frasca D, Marchand S, Petitpas F, Dahyot-Fizelier C, Couet W, Mimoz O. Pharmacokinetics of ertapenem following intravenous and subcutaneous infusions in patients. Antimicrob Agents Chemother. 2010; 54: 924-6; Walker P, Neuhauser M N, Tam V H, Willey J S, Palmer J L, Bruera E, Prince R A. Subcutaneous administration of cefepime. Pain Symptom Manage. 2005; 30:170-4; Melin-Coviaux F, Hary L, Hurtel A S, Andrejak M, Grumbach Y. Etude pharmaco-clinique comparative de la ceftriaxone par voie sous-cutanee et intraveineuse chez la personne agee. Revue Geriatr. 2000; 25(5): 337-37; Bricaire F, Castaing J L, Pocidalo J J, Vilde J L. Etude de la pharmacocinétique et de la tolerance de la ceftriaxone administré par voie sous-cutané. Pathol Biol (Paris). 1998; 36 (5 Pt 2): 702-5; Borner K, Lode H, Hampel B. Pfeuffer M, Koeppe P. Comparative pharmacokinetics of ceftriaxone after subcutaneous and intravenous administration. Chemotherapy. 1985; 31: 237-45; Gauthier D, Schambach S, Crouzet J, Sirvain S, Fraisse T. Subcutaneous and intravenous ceftriaxone administration in patients more than 75 years of age. Med Mal Infect. 2014; 44:275-80; Barbot A, Venisse N, Rayeh F, Bouquet S, Debaene B, Mimoz O. Pharmacokinetics and pharmacodynamics of sequential intravenous and subcutaneous teicoplanin in critically ill patients without vasopressors. Intensive Care Med. 2003; 29: 1528-34; Champoux N, Du Souich P, Ravaoarinoro M, Phaneuf D, Latour J, Cusson J R. Single-dose pharmacokinetics of ampicillin and tobramycin administered by hypodermoclysis in young and older healthy volunteers. Br J Clin Pharmacol. 1996; 42: 325-31). Although subcutaneous delivery of cefazolin or metronidazole is considered "off-label", our data and published reports suggest subcutaneous cefazolin or metronidazole represent a non-significant risk of harm to patients (Bhargava P, Mehrotra N, Kumar A. Wound infection after metronidazole infiltration. Trop Doct. 2006; 36:37-8; Shubing W, Litian Z. Preventing infection of the incision after appendectomy by using metronidazole preoperatively to infiltrate tissues at the incision. Am J Surg. 1997; 174: 422-4; Quendt J, Blank I, Seidel W. Peritoneal and subcutaneous administration of cefazolin as perioperative antibiotic prophylaxis in colorectal operations. Prospective randomized comparative study of 200 patients. Langenbecks Arch Chir. 1996; 381: 318-22; el-Sefi T A, el-Awady H M, Shehata M I, al-Hindi M A. Systemic plus local metronidazole and cephazolin in complicated appendicitis: a prospective controlled trial. J R Coll Surg Edinb. 1989; 34: 13-6).

Risks of TAD

Human error is the most dangerous aspect of TAD. Legible written signed physician orders are absolutely essential. Orders must specify the amount of lidocaine in terms of milligrams. It is unsafe to order 1000 mg of lidocaine per bag in terms of 100 ml of 1% lidocaine; Murphy's Law assures us that someone will inadvertently use 100 ml of 2% lidocaine. Every bag of TAD solution must be clearly labeled on both sides with tumescent safety labels that state, "Subcutaneous Tumescent Lidocaine, Not for IV." IV delivery of a TAD solution may be fatal.

These pharmacokinetic Phase 1 research findings and current literature provide support that tumescent antibiotic delivery (TAD) will reduce the risk of incisional SSI, reduce the risk of antibiotic resistance, and reduce antibiotic redosing requirements during prolonged surgical procedures (Goede W J, Lovely J K, Thompson R L, Cima R R. Assessment of prophylactic antibiotic use in patients with surgical site infections. Hosp Pharm. 2013; 48: 560-7).

The systemic effects of lidocaine absorption following TAD suggest the hypothesis that TAD will reduce the risks of thromboembolism, reduce the systemic and local inflammatory response to surgery, reduce postoperative narcotic requirements and facilitate earlier postoperative ambulation compared to IVAD alone.

Conclusion

Compared to IVAD alone, pharmacokinetic data showed that TAD with concomitant IVAD provides superior antibiotic bioavailability in both local subcutaneous interstitial fluid and serum, suggesting TAD+IVAD might improve SSI prevention. Tumescent delivery of dilute cefazolin and metronidazole represents a non-significant risk of harm to patients.

TABLE 12

Cefazolin, Abdomen

| Cefazolin Marker | Tissue Sampled | Mode of Delivery | TAD Solution (mg/L) | Dose (mg) | Cmax (µg/ml) | AUC (µg-hr/ml) |
|---|---|---|---|---|---|---|
| Closed Square | TISF | TAD | 900 | 1000 | 823 | 5349 |
| Closed Triangle | TISF | TAD | 450 | 1000 | 457 | 2339 |
| Open Circle | serum | IVAD | — | 1000 | 146 | 324 |
| Open Square | serum | TAD | 900 | 1000 | 20.2 | 246 |
| Open Triangle | serum | TAD | 450 | 1000 | 11 | 112 |

TABLE 13

Cefazolin, Breasts

| Cefazolin Marker | Tissue Sampled | Mode of Delivery | TAD (mg/L) Solution | Dose (mg) | Cmax (µg/ml) | AUC (µg-hr/ml) |
|---|---|---|---|---|---|---|
| Closed Square | TISF | TAD | 450 | 500 | 467 | 4071 |
| Closed Triangle | TISF | TAD | 225 | 500 | 209 | 1587 |
| Open Circle | serum | IVAD | — | 1000 | 123 | 340 |
| Open Square | serum | TAD | 450 | 500 | 19.8 | 240 |
| Open Triangle | serum | TAD | 225 | 500 | 10.2 | 115 |

TABLE 14

Cefazolin, Hips & Outer Thighs

| Cefazolin Marker | Tissue Sampled | Mode of Delivery | TAD (mg/L) Solution | Dose (mg) | Cmax (µg/ml) | AUC (µg-hr/ml) |
|---|---|---|---|---|---|---|
| Closed Square | TISF | TAD | 228 | 870 | 175 | 1196 |
| Closed Triangle | TISF | TAD | 228 | 435 | 177 | 1332 |
| Open Circle | serum | IVAD | — | 1000 | 156 | 271 |
| Open Square | serum | TAD | 228 | 870 | 16.2 | 178 |
| Open Triangle | serum | TAD | 228 | 435 | 6.6 | 64.6 |

TABLE 15A

Cefazolin, Abdomen

| Cefazolin Marker | Tissue Sampled | Mode of Delivery | TAD (mg/L) Solution | Dose (mg) | Cmax (µg/ml) | AUC (µg-hr/ml) |
|---|---|---|---|---|---|---|
| Closed Square | TISF | TAD | 413 | 500 | 370 | 2580 |
| Open Circle | serum | IVAD | — | 500 | 175 | 292 |
| Open Square | serum | TAD | 413 | 500 | 9.3 | 129 |

TABLE 15B

Metronidazole, Abdomen

| Metronidazole Marker | Tissue Sampled | Mode of Delivery | TAD (mg/L) Solution | Dose (mg) | Cmax (µg/ml) | AUC (µg-hr/ml) |
|---|---|---|---|---|---|---|
| Closed Triangle | TISF | TAD | 413 | 500 | 160 | 1032 |
| Open Diamond | serum | IVAD | — | 500 | 14 | 127 |
| Open Triangle | serum | TAD | 413 | 500 | 4.8 | 81 |

TABLE 16A

Cefazolin, Abdomen

| Cefazolin Marker | Tissue Sampled | Mode of Delivery | TAD (mg/L) Solution | TAD Dose (mg) | IVAD Dose (mg) | Cmax (µg/ml) | AUC (µg-hr/ml) |
|---|---|---|---|---|---|---|---|
| Closed Square | TISF | TAD | 345 | 1200 | — | 394 | 2484 |
| Closed Triangle | TISF | TAD + IVAD | 400 | 800 | 400 | 354 | 2977 |
| Open Circle | serum | IVAD | — | — | 1200 | 152 | 325 |
| Open Square | serum | TAD | 345 | 1200 | — | 18 | 144 |
| Open Triangle | serum | TAD + IVAD | 400 | 800 | 400 | 60 | 300.5 |

TABLE 16B

| Metronidazole, Abdomen | | | | | | | |
|---|---|---|---|---|---|---|---|
| Metronidazole Marker | Tissue Sampled | Mode of Delivery | TAD (mg/L) Solution | TAD (mg) Dose | IVAD (mg) Dose | Cmax (μg/ml) | AUC (μg-hr/ml) |
| Closed Square | TISF | TAD | 172 | 600 | — | 160 | 1032 |
| Closed Triangle | TISF | TAD + IVAD | 200 | 400 | 200 | 150 | 1126 |
| Open Circle | serum | IVAD | — | — | 600 | 14 | 127 |
| Open Square | serum | TAD | 172 | 600 | — | 4.8 | 81 |
| Open Triangle | serum | TAD + IVAD | 200 | 400 | 200 | 5.9 | 117 |

TABLE 17

Dose, concentration and volumes of cefazolin, lidocaine in the TAD solutions.

| | Subject #1: 74.3 kg, Abdomen | | Subject #2: 76.4 kg, Breast(s) IVAD: 500 mg Cefazolin | | Subject #3: 66.4 kg, Hips & Outer Thighs IVAD: 1 gm Cefazolin | |
|---|---|---|---|---|---|---|
| | IVAD: 1 gm Cefazolin | | TAD1 | TAD2 | TAD1 | TAD2 |
| Drugs in TAD bag | TAD1 | TAD2 | (1 Breast) | (2 Breasts) | (Unilateral) | (Bilateral) |
| Cefazolin (mg) | 1000 mg | 1000 mg | 500 mg | 500 mg | 435 mg | 870 mg |
| Lidocaine 1% (10 mg/ml) | 1 gm/100 ml | 1 gm/100 ml | 1 gm/100 ml | 1 gm/100 ml | 850 mg/85 ml | 850 mg/85 ml |
| Epinephrine | 1 mg | 1 mg | 1 mg | 1 mg | 0.85 mg | 0.85 mg |
| Na Bicarbonate 1 mEq/ml | 10 mEq/10 ml | 10 mEq/10 ml | 10 mEq/10 ml | 10 mEq/10 ml | 10 mEq/10 ml | 10 mEq/10 ml |
| Physiologic saline 0.9% | 1000 ml | 1000 ml | 1000 ml | 1000 ml | 1,000 ml | 1,000 ml |
| | TAD Volumes | | TAD Volumes | | TAD Volumes | |
| Total TAD Volume/bag | 1,110 ml | 1,110 ml | 1,110 ml | 1,110 ml | 1,095 ml | 1,095 ml |
| Total Volume Infiltrated | 1,110 ml | 2,220 ml | 1,110 ml | 2,220 ml | 1,887 ml | 3,774 ml |
| | TAD Concentrations | | TAD Concentrations | | TAD Concentrations | |
| Lidocaine mg/L | 900 mg/L | 900 mg/L | 900 mg/L | 900 mg/L | 775 mg/L | 775 mg/L |
| Epinephrine mg/L | 0.9 mg/L | 0.9 mg/L | 0.9 mg/L | 0.9 mg/L | 0.77 mg/L | 0.77 mg/L |
| Cefazolin mg/L | 900 mg/L | 450 mg/L | 450 mg/L | 225 mg/L | 228 mg/L | 228 mg/L |
| Lidocaine dosage (mg/kg) | 13.45 mg/kg | 26.9 mg/kg | 13.1 mg/kg | 26.2 mg/kg | 22.1 mg/kg | 44.1 mg/kg |

TABLE 18

Dose, concentration and volumes of cefazolin, metronidazole, lidocaine in the tumescent antimicrobial delivery (TAD) solutions and by intravenous antimicrobial delivery (IVAD).

| | Subject #4, 66.4 kg, Abdomen IVAD: 500 mg Cefazolin & 500 mg Metronidazole | Subject #5, 83 kg, Abdomen IVAD: 1,200 mg Cefazolin & 600 mg Metronidazole | |
|---|---|---|---|
| Drugs in TAD bag | TAD1 | TAD1 | TAD2 + IVAD |
| Cefazolin (mg) | 500 mg | 1,200 mg | 400 mg IVAD + 800 mg/2 L TAD |
| Metronidazole (mg) | 500 mg/100 ml | 600 mg in 1200 ml | 200 mg IVAD + 400 mg/2 L TAD |
| Lidocaine 1% (10 mg/ml) | 1 gm/100 ml | 1 gm/100 ml | 1 gm/100 ml |
| Na Bicarbonate 1 mEq/ml | 10 mEq/10 ml | 10 mEq/10 ml | 10 mEq/10 ml |
| Physiologic saline 0.9% | 1000 ml | 1000 ml | 809 ml |
| | TAD Volumes | TAD Volumes | |
| Total TAD volume/bag | 1,210 ml | 1,221 ml | 1000 ml |
| Total volume Infiltrated | 1,210 ml | 3,483 ml | 2000 ml |

TABLE 18-continued

Dose, concentration and volumes of cefazolin, metronidazole, lidocaine in the tumescent antimicrobial delivery (TAD) solutions and by intravenous antimicrobial delivery (IVAD).

|  | TAD Concentrations | TAD Concentrations |  |
| --- | --- | --- | --- |
| Lidocaine mg/L | 825 mg/L | 819 mg/L | 1 gm/L |
| Epinephrine mg/L | 0.83 mg/L | 0.82 mg/L | 1 mg/L |
| Cefazolin mg/L | 413 mg/L | 345 mg/L | 400 mg/L |
| Metronidazole mg/L | 413 mg/L | 172 mg/L | 200 mg/L |
| Lidocaine dosage (mg/kg) | 15.1 mg/kg | 34.4 mg/kg | 24.1 mg/kg |

Example 11

Safety of Tumescent Drug Delivery

We studied 6 subjects over 6 days after subcutaneous infiltration of a 20 ml of tumescent solutions of acyclovir and 20 ml of tumescent gentamicin with 20 ml of subcutaneous normal saline and 20 ml of subcutaneous bacteriostatic saline as controls.

Results:

Subcutaneous TI of Acyclovir (1 gm acyclovir in 1130 ml of tumescent lidocaine solution) resulted in: 1) no stinging upon injection, 2) no ecchymosis and 3) no local tenderness upon palpation in 6 of 6 subjects.

Subcutaneous TI of Gentamicin (80 mg in 1110 ml of tumescent lidocaine solution) resulted in: 1) no stinging upon injection but with 9 to 12 hours of transient erythema and edema, 2) no ecchymosis and 3) no local tenderness upon palpation in 6 of 6 subjects.

Subcutaneous delivery of 0.9% physiologic saline resulted in: 1) stinging (2+/4+) for 1 to 5 minutes after injection, 2) no ecchymosis and 3) no local tenderness upon palpation in 6 of 6 subjects.

Subcutaneous delivery of bacteriostatic saline (1% benzyl alcohol) resulted in: 1) no stinging upon injection, 2) persistent 2+/4+ ecchymosis and 3) persistent local 2+/4+ to 1+/4+ tenderness in 6 of in 6 of 6 subjects. Bacteriostatic saline is commonly used as a vehicle for intradermal and subcutaneous drug injections. It is known that 1% benzoyl alcohol is bacteriostatic and provides brief (30 seconds) of local anesthesia. It is not well recognized that 1% benzoyl causes relatively intense subcutaneous inflammation, ecchymosis and prolonged tenderness.

Conclusion: Both acyclovir and gentamicin can be injected subcutaneously in a dilute tumescent solution without any clinically significant adverse effects.

Example 12

Treatment of Acute *Herpes zoster* Pain

We have treated several patients with acute *Herpes zoster* pain. Tumescent lidocaine anesthesia in a TI acyclovir solution eliminates 100% of acute zoster pain for up to 12 hours. Lidocaine also has significant anti-inflammatory properties.

Continued slow infiltration of TAD-acyclovir by means of an elastomeric pump prolongs the tumescent lidocaine anesthesia for days and augments the AUC of acyclovir in zoster-affected skin. The unique combination of anesthesia, antiviral and anti-inflammation is not available with any other mode of drug delivery.

We have found that tumescent acyclovir delivery reduces the intensity and duration of the Zoster pain and blistering. Our clinical experience supports our hypothesis that TI Acyclovir delivery significantly reduces the incidence, intensity and duration of PHN. We are developing a multi-center randomized clinical trial to further support our hypothesis.

The addition of triamcinolone to a solution of TI-Acyclovir for treating acute *Herpes zoster* is controversial because of a small increased risk of group A *Streptococcus* necrotizing soft tissue infections associated with *Herpes simplex* (Jarrett P, Ha T, Oliver F. Necrotizing fasciitis complicating disseminated cutaneous *herpes zoster*. Clin Exp Dermatol. 1998; 23: 87-8; Gnann, J W Jr. Varicella-zoster virus: atypical presentations and unusual complications. J Infect Dis. 2002; 186 Suppl 1: S91-8). A randomized clinical trial has found that there is no benefit to oral prednisolone as an adjunct to acyclovir in preventing PHN (Wood M J, Johnson R W, McKendrick M W, Taylor J, Mandal B K, Crooks J. A randomized trial of acyclovir for 7 days or 21 days with and without prednisolone for treatment of acute *herpes zoster*. N Engl J Med. 1994; 330: 896-900). A sufficiently high local concentration of triamcinolone is likely to be beneficial.

Example 13

Methods of Treating Localized Neuropathic Pain

Chronic neuropathic pain is manifested by unprovoked pain and exaggerated responses to stimuli. A great deal of research has been directed toward treating chronic NP. Chronic neuropathic pain (NP) is resistant to treatment and can be debilitating. (Backonja M M. Defining neuropathic pain. Anesth Analg. 2003; 97: 785-90). Less attention has been directed toward therapies that prevent or attenuate the severity of NP. Prevention of NP may be more achievable than cure. Tumescent lidocaine anesthesia (TLA) can prevent or significantly reduce the severity of neuropathic pain associated with trauma and inflammation.

Precipitating factors for NP typically involve intense pain, or traumatic and inflammatory damage to peripheral nerves. (Kehlet H, Jensen T S, Woolf C J. Persistent postsurgical pain: risk factors and prevention. Lancet. 2006; 367: 1618-25).

TLA provides local (peripheral nervous system) anesthetic effects by eliminating painful sensory neural stimuli and acting as a potent local anti-inflammatory. TLA concomitantly provides distant (central nervous system) effects as a result of slow steady systemic lidocaine absorption from tumescent subcutaneous tissues. (Ferrante F M, Paggioli J, Cherukuri S, Arthur G R. The analgesic response to intravenous lidocaine in the treatment of neuropathic pain. Anesth Analg. 1996; 82: 91-7)

TLA provides preoperative intraoperative and prolonged postoperative local anesthesia all of which are important to treating postoperative pain. (Pogatzki-Zahn E M, Zahn P K. From preemptive to preventive analgesia. Curr Opin Anaesthesiol. 2006; 19: 551-5).

TLA provides potent anti-inflammatory effects on immune cells and molecules involved in the pathophysiology of peripheral neuropathic pain.

TLA can attenuate the severity of neuropathic pain (traumatic wounds) and traumatic neural damage (spinal cord injury) by simultaneously treating the local (direct) inflammatory damage to peripheral sensory nerves and treating distant (central) neural inflammation.

Macrophages comprise the most important cellular component in inflammation-mediated neuropathic pain. (Thacker M A, Clark A K, Marchand F, McMahon S B. Pathophysiology of peripheral neuropathic pain: immune cells and molecules. Anesth Analg. 2007; 105: 838-47).

Lidocaine inhibits macrophage function and inhibits macrophage mediated inflammation. (Wang H L, Zhang W H, Lei W F, Zhou C Q, Ye T. The inhibitory effect of lidocaine on the release of high mobility group box 1 in lipopolysaccharide-stimulated macrophages. Anesth Analg. 2011; 112: 839-44; Lee P Y, Tsai P S, Huan g YH, Huang C J. Inhibition of toll-like receptor-4, nuclear factor-kappaB and mitogen-activated protein kinase by lignocaine may involve voltage-sensitive sodium channels. Clin Exp Pharmacol Physiol. 2008; 35: 1052-8.

Intravenous (IV) lidocaine for palliative care of opioid-refractory cancer pain with a neuropathic component is an effective therapeutic option. Tumescent infiltration of lidocaine is uniquely effective in providing both local anesthesia and systemic analgesia.

Tumescent Lidocaine Anesthesia (TLA) produces both long lasting local anesthesia and prolonged slow systemic lidocaine absorption with serum lidocaine concentrations ranging from 1 to 4n/ml. Thus systemic lidocaine absorption following TLA is clinically equivalent to a slow continuous IV infusion. IV lidocaine infusion produces effective perioperative analgesia.

IV lidocaine provides effective postoperative analgesia after laparoscopic cholecystectomy. (Ram D, Sistla S C, Karthikeyan V S, Ali S M, Badhe A S, Mahalakshmy T. Comparison of intravenous and intraperitoneal lignocaine for pain relief following laparoscopic cholecystectomy: a double-blind, randomized, clinical trial. Surg Endosc. 2014; 28: 1291-7).

IV lidocaine significantly improves postoperative pain after complex spine surgery. (Farag E, Ghobrial M, Sessler D I, Dalton J E, Liu J, Lee J H, Zaky S, Benzel E, Bingaman W, Kurz A. Effect of perioperative intravenous lidocaine administration on pain, opioid consumption, and quality of life after complex spine surgery. Anesthesiology. 2013; 119: 932-40).

IV lidocaine improves preoperative and intraoperative analgesia and reduces surgery-induced immune alterations. (Yardeni I Z, Beilin B, Mayburd E, Levinson Y, Bessler H. The effect of perioperative intravenous lidocaine on postoperative pain and immune function. Anesth Analg. 2009; 109: 1464-9).

Not only is IV effective for preventing perioperative pain and thus preventing postoperative neuropathic pain but also effective in treating neuropathic pain.

Serum lidocaine concentrations of 2 to 5 micrograms/ml are effective following subcutaneous infiltration of lidocaine for treatment of cancer neuropathic pain. (Brose W G, Cousins M J. Subcutaneous lidocaine for treatment of neuropathic cancer pain. Pain. 1991; 45: 145-8).

IV Lidocaine provided complete analgesia for neuropathic pain at a mean serum lidocaine concentration of 3.79±1.00 µg/ml. (Ferrante F M, Paggioli J, Cherukuri S, Arthur G R. The analgesic response to intravenous lidocaine in the treatment of neuropathic pain. Anesth Analg. 1996; 82: 91-7).

Example 14

Tumescent Infiltration Prevents Systemic Inflammation and Sepsis.

Tumescent infiltration of lidocaine combined with tumescent antibiotics has potent any inflammatory effects. Lidocaine has long been known to have significant anti-inflammatory properties. Tumescent infiltration (TI) antibiotic delivery has the potential to significantly reduce the risk of sepsis and inappropriate systemic inflammatory response including organ failure and adult respiratory distress syndrome (ARDS). TI antibiotic delivery reduces sepsis by four independent parameters:

1) Local Lidocaine Antiinflammatory Effects:

TLA delivers interstitial lidocaine concentrations (1000 µg/ml) that are nearly 200 times greater than clinically safe serum lidocaine concentrations (≤5 µg/ml). TLA provides very high concentrations of subcutaneous lidocaine throughout a large volume of tissue at the site of a surgical incision and thus profoundly inhibits local platelet activation, neutrophil priming, platelet-leukocyte aggregation (PLA) and endothelial-platelet and endothelial-leukocyte inflammatory interactions.

Furthermore, the extensive and profound vasoconstriction within tumescent subcutaneous tissue effectively isolates the injured tissue from the central circulation. TLA prevents the contents of cells that have been ruptured by infection, surgery, or trauma, including burn or combat injury, from flooding the systemic circulation and precipitating an excessive inflammatory response. Lidocaine can reduce a systemic inflammatory response. (Mikawa K, Maekawa N, Nishina K, Takau Y, Yaku H, Obara H. Effect of lidocaine pretreatment on endotoxin-induced lung injury in rabbits. Anesthesiology 81:689-699, 1994).

2) Systemic Lidocaine Anti-inflammatory Effects:

The slow systemic lidocaine absorption after tumescent infiltration of lidocaine produces a serum lidocaine-concentration-time profile like that of a slow, constant IV infusion. This systemic effect of local TI lidocaine delivery is unique. IV infusion requires IV access and significant nursing staff attention. In contrast, the systemic absorption of lidocaine after tumescent infiltration offers all the benefits of IV lidocaine with respect to sepsis prevention but TI is does not require IV access and requires much less nursing time.

3) Local Antibiotic Effects:

Tumescent antibiotic delivery (TAD) provides local interstitial antibiotic bioavailability that can be 10 to 100 times grater than that provided by IV antibiotic delivery. Thus TAD is more effective than IV delivery for preventing of surgical site infections and treating localized life-threatening cutaneous infections (e.g. cellulitis in a diabetic or necrotizing soft tissue infections in a traumatic combat injury), both of which are commonly associated with sepsis.

4) Systemic Antibiotic Effects:

TI antibiotic delivery produces a concentration-time profile that resembles that of a prolonged slow constant IV antibiotic infusion. Serum antibiotic concentrations persist far longer following TI antibiotic delivery than after a single rapid IV infusion of antibiotics. Thus TI antibiotic delivery by itself or TI+IV antibiotic delivery can achieve more effective systemic effects and better reduce the risk of sepsis than IV delivery alone.

Evidence that Lidocaine is Anti-inflammatory

Lidocaine reduces platelet activation, platelet aggregation and platelet-leukocyte aggregation in a concentration-dependent fashion. Recent evidence suggests there is a critical connection between infection, cell damage, inflammation and coagulation.

Intracellular contents which are known to be potent triggers of systemic inflammation and thrombosis include mitochondria. cell free DNA, chromatin DNA-histone complexes, extracellular RNA, neutrophil extracellular traps (NETs), polyphosphates secreted from platelet dense granules, and leukocyte contents.

Slow constant IV infusion of lidocaine may decrease the inappropriate leukocyte activation, transmigration across capillary endothelium, interstitial positioning, and recruitment during sepsis. Lidocaine inhibits platelet activation, platelet activation of neutrophils and neutrophil mediated inflammation. Inappropriate activation of neutrophils contributes to tissue damage during inflammatory diseases.

Just as tumescence delays the systemic absorption of lidocaine and antibiotics, the physical isolation produced by tumescent infiltration can delay the systemic absorption of intracellular contents and prevent an excessively rapid systemic exposure to these inflammatory and thrombogenic molecules. The role of Lidocaine as an anti-inflammatory is known (Huang G S, Lin T C, Wang J Y, Ku C H, Ho S T, Li C Y. Lidocaine priming reduces ADP-induced P-selectin expression and platelet-leukocyte aggregation. Acta Anaesthesiol Taiwan. 47:56-61,2009; Futosi K1, Fodor S, Mócsai A. Neutrophil cell surface receptors and their intracellular signal transduction pathways. Int Immunopharmacol. 2013; 17:638-50; Berger C, Rossaint J, Van Aken H, Westphal M, Hahnenkamp K, Zarbock A. Lidocaine reduces neutrophil recruitment by abolishing chemokine-induced arrest and transendothelial migration in septic patients. J Immunol. 2014; 192:367-76; Christian Berger, Jan Rossaint, Hugo Van Aken, Martin Westphal, Klaus Hahnenkamp and Alexander Zarbock. Lidocaine Reduces Neutrophil Recruitment by Abolishing Chemokine-Induced Arrest and Transendothelial Migration in Septic Patients. J Immunology, 2014; 192:367-376; Kawasaki C, Kawasaki T, Ogata M, Sata T, Chaudry I H. Lidocaine enhances apoptosis and suppresses mitochondrial functions of human neutrophils in vitro. J Trauma. 2010; 68:401-8; Lan W, Harmon D, Wang J H, Ghori K, Shorten G, Redmond P. The effect of lidocaine on in vitro neutrophil and endothelial adhesion molecule expression induced by plasma obtained during tourniquet-induced ischaemia and reperfusion. Eur J Anaesthesiol. 2004; 21:892-7; de Klaver M J, Buckingham M G, Rich G F. Lidocaine attenuates cytokine-induced cell injury in endothelial and vascular smooth muscle cells. Anesth Analg. 2003; 97:465-70; Cerletti C, Tamburrelli C, Izzi B, Gianfagna F, de Gaetano G. Platelet-leukocyte interactions in thrombosis. Thromb Res. 2012; 129:263-6).

Neutrophil extracellular traps (NETs) are a significant contributor to systemic inflammation. Platelet TLR4 activates NETs to ensnare bacteria in septic blood (Clark S R, Ma A C, Tavener S A, McDonald B, Goodarzi Z, Kelly M M, Patel K D, Chakrabarti S, McAvoy E, Sinclair G D, Keys E M, Allen-Vercoe E, Devinney R, Doig C J, Green F H, Kubes P. Platelet T L R4 activates neutrophil extracellular traps to ensnare bacteria in septic blood. Nat Med. 2007; 13:463-9; Sun H, Wang X, Degen J L, Ginsburg D. Reduced thrombin generation increases host susceptibility to group A streptococcal infection. Blood. 2009 Feb. 5; 113(6):1358-64; Bianchi M, Hakkim A, Brinkmann V, Siler U, Seger R A, Zychlinsky A, Reichenbach J. Restoration of NET formation by gene therapy in CGD controls aspergillosis. Blood 114(13):2619-22; Fry D E, Sepsis, systemic inflammatory response, and multiple organ dysfunction: the mystery continues. Am Surg. 78: 1-8, 2012; De Meyer S F, Suidan G L, Fuchs T A, Monestier M, Wagner D D. Extracellular Chromatin Is an Important Mediator of Ischemic Stroke in Mice. Arterioscler Thromb Vasc Biol. 2012 May 24; Fuchs T A, Kremer Hovinga J A, Schatzberg D, Wagner D D, Lammle B. Circulating DNA and myeloperoxidase indicate disease activity in patients with thrombotic microangiopathies. Blood. 2012 May 18; Lo Y M, Rainer T H, Chan L Y, Hjelm N M, Cocks R A. Plasma DNA as a prognostic marker in trauma patients. Clin Chem. 46(3): 319-23, 2000; Manfredi A A, Rovere-querini P. The mitochondrion—a Trojan horse that kicks off inflammation? N Eng J Med 362: 2132-2134, 2010; Zhang Q, Raoof M, Chen Y, Sumi Y, Sursal T, et al. Circulating mitochondrial DAMPs cause inflammatory responses to injury Nature 464: 104-107, 2010; De Meyer S F, Suidan G L, Fuchs T A, Monestier M, Wagner D D. Extracellular Chromatin Is an Important Mediator of Ischemic Stroke in Mice. Arterioscler Thromb Vasc Biol. 2012 May 24. [Epub ahead of print]; Fuchs T A, Bhandari A A, Wagner D D. Histones induce rapid and profound thrombocytopenia in mice. Blood. 2011 118: 3708-14. Epub 2011; Zeerleder S, Zwart B, Wuillemin W A, Aarden L A, et al. Elevated nucleosome levels in systemic inflammation and sepsis. Crit Care Med. 31:1947-51, 2003; Kannemeier C, Shibamiya A, Nakazawa F, Trusheim H, et al. Extracellular RNA constitutes a natural procoagulant cofactor in blood coagulation. PNAS 104(15): 6388-6393, 2007; Fuchs T A, Brill A, Duerschmied D, Schatzberg D, Monestier M, Myers D D Jr, et al. Extracellular DNA traps promote thrombosis. Proc Natl Acad Sci USA. 107(36): 15880-5. Epub 2010; Fuchs T A, Brill A, Wagner D D. Neutrophil Extracellular Trap Impact on Deep Vein Thrombosis. Arterioscler Thromb Vasc Biol. 2012 May 31. [Epub ahead of print]; Thomas G M, Carbo C, Curtis B R, Martinod K, Mazo I B, Schatzberg D, et al. Extracellular DNA traps are associated with the pathogenesis of TRALI in humans and mice. Blood. 2012 May 17. [Epub ahead of print]; Brill A, Fuchs T A, Savchenko A S, Thomas G M, Martinod K, De Meyer S F, Bhandari A A, Wagner D D. Neutrophil extracellular traps promote deep vein thrombosis in mice. J Thromb Haemost. 10: 136-44, 2012; Yun T H, Morrissey J H. Polyphosphate and omptins: novel bacterial procoagulant agents. J Cell Mol Med. 13(10): 4146-53. Epub 2009; Müller F, Mutch N J, Schenk W A, Smith S A, et al. Platelet polyphosphates are proinflammatory and procoagulant mediators in vivo. Cell 139(6): 1143-56, 2009; von Brühl ML, Stark K, Steinhart A, Chandraratne S, Konrad I, Lorenz M, et al. Monocytes, neutrophils, and platelets cooperate to initiate and propagate venous thrombosis in mice in vivo. J Exp Med. 209: 819-35. Epub 2012;

Intravenously administered lidocaine increases the anti-inflammatory cytokine Interleukin-10 (IL-10) inhibits the synthesis of pro-inflammatory cytokines (Van Der Wal S, Vaneker M, Steegers M, Van Berkum B, Kox M, Van Der Laak J, Van Der Hoeven J, Vissers K, Scheffer G J. Lidocaine increases the anti-inflammatory cytokine IL-10 following mechanical ventilation in healthy mice. Acta Anaesthesiol Scand. 2015; 59: 47-55).

Concentrations of lidocaine 100-fold higher than safe serum lidocaine concentrations (≤5 µg/ml) effectively reduced reactive oxygen species (ROS) production by human neutrophils. Therapeutic serum lidocaine concentrations have no effect on ROS. Concentration of lidocaine in TLA solution and peak lidocaine concentrations in tumescent subcutaneous interstitial fluid is between 500 μg/ml and 1000 μg/ml (Mikawa K, Akamatsu H, Nishina K, Shiga M, Maekawa N, Obara H, Niwa Y. Inhibitory effect of local anaesthetics on reactive oxygen species production by human neutrophils. Acta Anaesthesiol Scand. 1997; 41: 524-8).

Pretreatment with intravenous lidocaine attenuates the inflammatory lung injury induced by the pancreatic enzymes or hydrochloric acid (Kiyonari Y, Nishina K, Mikawa K, Maekawa N, Obara H. Lidocaine attenuates acute lung injury induced by a combination of phospholipase A2 and trypsin. Crit Care Med. 2000; 28: 484-489; Nishina K, Mikawa K, Takao Y, Shiga M, Maekawa N, Obara H. Intravenous lidocaine attenuates acute lung injury induced by hydrochloric acid aspiration in rabbits. Anesthesiology. 1998; 88: 1300-9).

It is understood that the examples and embodiments described herein are for illustrative purposes only and that various modifications or changes in light thereof will be suggested to persons skilled in the art and are to be included within the spirit and purview of this application and scope of any appended claims. All figures, tables, and appendices, as well as publications, patents, and patent applications, cited herein are hereby incorporated by reference in their entirety for all purposes.

What is claimed is:

1. A tumescent composition comprising a chemotherapy agent dissolved in a tumescent solution, wherein:
   (a) a tumescent concentration of the chemotherapy agent is simultaneously:
      1) Below a threshold for local, subcutaneous tissue toxicity,
      2) above a threshold for positive local therapeutic effect, and
      3) above a concentration safely achievable by intravenous (IV), intramuscular (IM) or oral (PO) delivery;
   (b) the tumescent solution comprises:
      (i) a vasoconstrictor;
      (ii) a pharmaceutically acceptable carrier; and
      (iii) optionally a local anesthetic,
   (c) the tumescent composition does not contain an antibiotic; and
   (d) the chemotherapy agent is selected from the group consisting of an alkylating agent, an antimetabolite, an anti-tumor antibiotic, a topoisomerase inhibitor, a mitotic inhibitor, a corticosteroid, an angiogenesis inhibitor, actinomycin D, adriamycin, alkeran, ara-C, arsenic trioxide (trisenox), avastin, BiCNU, busulfan, carboplatinum, CCNU, cisplatinum, cytoxan, daunorubicin, DTIC, 5-FU, erlotinib, fludarabine, gemcitabine, herceptin, hydrea, idarubicin, ifosfamide, irinotecan, lapatinib, leustatin, 6-MP, methotrexate, mithramycin, mitomycin, mitoxantrone, navelbine, nitrogen mustard, rituxan, 6-TG, taxol, taxotere, topotecan, velban, vincristine, VP-16, and xeloda.

2. The tumescent composition of claim 1, wherein said optional local anesthetic is lidocaine.

3. The tumescent composition of claim 2, wherein the concentration of lidocaine is approximately 100 mg to 1,500 mg per L of solution.

4. A tumescent composition comprising a chemotherapy agent dissolved in a tumescent solution, wherein:
   (a) a tumescent concentration of the chemotherapy agent is simultaneously:
      1) Below a threshold for local, subcutaneous tissue toxicity,
      2) above a threshold for positive local therapeutic effect, and
      3) above a concentration safely achievable by intravenous (IV), intramuscular (IM) or oral (PO) delivery;
   (b) the tumescent solution comprises:
      (i) a vasoconstrictor;
      (ii) a pharmaceutically acceptable carrier; and
      (iii) optionally a local anesthetic,
   (c) the tumescent composition does not contain an antibiotic; and
   (d) said tumescent composition further comprises an anti-inflammatory agent.

5. The tumescent composition of claim 1, wherein said vasoconstrictor comprises epinephrine.

6. The tumescent composition of claim 5 wherein the concentration of epinephrine is approximately 0.2 to 1.5 mg/L.

7. The tumescent composition of claim 1, wherein said tumescent composition further comprises an agent that reduces neuropathic pain or the risk of developing neuropathic pain.

8. A method of subcutaneous delivery of a drug or a therapeutic agent to a subject comprising administering to said subject the tumescent composition according to claim 1.

9. The method of claim 8, wherein infiltration of the tumescent composition achieves both prolonged local drug concentration within a tumescent subcutaneous tissue as well as a prolonged slow constant systemic absorption of drugs from the tumescent tissue into a systemic circulation.

10. The method of claim 8, wherein a pharmacokinetic profile of the systemic absorption resembles a slow, constant, intravenous (IV) infusion.

11. The method of claim 8, wherein the subcutaneous concentration of the drug or therapeutic agent achieved is from about 1-100 times the maximum subcutaneous interstitial fluid concentration that can be achieved by conventional IV, IM or oral delivery of the drug or therapeutic agent.

12. The method of claim 8, wherein local and systemic blood viscosity are reduced in the subject and local and systemic oxygenation of tissues in the subject is increased.

13. The method of claim 8, wherein said tumescent composition comprises an agent that reduces neuropathic pain or the risk of developing neuropathic pain from a cancer.

14. The method of claim 8, wherein the method treats a localized cancer.

15. The method of claim 14, wherein the localized cancer is selected from the group consisting of skin cancer, breast cancer, lymphoma, Pancreatic Adenocarcinoma, Insulinoma, lung cancer, colon cancer, prostate cancer, ovarian cancer and a metastatic cancer.

16. The method of claim 15, wherein said skin cancer is a malignant or benign skin tumor selected from the group consisting of Basal Cell Carcinoma, Squamous Cell Carcinoma, melanoma, Merkel Cell Carcinoma, Kaposi's Sarcoma, Lymphoma of the Skin and Soft Tissue Cancer.

17. A method of subcutaneous delivery of a drug or a therapeutic agent to a subject comprising administering to said subject the tumescent composition according to claim 4.

18. The method of claim 17, wherein said tumescent composition further comprises an agent that reduces neuropathic pain or the risk of developing neuropathic pain from a cancer.

19. The method of claim 17, wherein the method treats a localized cancer.

20. The method of claim 19, wherein the localized cancer is selected from the group consisting of skin cancer, breast cancer, lymphoma, Pancreatic Adenocarcinoma, Insulinoma, lung cancer, colon cancer, prostate cancer, ovarian cancer and a metastatic cancer.

21. The method of claim 20, wherein said skin cancer is a malignant or benign skin tumor selected from the group consisting of Basal Cell Carcinoma, Squamous Cell Carcinoma, melanoma, Merkel Cell Carcinoma, Kaposi's Sarcoma, Lymphoma of the Skin and Soft Tissue Cancer.

\* \* \* \* \*